(12) United States Patent
Chan et al.

(10) Patent No.: US 8,785,405 B2
(45) Date of Patent: Jul. 22, 2014

(54) COMPOUNDS FOR TREATING CANCER AND OTHER DISEASES

(71) Applicant: Pacific Arrow Limited, Hong Kong (CN)

(72) Inventors: Pui-Kwong Chan, Sugarland, TX (US); May Sung Mak, Hong Kong (CN)

(73) Assignee: Pacific Arrow Limited (CN)

( * ) Notice: Subject to any disclaimer, the term of this patent is extended or adjusted under 35 U.S.C. 154(b) by 0 days.

(21) Appl. No.: 14/020,099

(22) Filed: Sep. 6, 2013

(65) Prior Publication Data
US 2014/0024113 A1 Jan. 23, 2014

Related U.S. Application Data

(63) Continuation of application No. 13/259,480, filed as application No. PCT/US2011/044233 on Jul. 15, 2011, which is a continuation-in-part of application No. PCT/US2010/042240, filed on Jul. 16, 2010, and a continuation-in-part of application No. 12/856,322, filed on Aug. 13, 2010, now Pat. No. 8,586,719.

(51) Int. Cl.
*A61K 31/7032* (2006.01)
*A61K 31/704* (2006.01)
*C07H 15/256* (2006.01)

(52) U.S. Cl.
USPC .......................................... 514/33; 536/18.1

(58) Field of Classification Search
None
See application file for complete search history.

(56) References Cited

U.S. PATENT DOCUMENTS

| | | | |
|---|---|---|---|
| 6,197,306 B1 | 3/2001 | Murali et al. |
| 6,231,859 B1 | 5/2001 | Kensil |
| 6,444,233 B1 | 9/2002 | Arntzen et al. |
| 6,616,943 B2 | 9/2003 | Wang et al. |
| 6,689,398 B2 | 2/2004 | Haridas et al. |
| 6,746,696 B2 | 6/2004 | Arntzen et al. |
| 6,962,720 B2 | 11/2005 | Haridas et al. |
| 7,105,186 B2 | 9/2006 | Arntzen et al. |
| 7,189,420 B2 | 3/2007 | Wang et al. |
| 7,262,285 B2 | 8/2007 | Chan et al. |
| 7,488,753 B2 | 2/2009 | Chan et al. |
| 7,514,412 B2 | 4/2009 | Chan et al. |
| 7,524,824 B2 | 4/2009 | Chan et al. |
| 7,670,632 B2 | 3/2010 | Arntzen et al. |
| 7,727,561 B2 | 6/2010 | Chan et al. |
| 7,780,974 B2 | 8/2010 | Gutterman et al. |
| 8,334,269 B2 | 12/2012 | Chan et al. |
| 8,586,719 B2 | 11/2013 | Chan et al. |
| 2003/0082293 A1 | 5/2003 | Wang et al. |
| 2003/0096030 A1 | 5/2003 | Wang et al. |
| 2004/0138151 A1 | 7/2004 | Maes et al. |
| 2005/0209445 A1 | 9/2005 | Gokaraju et al. |
| 2005/0220910 A1 | 10/2005 | Chan et al. |
| 2005/0245470 A1 | 11/2005 | Chan et al. |
| 2005/0276872 A1 | 12/2005 | Chan et al. |
| 2005/0277601 A1 | 12/2005 | Chan et al. |
| 2006/0111310 A1 | 5/2006 | Chan et al. |
| 2006/0122129 A1 | 6/2006 | Chan et al. |
| 2006/0183687 A1 | 8/2006 | Cory |
| 2006/0263458 A1 | 11/2006 | Mak et al. |
| 2007/0161580 A1 | 7/2007 | Chan et al. |
| 2007/0196517 A1 | 8/2007 | San Martin |
| 2007/0212329 A1 | 9/2007 | Bruck et al. |
| 2007/0243269 A1 | 10/2007 | McNeff et al. |
| 2007/0249711 A1 | 10/2007 | Choi et al. |
| 2007/0254847 A1 | 11/2007 | Liu et al. |
| 2008/0058273 A1 | 3/2008 | Yang et al. |
| 2008/0064762 A1 | 3/2008 | Fuchs et al. |
| 2008/0096938 A1 | 4/2008 | Evindar et al. |
| 2008/0112925 A1 | 5/2008 | Hancock |
| 2008/0119420 A1 | 5/2008 | Liu et al. |
| 2009/0041877 A1 | 2/2009 | Mak et al. |
| 2009/0156515 A1 | 6/2009 | Chan et al. |
| 2009/0263512 A1 | 10/2009 | Chan et al. |
| 2010/0204169 A1 | 8/2010 | Chan et al. |
| 2010/0317606 A1 | 12/2010 | Chan et al. |

FOREIGN PATENT DOCUMENTS

| | | |
|---|---|---|
| AU | 2002348988 | 11/2007 |
| AU | 2004281707 | 9/2011 |
| AU | 2009200988 | 3/2013 |
| CA | 2451740 | 12/2003 |
| CA | 2541425 | 1/2013 |
| CN | 93111010.6 | 5/1994 |
| CN | 1092991 A | 10/1994 |
| CN | 1092992 A | 10/1994 |
| CN | 1236792 C | 1/2006 |
| EP | 02781502.6 | 2/2004 |

(Continued)

OTHER PUBLICATIONS

U.S. Office Action, Apr. 11, 2013, for Chan et al., U.S. Appl. No. 11/683,198, filed Mar. 7, 2007.
PCT International Preliminary Report on Patentability, Jun. 25, 2013, for Pacific Arrow Limited, Int'l App'l No. PCT/US2011/044233, filed Jul. 15, 2011.
PCT Notification Concerning Transmittal of International Preliminary Report on Patentability, Jul. 4, 2013, for Pacific Arrow Limited, Int'l App'l No. PCT/US2011/044233, filed Jul. 15, 2011.
Canadian Office Action, May 21, 2013, for Fountain Silver Limited et al., Canadian App'l No. 2,451,740, filed Dec. 18, 2003.
Canadian Office Action, Feb. 26, 2013, for Pacific Arrow Limited, Canadian App'l No. 2,579,231, filed Mar. 6, 2007.

(Continued)

*Primary Examiner* — Jeffrey S. Lundgren
*Assistant Examiner* — Michael Schmitt
(74) *Attorney, Agent, or Firm* — Law Offices of Albert Wai-Kit Chan, PLLC

(57) ABSTRACT

This invention provides a method of synthesizing new active compounds for pharmaceutical uses including cancer treatment, wherein the cancers comprise breast, leukocytic, liver, ovarian, bladder, prostatic, skin, bone, brain, leukemia, lung, colon, CNS, melanoma, renal, cervical, esophageal, testicular, spleenic, kidney, lymphatic, pancreatic, stomach and thyroid cancers. This invention is an anti adhesion therapy which uses the compound as a mediator or inhibitor of adhesion proteins and angiopoietins. It inhibits excess adhesion and inhibits cell attachment. It modulates angiogenesis. The compounds also use as mediator of cell adhesion receptor, cell circulating, cell moving and inflammatory diseases.

20 Claims, 37 Drawing Sheets

(56) References Cited

FOREIGN PATENT DOCUMENTS

Figure 1:
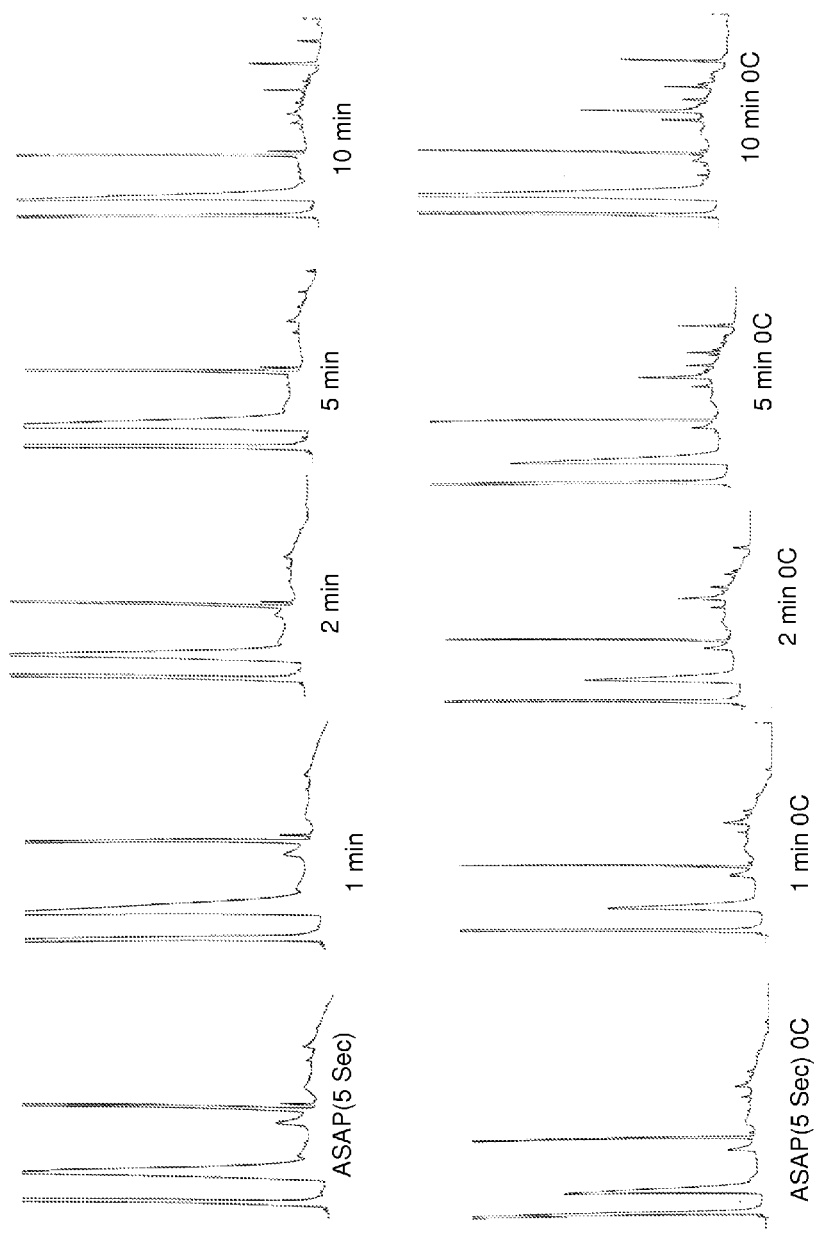

| | | |
|---|---|---|
| HK | 05102536.2 | 3/2005 |
| JP | 61-007285 | 1/1986 |
| JP | 61-130232 | 6/1986 |
| JP | 02-247196 | 10/1990 |
| JP | 2002-515430 A | 5/2002 |
| JP | 2003522442 | 2/2004 |
| JP | 2006-070018 | 3/2006 |
| JP | 4815558 | 9/2011 |
| JP | 4880479 B2 | 2/2012 |
| JP | 5087400 | 9/2012 |
| KR | 1020047002889 | 2/2004 |
| KR | 10-1135824 | 4/2012 |
| NZ | 530449 | 10/2007 |
| NZ | 546138 | 4/2010 |
| NZ | 554037 | 8/2011 |
| SG | 102310 | 3/2006 |
| SG | 120666 | 10/2008 |
| SG | 130542 | 1/2010 |
| TW | 091119471 | 8/2002 |
| TW | 93140030 | 12/2004 |
| TW | 94130519 | 9/2005 |
| WO | 0038700 A1 | 7/2000 |
| WO | 03017919 | 3/2003 |
| WO | 2006029221 | 3/2006 |
| WO | 2006116656 | 11/2006 |
| WO | PCT/US2008/02086 | 2/2008 |
| WO | 2008028060 A2 | 3/2008 |
| WO | 2011009032 | 1/2011 |

OTHER PUBLICATIONS

European Office Communication, May 13, 2013 for Pacific Arrow Limited, European App'l No. EP 10800596.8-1462, filed Mar. 30, 2012.

European Office Communication, Jun. 26, 2013, for Pacific Arrow Limited, European App'l No. EP 04815530.3-1464, filed Jul. 19, 2006.

Australian Office Action, Apr. 16, 2013 for Pacific Arrow Limited, Australian App'l No. 2009226063, filed Sep. 6, 2010.

Ohtsuki et al. "Acylated triterpenoid saponins from Schima noronhae and their cell growth inhibitory activity", Journal of Natural Products, vol. 71, No. 5, Mar. 20, 2008, pp. 918-921, XP002694762.

Sharma et al. "Lanthadenes and their esters as potential antitumor agents", Journal of Natural Products, vol. 71, No. 7, Jun. 14, 2008, pp. 1222-1227, XP002694763.

PCT Written Opinion of the International Searching Authority for PCT/US04/33359, filed Oct. 8, 2004 for Pacific Arrow Limited et al., dated Apr. 12, 2005.

PCT International Search Report for PCT/US04/33359, filed Oct. 8, 2004 for Pacific Arrow Limited et al., dated Apr. 12, 2005.

PCT Written Opinion of the International Searching Authority for PCT/US04/43465, filed Dec. 23, 2004 for Pacific Arrow Limited et al., dated May 17, 2005.

PCT International Search Report for PCT/US04/43465, filed Dec. 23, 2004 for Pacific Arrow Limited et al., dated May 17, 2005.

PCT International Search Report issued on Feb. 6, 2007 for Pacific Arrow Limited, International App'l No. PCT/US2005/031900.

PCT Written Opinion of the International Searching Authority issued on Feb. 6, 2007 for Pacific Arrow Limited, International App'l No. PCT/US2005/031900.

PCT International Preliminary Report on Patentability issued on Mar. 22, 2007 for Pacific Arrow Limited, International App'l No. PCT/US2005/031900.

PCT International Preliminary Report on Patentability issued on Apr. 11, 2006 for Pacific Arrow Limited, International App'l No. PCT/US2004/033359.

PCT International Search Report issued on Nov. 13, 2006 for Pacific Arrow Limited, International App'l No. PCT/US2006/016158.

PCT Written Opinion of the International Searching Authority issued on Nov. 13, 2006 for Pacific Arrow Limited, International App'l No. PCT/US2006/016158.

U.S. Office Action for Mak, et al., U.S. Appl. No. 11/412,659, filed Apr. 27, 2006, Dated Mar. 8, 2007.

U.S. Final Office Action for Mak, et al., U.S. Appl. No. 11/412,659, filed Apr. 27, 2006, Dated Sep. 5, 2007.

U.S. Office Action for Chan, et al., U.S. Appl. No. 11/131,551, filed May 17, 2005, Dated Jan. 22, 2007.

U.S. Notice of Allowability for Chan, et al., U.S. Appl. No. 11/131,551, filed May 17, 2005, Dated May 11, 2007.

U.S. Office Action for Chan, et al., U.S. Appl. No. 11/289,142, filed Nov. 28, 2005, Dated Sep. 27, 2007.

U.S. Office Action for Chan, et al., U.S. Appl. No. 11/267,523, filed Nov. 4, 2005, Dated Sep. 27, 2007.

U.S. Office Action for Chan, et al., U.S. Appl. No. 10/906,303, filed Feb. 14, 2005, Dated Feb. 12, 2007.

U.S. Office Action for Chan, et al., U.S. Appl. No. 10/906,303, filed Feb. 14, 2005, Dated Jul. 27, 2007.

U.S. Office Action for Chan, et al., U.S. Appl. No. 11/117,760, filed Apr. 27, 2005, Dated Jun. 29, 2007.

U.S. Office Action for Chan, et al., U.S. Appl. No. 11/117,760, filed Apr. 27, 2005, Dated Aug. 20, 2007.

PCT International Preliminary Report on Patentability for Pacific Arrow Limited, et al., International Application No. PCT/US2006/016158, filed Apr. 27, 2006, Dated Oct. 30, 2007.

U.S. Office Action for Chan, et al., U.S. Appl. No. 11/117,745, filed Apr. 27, 2005, Dated Jan. 25, 2008.

U.S. Office Communication for Chan, et al., U.S. Appl. No. 11/117,760, filed Apr. 27, 2005, Dated Feb. 8, 2008.

U.S. Office Action for Mak, et al., U.S. Appl. No. 11/412,659, filed Apr. 27, 2006, Dated Feb. 20, 2008.

U.S. Office Action for Chan, et al., U.S. Appl. No. 11/289,142, filed Nov. 28, 2005, Dated Apr. 14, 2008.

U.S. Office Action for Chan, et al., U.S. Appl. No. 11/117,745, filed Apr. 27, 2005, Dated Mar. 12, 2007.

U.S. Office Action for Chan, et al., U.S. Appl. No. 11/117,745, filed Apr. 27, 2005, Dated Aug. 22, 2007.

PCT International Preliminary Report on Patentability issued on Feb. 7, 2006 for Pacific Arrow Limited, International App'l No. PCT/US2004/043465.

U.S. Office Action for Chan, et al., U.S. Appl. No. 10/906,303, filed Feb. 14, 2005, Dated Jan. 4, 2008.

PCT International Search Report issued on Jul. 7, 2008 for Pacific Arrow Limited, International App'l No. PCT/US08/02086.

PCT Written Opinion of the International Searching Authority issued on Jul. 7, 2008 for Pacific Arrow Limited, International App'l No. PCT/US US08/02086.

PCT International Search Report for Pacific Arrow Limited et al., International App'l No. PCT/US07/77273, filed Aug. 30, 2007, Dated Aug. 4, 2008.

PCT Written Opinion of the International Searching Authority for Pacific Arrow Limited et al., International App'l No. PCT/US07/77273, filed Aug. 30, 2007, Dated Aug. 4, 2008.

U.S. Advisory Action for Chan, et al., U.S. Appl. No. 11/289,142, filed Nov. 28, 2005, Dated Jul. 28, 2008.

Notice of Allowability for Chan et al., U.S. Appl. No. 10/906,303, filed Feb. 14, 2005, dated Nov. 26, 2008.

Notice of Allowability for Chan et al., U.S. Appl. No. 11/117,745, filed Apr. 27, 2005, dated Oct. 29, 2008.

Notice of Allowability for Chan et al., U.S. Appl. No. 11/289,142, filed Nov. 28, 2005, dated Oct. 1, 2008.

U.S. Office Action for Chan, et al., U.S. Appl. No. 11/117,760, filed Apr. 27, 2005, Dated Mar. 18, 2009.

U.S. Office Action for Chan, et al., U.S. Appl. No. 11/683,198, filed Mar. 7, 2007, Dated May 1, 2009.

U.S.Office Action for Mak, et al., U.S. Appl. No. 12/195,112, filed Aug. 20, 2008, Dated May 19, 2009.

PCT Written Opinion of the International Searching Authority for PCT/US09/34115, filed Feb. 13, 2009 for Pacific Arrow Limited et al., dated Jun. 2, 2009.

PCT Written Opinion of the International Searching Authority for PCT/US07/77273, filed Aug. 30, 2007 for Pacific Arrow Limited et al., dated Aug. 4, 2008.

(56) References Cited

OTHER PUBLICATIONS

PCT Written Opinion of the International Searching Authority, for PCT/US09/34115, filed Feb. 13, 2009 for Pacific Arrow Limited et al., dated Jun. 2, 2009.
PCT Preliminary Report on Patentability for PCT/US2007/077273, filed Aug. 30, 2007 for Pacific Arrow Limited et al., dated Mar. 12, 2009.
PCT Notification of Transmittal of International Preliminary Examination Report for PCT/IB02/04750, filed Aug. 28, 2002 for Fountain Silver Limited et al., dated Jun. 3, 2003.
U.S. Office Action for Chan, et al., U.S. Appl. No. 11/683,198, filed Mar. 7, 2007, Dated Feb. 18, 2010.
U.S. Office Action for Mak, et al., U.S. Appl. No. 12/195,112, filed Aug. 20, 2008, Dated Feb. 18, 2010.
PCT International Search Report for PCT/US2009/034115, filed Feb. 13, 2009 for Pacific Arrow Limited et al., dated Jun. 2, 2009.
PCT Preliminary Report on Patentability for PCT/US2009/034115, filed Feb. 13, 2009 for Pacific Arrow Limited et al., dated Aug. 26, 2010.
PCT Written Opinion of the International Searching Authority for PCT/US10/42220, filed Jul. 16, 2010 for Pacific Arrow Limited et al., dated Sep. 2, 2010.
PCT International Search Report for PCT/US10/42240, filed Jul. 16, 2010 for Pacific Arrow Limited et al., dated Sep. 2, 2010.
U.S. Office Action for Chan, et al., U.S. Appl. No. 11/683,198, filed Mar. 7, 2007, Dated Sep. 10, 2008.
U.S. Office Action, Jan. 19, 2011, for Chan et al., U.S. Appl. No. 12/344,682, filed Dec. 29, 2008.
U.S. Office Action, May 20, 2011, for Chan et al., U.S. Appl. No. 12/392,795, filed Feb. 25, 2009.
Notice of Allowability for Chan et al., U.S. Appl. No. 11/683,198, filed Mar. 7, 2007, Dated May 5, 2011.
US Office Action, May 12, 2011, for Chan et al., U.S. Appl. No. 12/714,598, filed Mar. 1, 2010.
U.S. Office Action, Oct. 27, 2011, for Chan et al., U.S. Appl. No. 12/344,682, filed Dec. 29, 2008.
PCT Written Opinion of the International Searching Authority, Dec. 6, 2011, for Pacific Arrow Limited, Int'l App'l No. PCT/US2011/044233, filed Jul. 15, 2011.
PCT International Search Report Dec. 6, 2011, for Pacific Arrow Limited, Int'l App'l No. PCT/US2011/044233, filed Jul. 15, 2011.
U.S. Office Action, Dec. 28, 2011, for Chan et al., U.S. Appl. No. 12/714,598, filed Mar. 1, 2010.
U.S. Notice of Allowance, Jan. 30, 2012, for Chan et al., U.S. Appl. No. 11/683,198, filed Mar. 7, 2007.
U.S. Office Action, Mar. 20, 2012, for Chan et al., U.S. Appl. No. 12/344,682, filed Dec. 29, 2008.
U.S. Office Action, Apr. 17, 2012, for Chan et al., U.S. Appl. No. 12/392,795, filed Feb. 25, 2009.
Notice of Allowability for Chan et al., U.S. Appl. No. 12/392,795, filed Feb. 25, 2009, Dated Aug. 15, 2012.
PCT Written Opinion of the International Searching Authority, Oct. 2, 2012, for Pacific Arrow Limited, Int'l App'l No. PCT/US12/46716, filed Jul. 13, 2012.
PCT International Search Report, Oct. 2, 2012, for Pacific Arrow Limited, Int'l App'l No. PCT/US12/46716, filed Jul. 13, 2012.
U.S. Office Action, Dec. 21, 2011, for Chan et al., U.S. Appl. No. 12/541,713, filed Aug. 14, 2009.
U.S. Office Action, Jun. 26, 2012, for Chan et al., U.S. Appl. No. 12/541,713, filed Aug. 14, 2009.
U.S. Office Action, Mar. 21, 2013, for Chan et al., U.S. Appl. No. 12/856,322, filed Aug. 13, 2010.
Supplementary European Search Report issued on Jul. 6, 2005 for Fountain Silver Limited et al., European Patent Application No. 02781502.6.
European Office Communication for Wang, Yun, European App'l No. EP 02781502.6, filed Feb. 25, 2004, Dated Jul. 20, 2007.
European Office Communication for Wang, Yun, European App'l No. EP 02781502.6, filed Feb. 25, 2004, Dated Oct. 12, 2005.
Supplementary European Search Report issued on Oct 13, 2009 for Pacific Arrow Limited et al., European Patent Application No. 04815530.3, PCT/US2004043465.
Supplementary European Search Report issued on Oct. 13, 2009 for Pacific Arrow Limited et al., European Patent Application No. 04809909.7, PCT/US2004033359.
Supplementary European Search Report issued on Oct. 22, 2009 for Mak et al., European Patent Application No. 05810263.3, PCT/US2005031900.
European Office Communication for Pacific Arrow Limited, et al., European App'l No. EP 06751723.5-2123, Dated Jan. 15, 2010.
European Office Communication for Mak May Sung, et al., European App'l No. EP 0581026.3-2123, Dated Dec. 29, 2009.
European Office Communication for Pacific Arrow Limited, et al., European App'l No. EP 04809909.7-2123, Dated Apr. 19, 2010.
European Office Communication for Pacific Arrow Limited, et al., European App'l No. EP 04815530.3-2123, Dated Apr. 19, 2010.
European Office Communication for Mak May Sung, et al., European App'l No. EP 05810263.3-2123, Dated Apr. 19, 2010.
European Office Communication for Pacific Arrow Limited, et al., European App'l No. EP 07841638.5-2123, Dated Apr. 19, 2010.
European Office Communication, Feb. 13, 2012, for Pacific Arrow Limited, European App'l No. EP 07841638.5-2123, filed Mar. 27, 2009.
European Office Communication, Feb. 13, 2012 for Pacific Arrow Limited, European App'l No. EP 05810263.3-2123, filed Mar. 30, 2007.
European Office Communication, Feb. 13, 2012, for Pacific Arrow Limited, European App'l No. EP 04815530.3-2123, filed Jul. 19, 2006.
European Office Communication, Mar. 5, 2012 for Pacific Arrow Limited, European App'l No. EP 04809909.7-2123, filed Mar. 27, 2006.
European Office Communication, Apr. 26, 2012 for Pacific Arrow Limited, European App'l No. EP 09721583.4-2123, filed Sep. 7, 2010.
European Office Communication, Jun. 4, 2012 for Pacific Arrow Limited, European App'l No. EP 02781502.6-2112, filed Feb. 25, 2004.
Notice of Acceptance for Wang, Yun, Australia Patent App'l No. 2002348988, filed Jan. 21, 2004, Dated Jul. 26, 2007.
Australian Office Action for Australian Patent No. 2004281707, Feb. 19, 2010, Pacific Arrow Limited.
Australian Office Action, Mar. 18, 2011 for Pacific Arrow Limited, Australian Patent Application No. 2004281707, filed Oct. 8, 2004.
Notice of Acceptance for Pacific Arrow Limited, Australian Patent App'l No. 2004281707, filed Mar. 23, 2006, Dated May 26, 2011.
Australian Office Action, Feb. 6, 2012 for Pacific Arrow Limited, Australian App'l No. 2009208069, filed Aug. 7, 2009.
Australian Office Action, Feb. 6, 2012 for Pacific Arrow Limited, Australian App'l No. 2005282437, filed Mar. 19, 2007.
Australian Office Action, Feb. 6, 2012 for Pacific Arrow Limited, Australian App'l No. 2009200988, filed Mar. 10, 2009.
Australian Office Action, Jun. 21, 2012 for Pacific Arrow Limited, Australian App'l No. 2008244648, filed Aug. 21, 2009.
Notice of Acceptance for Wang, Yun, New Zealand Patent No. App'l No. 530449, filed Jan. 6, 2004, Dated Jun. 29, 2007.
New Zealand Examination Report for Wang, Yun, New Zealand Patent No. App'l No. 530449, filed Jan. 6, 2004, Dated Feb. 15, 2006.
New Zealand Examination Report for Wang, Yun, New Zealand Patent No. App'l No. 530449, filed Jan. 6, 2004, Dated Apr. 10, 2007.
New Zealand Office Action, Aug. 12, 2009, New Zealand Application No. 546138, filed Mar. 22, 2007.
New Zealand Office Action, Sep. 22, 2009, New Zealand Application No. 546138, filed Mar. 27, 2006.
New Zealand Office Action, Mar. 7, 2011 for Pacific Arrow Limited, New Zealand App'l No. 587973, filed Sep. 14, 2010.
New Zealand Office Action, Mar. 28, 2011 for Pacific Arrow Limited, New Zealand App'l No. 554037, filed Mar. 19, 2007.
New Zealand Office Action, Sep. 24, 2010, for Pacific Arrow Limited, New Zealand App'l No. 579194, filed Aug. 21, 2009.
New Zealand Office Action, Jan. 11, 2012, for Pacific Arrow Limited, New Zealand App'l No. 579194, filed Aug. 21, 2009.

(56) References Cited

OTHER PUBLICATIONS

New Zealand Office Action, Mar. 26, 2012, for Pacific Arrow Limited, New Zealand App'l No. 598934, filed Mar. 21, 2012.
Japan Office Action, Nov. 4, 2008 for Fountain Silver Limited, Japan Patent Application No. 2003-522442, filed Aug. 28, 2002.
Japan Final Office Action, Feb. 23, 2009, for Fountain Silver Limited, Japan App'l No. 2003-522442, filed Feb. 5, 2004.
Japan Office Action, Jan. 14, 2011, for Pacific Arrow Limited, Japan App'l No. 2006-534419, filed Mar. 22, 2006.
Japan Office Action, Mar. 18, 2011, for Pacific Arrow Limited, Japan app'l No. 2006-547422, filed Jun. 16, 2006.
Japan Office Action, Jun. 3, 2011 for Pacific Arrow Limited, Japan App'l No. 2006-534419, filed Mar. 22, 2006.
Japanese Notice of Allowance, Nov. 15, 2011, for Pacific Arrow Limited, Japanese app'l No. 2006-547422, filed Jun. 16, 2006.
Japanese Office Action, Nov. 21, 2011, for Pacific Arrow Limited, Japanese app'l No. 2007-530484, filed Mar. 2, 2007.
Japanese Office Action, May 8, 2012, for Pacific Arrow Limited, Japanese app'l No. 2007-530484, filed Mar. 2, 2007.
Korean Office Action, Nov. 21, 2008 for Fountain Silver Limited, Korean Application No. 10-2004-7002889, filed Aug. 28, 2002.
Korean Office Action, Jun. 3, 2011 for Pacific Arrow Limited, Korean App'l No. 10-2006-7008896, filed May 8, 2006.
Korean Office Action, Jun. 22, 2012 for Pacific Arrow Limited, Korean App'l No. 10-2007-7007902, filed Apr. 6, 2007.
Canadian Office Action, Nov. 7, 2008 for Fountain Silver Limited, Canadian Application No. 2,451,740, filed Dec. 18, 2003.
Canadian Office Action, May 26, 2010 for Fountain Silver Limited, Canadian Application No. 2,451,740, filed Dec. 18, 2003.
Canadian Office Action, Sep. 8, 2011, for Fountain Silver Limited et al., Canadian App'l No. 2,451,740, filed Dec. 18, 2003.
Canadian Notice of Allowance, Oct. 5, 2011, for Pacific Arrow Limited et al, Canadian App'l No. 2541425, filed Oct. 8, 2004.
Canadian Office Action, Jan. 31, 2012, for Pacific Arrow Limited, Canadian Application No. 2,579,231, filed Mar. 6, 2007.
Canadian Office Action, Jul. 5, 2012, for Fountain Silver Limited et al., Canadian App'l No. 2,451,740, filed Dec. 18, 2003.
Taiwan Office Action, Sep. 14, 2004 for Wang Yun, Taiwan Application No. 091119471, filed Aug. 28, 2002.
Taiwan Office Action, Apr. 26, 2005 for Wang Yun, Taiwan Application No. 091119471, filed Aug. 28, 2002.
Taiwan Office Action, Mar. 12, 2010 for Pacific Arrow Limited, Taiwan App'l No. 093140030, filed Dec. 22, 2004.
Taiwan Office Action, Mar. 3, 2011 for Pacific Arrow Limited, Taiwan App'l No. 093140030, filed Dec. 22, 2004.
Taiwan Office Action, Jan. 18, 2012 for Pacific Arrow Limited, Taiwan App'l No. 094130519, filed Sep. 6, 2005.
Chinese Office Action, Aug. 27, 2004 for Wang Yun, Chinese Publication No. CN 1236792C, filed Aug. 28, 2002.
Chinese Office Action, May 27, 2005 for Wang Yun, Chinese Publication No. CN 1236792C, filed Aug. 28, 2002.
Chinese Office Action, Jan. 15, 2010 for Pacific Arrow Limited, et al., Chinese App'l No. 200480036761.7, filed Jun. 8, 2006.
Chinese Office Action, Mar. 27, 2009 for Pacific Arrow Limited, Chinese application No. 2005800375247, filed Jul. 26, 2007.
Chinese Office Action, Apr. 21, 2010 for Pacific Arrow Limited, Chinese application No. 2005800375247, filed Jul. 26, 2007.
Chinese Office Action, Jun. 3, 2011 for Pacific Arrow Limited, Chinese application No. 200880012065.0, filed Oct. 14, 2009.
Chinese Office Action, Jun. 14, 2011, for Pacific Arrow Limited, Chinese App'l No. 200480036761.7, filed Jun. 8, 2006.
Chinese Office Action, Oct. 28, 2011, for Pacific Arrow Limited, Chinese App'l No. 200480038698.0, filed Jun. 23, 2006.
Chinese Office Action, Sep. 28, 2011, for Pacific Arrow Limited, Chinese App'l No. 200480036761.7, filed Jun. 8, 2006.
Chinese Office Action, Mar. 23, 2011, for Pacific Arrow Limited, Chinese App'l No. 200780040744.4, filed Apr. 30, 2009.
Chinese Notice of Allowance, Feb. 1, 2011, for Pacific Arrow Limited, Chinese app'l No. 200580037524.7, filed Apr. 30, 2007.
Chinese Office Action, Apr. 9, 2012, for Pacific Arrow Limited, Chinese App'l No. 200780040744.4, filed Apr. 30, 2009.
Arda, et al. "Saniculoside N from *Sanicula europaea* L." Journal of Natural Products (1997), 60(11), 1170-1173.
Barre, et al. "A bioactive triterpene from *Lantana camara*." Phytochemistry (1997), 45(2), 321-324.
Chen, et al. Studies on the constituents of *Xanthoceras sorbifolia* Bunge. II. Major sapogenol and a prosapogenin from the fruits of *Xanthoceras sorbifolia* Bunge. Chemical & pharmaceutical bulletin (Sep. 1984), 32(9), 3378-83.
Chen, et al. "Studies on the constituents of *Xanthoceras sorbifolia* Bunge. III. Minor prosapogenins from the fruits of *Xanthoceras sorbifolia* Bunge." Chemical & Pharmaceutical Bulletin (1985), 33(1), 127-34.
Chen, et al. "Studies on the constituents of *Xanthoceras sorbifolia* Bunge. IV. Structures of the minor prosapogenins." Chemical & Pharmaceutical Bulletin (1985), 33(3), 1043-8.
Chen, et al. "Studies on the constituents of *Xanthoceras sorbifolia* Bunge. V. Major saponins from the fruits of *Xanthoceras sorbifolia* Bunge." Chemical & Pharmaceutical Bulletin (1985), 33(4), 1387-94.
Koike, et al. "New triterpenoid saponins from *Maesa japonica*." Journal of Natural Products (1999), 62(2), 228-232.
Li, et al. "New guaianolides and xanthine oxidase inhibitory flavonols from *Ajania fruticulosa*." Journal of Natural Products (1999), 62(7), 1053-1055.
Meng, et al. "Antifungal highly oxygenated guaianolides and other constituents from *Ajania fruticulosa*." Phytochemistry (2001), 58(7), 1141-1145.
Sakurai, et al. "Assamicin I and II, novel triterpenoid saponins with insulin-like activity from *Aesculus assamica* Gruff." Bioorganic & Medicinal Chemistry Letters (2002), 12(5), 807-810.
Sindambiwe, et al. "Triterpenoid saponins from *Maesa lanceolata*." Phytochemistry (1996), 41(1), 269-77.
Tuntiwachwuttikul, et al. "A triterpenoid saponin from *Maesa ramentacea*." Phytochemistry (1997), 44(3), 491-495.
Voutquenne, et al. Triterpenoid saponins and acylated prosapogenins from *Harpullia austro-caledonica*. Phytochemistry (2002), 59(8), 825-832.
Waechter, et al. "Antitubercular Activity of Triterpenoids from *Lippia turbinata*." Journal of Natural Products (2001), 64 (1), 37-41.
Zhao, et al. "Four new triterpene saponins from the seeds of *Aesculus chinensis*." Journal of Asian Natural Products Research (2003), 5(3), 197-203.
Zhao, et al. "Three new triterpene saponins from the seeds of *Aesculus chinensis*." Chemical & Pharmaceutical Bulletin (2001), 49(5), 626-628.
Aper, et al. "New acylated triterpenoid saponins from *Maese lanceolata*." Phytochemistry 52 (1999) 1121-1131.
D'Aoquarica, et al. "Isolation and structure elucidation of four new triterpenoid estersaponins from fruits of *Pittosporum tobira* AIT." Tetrahedron 58 (2002) 10127-10136.
Jiang. et al. "Six Triterpenoid Saponins from *Maesa laxiflora*." J. Nat. Prod. 1999. 62, 873-876.
Lu, et al. "Triterpenoid saponins from the roots of tea plants (*Camellia sinensis* var. *assamica*)." Phytochemistry 53 (2000) 941-946.
Seo, et al. "A New Triterpene Saponin from *Pittosporum viridlflorum* from the Madagascar Rainforest." J. Nat. Prod. 2002, 65, 65-68.
Yang, et al. "Anti-HIV-1 Protease Triterpenoid Saponins from the Seeds of *Aesculus chinensis*." J. Nat. Prod. 1999, 62, 1510-1513.
Voutquenne, et al. "Structure-Activity Relationships of Haemolytic Saponins" Pharmaceutical Biology (2002), vol. 40, No. 4, pp. 253-262.
Sirtori, C., "Aescin: Pharmacology, Pharmacokinetic Profile" Pharmacological Research(2001) vol. 44, No. 3, pp. 183-193.
Oda, K. et al., "Adjuvant and Haemolytic Activities of 47 Saponins Derived from Medicinal and Food Plants" Biol. Chem. (2000) vol. 381, pp. 67-74.
Chan, Pui-Kwong, 2007, "Acylation with diangeloyl groups at C21-22 positions in triterpenoid saponins is essential for cytotoxcity towards tumor cells", Biochemical Pharmacology 73(2007): 341-350.

(56) References Cited

OTHER PUBLICATIONS

Lavaud, et al., 1992, "Saponins from *Steganotaenia araliacea*", Phytochemistry, 31(9):3177-3181.
Zhang, et al., 2007, "Cytotoxic triterpenoid saponins from the fruits of *Aesculus pavia* L", Phytochemistry 68(2007): 2075-2086.
Li, et al., 2005, "Two New Triterpenes from the Husks of *Xanthoceras sorbifolia*", Planta Medica, vol. 71:1068-1070.
Voutquenne, et al., 2005, "Haemolytic Acylated Triterpenoid saponins from *Harpullia austro-caledonica*". Phytochemistry, vol. 66: 825-826.
Ma, et al, 2008, "Cytotoxic Triterpenoid Saponins Acylated with Monoterpenic Acid from *Pithecellobium lucidum*", Journal of Natural Products, vol. 71(1): 41-46.
Ushijima, et al, 2008, "Triterpene Glycosides from the Roots of *Codonopsis lanceolata*", Chemical & Pharmaceutical Bulletin, vol. 56(3) 308-314.
Yadava, et al., 2008, "New antibacterial triterpenoid saponin from *Lactuca scariola*", Fitoterapia, vol. 1:1-5.
Wang, et al., 2008, "Bioactive Triterpene Saponins from the Roots of *Phytolacca americana*", Journal of Natural Products, vol. 71(1): 35-40.
Chang, et al, 2007, "Biologically Active Triterpenoid Saponins from *Ardisia japonica*", Journal of Natural Products, vol. 70(2): 179-187.
Akihisa et al, 2006, "Cancer Chemopreventive Effects and Cytotoxic Activities of the Triterpene Acids from the Resin of *Boswellia carteri*", Biological & Pharmaceutical Bulletin, vol. 29(9):1976-1979.
Lang, et al., 2006, "Triterpenoid Saponins from *Lysimachia davurica*", Chemical & Pharmaceutical Bulletin, vol. 54 (10):1380-1383.
Fujioka, et al., 2006, "Antiproliferative Constituents from Umbelliferae Plants. New Triterpenoid Glycosides from the Fruits of *Bupleurum rotundifolium*", Chemical & Pharmaceutical Bulletin, vol. 54 (12):1694-1704.
Rabi, et al., 2007, "Novel triterpenoid 25-hydroxy-3-oxoolean-12-en-28-oic acid induces growth arrest and apoptosis in breast cancer cells", Breast Cancer Research & Treatment, vol. 101:27-36.
Sporn, et al., 2007, "Platforms and Networks in Triterpenoid Pharmacology", Drug Development Research, vol. 68:174-182 (2007).
Puiffe, et al., 2007, "Characterization of Ovarian Cancer Ascites on Cell Invasion, Proliferation, Spheroid Formation, and Gene Expression in an In Vitro Model of Epithelial Ovarian Cancer" Neoplasia, vol. 9(10):820-829.
Ricciardelli, et al., 2006, "Extracellular Matrix of Ovarian Tumors", Seminars in Reproductive Medicine, vol. 24(4): 270-282.
Bang, et al., 2007, "Facile Synthesis of Trisaccharide Moiety Corresponding to Antitumor Activity in Triterpenoid Saponins Isolated from *Pullsatilla* Roots", Chemical & Pharmaceutical Bulletin, vol. 55(12): 1734-1739.
Talmadge, James E., 2008, "Follistatin as an Inhibitor of Experimental Metastasis", Clinical Cancer Research, vol. 14(3) 624-626.
Wei, et al., 2004, "Anti-inflammatory Triterpenoid Saponins from the Seeds of *Aesculus chinensis*", Chemical & Pharmaceutical Bulletin, vol. 52(10): 1246-1248.
Zhu et al, "Preliminary test of chemical constituents of wenguanguo and its multipurpose utilization", Research of Land and Natural Resources (1): 69-71, 1997.
Konoshima, et al. "Antitumor Agents, 82. Cytotoxic Sapogenols from *Aesculus hippocastanum*", Journal of Natural Products vol. 49, No. 4, pp. 650-656, Jul.-Aug. 1986.
2006 Chemical Abstracts Catalog, published 2006 by Chemical Abstracts Service, p. 52.
Maes, et al, "In vitro and in vivo activities of a triterpenoid saponin extract (px-6518) from the plant *Maesa balansae* against visceral *Leishmania* species," Antimicrobial agents and chemotherapy, Jan. 2004, p. 130-136.
Murakami, et al. "New hypoglycemic constituents in "gymnemic acid" from *Gymnema sylvestre*." Chem. Pharm. Bull. 44(2) 469-471 (1996 ).
Na, et al. "Protein tyroshine phosphatase 1B inhibitory activity of triterpenes isolated from *Astilbe koreana*." Bioorg Med Chem Lett. Jun. 15, 2006;16(12): 3273-6.
Zhou, et al. "The first naturally occurring tie2 kinase inhibitor." Org Lett. Dec. 13, 2001;3(25): 4047-9.
Apers Sandra et al., "Antiviral, haemolytic and molluscicidal activities of triterpenoid saponins from *Maese lanceolata*: Establishment of structure-activity relationships", Planta Medica, vol. 67, No. 6, Aug. 2001, pp. 528-532.
Ahmad V U et al., "The Sapogenins from Dodonaea-Viscosa", Fitoterapia, vol. 58, No. 5, 1987, pp. 361-362.
Dizes C et al., "Harpuloside a triterpenoid saponin from *Harpullia ramiflora*", Phytochemistry, Pergamon Press, GB, vol. 48, No. 7, Aug. 1, 1998, pp. 1229-1232.
Cheng, et al. "Two new sterols in the husk of *Xanthoceras sorbifolia*." Chinese Traditional and Herbal Drugs (2001), 32 (3), 199-201.
Cancer cell invasion and metastasis, King's college london, Strand, London WC2R 2Ls, UK, 2010.
Yang et al. "The Influence of aquaporin-1 and microvessel density on ovarian carcinogenesis and ascites formation", International Journal of Gynecological Cancer, vol. 16, No. S1, Feb. 1, 2006, pp. 400-405.
Germonprez N. et al. "In vitro and in vivo anti-leishmanial activity of triterpenoid saponins isolated from *Maesa balansae* and some chemical derivatives", Journal of Medicinal Chemistry, vol. 48 No. 1 Jan. 13, 2005, p. 32-37.
Chemical Abstracts Service, Columbus, Ohio, US, Germonprez N. et al., "Antileishmanial saponins from *Maesa*", Tap Chi Hoa Hoc, 41(spec.), 125-130, 2003.
Dan Peer, et al. "Nanocarriers as an emerging platform for cancer therapy." Nature Publishing Group (2007), 751-760.

COMPOUNDS FOR TREATING CANCER AND OTHER DISEASES

This application is a continuation of Ser. No. 13/259,480, filed Sep. 23, 2011, which is a national stage of PCT/US2011/044233, filed Jul. 15, 2011, which is a continuation-in-part of International App'l No. PCT/US/2010/0042240, filed Jul. 16, 2010, and continuation-in-part of U.S. Ser. No. 12/856,322, filed Aug. 13, 2010. The entire contents of these preceding applications are hereby incorporated by reference into this application.

FIELD OF THE INVENTION

This invention provides compounds, compositions, extracts and methods for inhibiting cancer invasion, cell invasion, or cancer cell invasion.

BACKGROUND OF THE INVENTION

This invention provides methods of synthesizing new compounds for pharmaceutical uses. This invention provides methods, compounds and compositions for treating cancer, inhibiting cancer invasion, cell invasion, or cancer cell invasion, wherein the cancers comprise breast, leukocytic, liver, ovarian, bladder, prostatic, skin, bone, brain, leukemia, lung, colon, CNS, melanoma, renal, cervical, esophageal, testicular, spleenic, kidney, lymphatic, pancreatic, stomach and thyroid cancers

SUMMARY OF THE INVENTION

This invention provides methods of synthesizing new compounds for pharmaceutical uses. This invention provides compounds, compositions, and methods for treating cancer, inhibiting cancer invasion, cell invasion, cancer cell invasion, and metastasis. This invention provides a use of compounds, compositions, for manufacturing medicament for treating cancer, inhibiting cancer invasion, and metastasis. This invention provides compounds for use as mediator or inhibitor of adhesion protein or angiopoietin, This invention provides compounds for use in a method of modulating attachment or adhesion of cells or angiogenesis, by modulating or inhibiting adhesion protein or angiopoietin, The compounds comprise the structures selected from the formulae in the present application, wherein the compounds are synthesized or isolated, wherein the compounds comprise the saponins, triterpenes, pentacyclic triterpenes, and compounds selected from formulae in the present application, wherein the cancers comprise breast, leukocytic, liver, ovarian, bladder, prostatic, skin, bone, brain, leukemia, lung, colon, CNS, melanoma, renal, cervical, esophageal, testicular, spleenic, kidney, lymphatic, pancreatic, stomach and thyroid cancers. This invention provides compounds for use as a mediator for cell circulating, cell moving and inflammatory diseases.

DETAILED DESCRIPTION OF THE FIGURES

FIG. 1 HPLC profiles of esterification products of E4A with Tigloyl chloride (A) from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature (Top row) and 0 C (bottom row).

Figure 2:
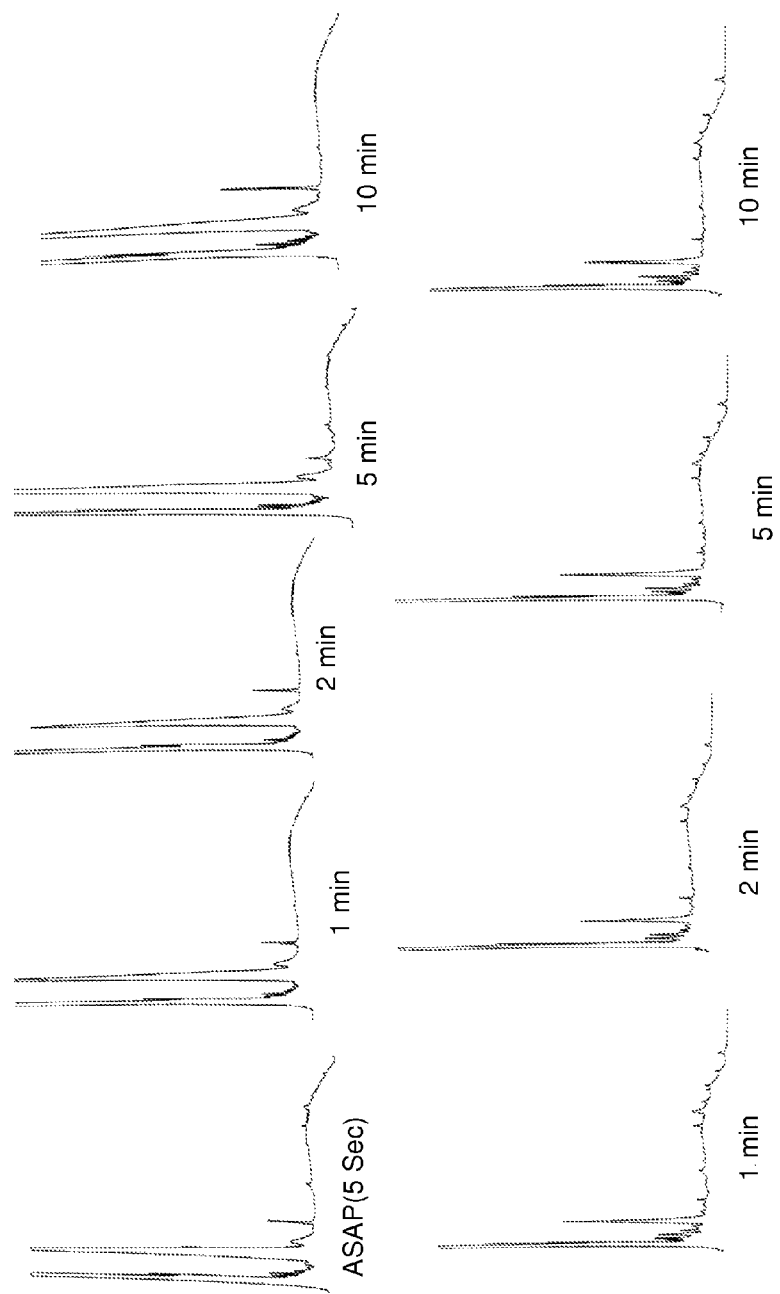

FIG. 2 HPLC profiles of esterification products of E4A with 3,3-dimethylacryloly chloride (B) from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature (Top row) and 0 C (bottom row).

Figure 3:
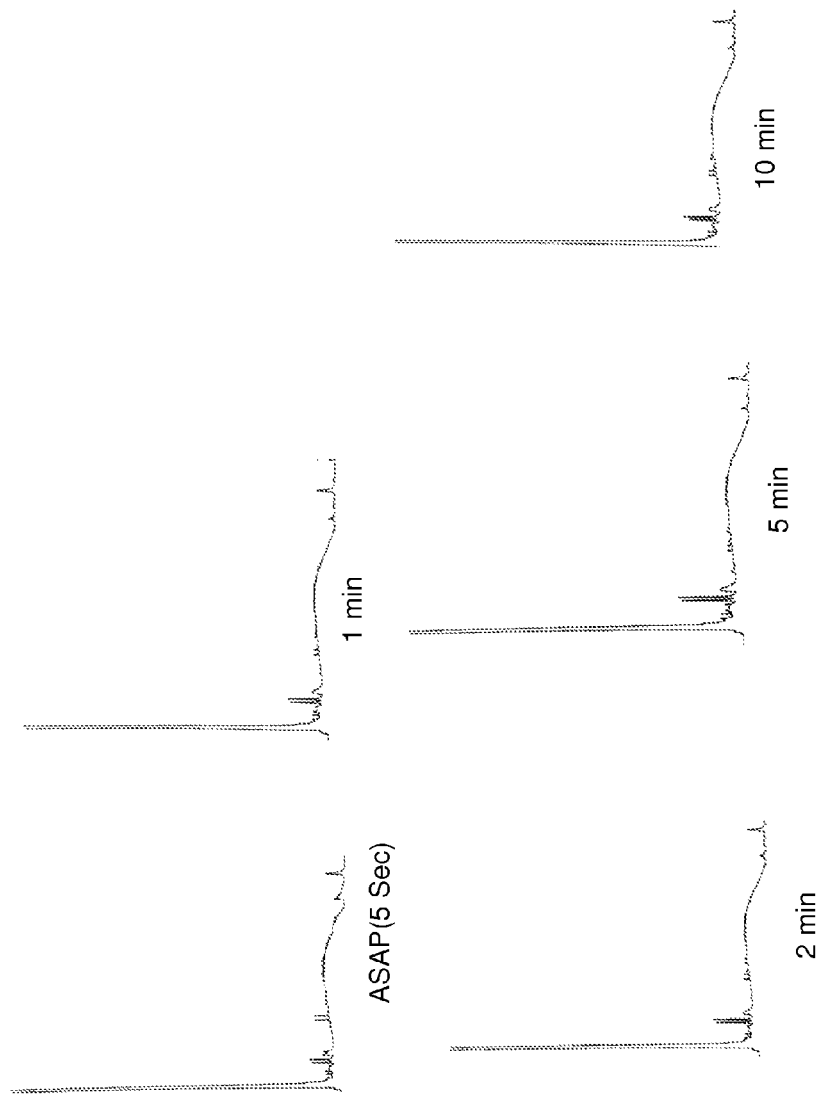

FIG. 3 HPLC profiles of esterification products of E4A with 4-Pentenoyl chloride (C) from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature.

Figure 4:
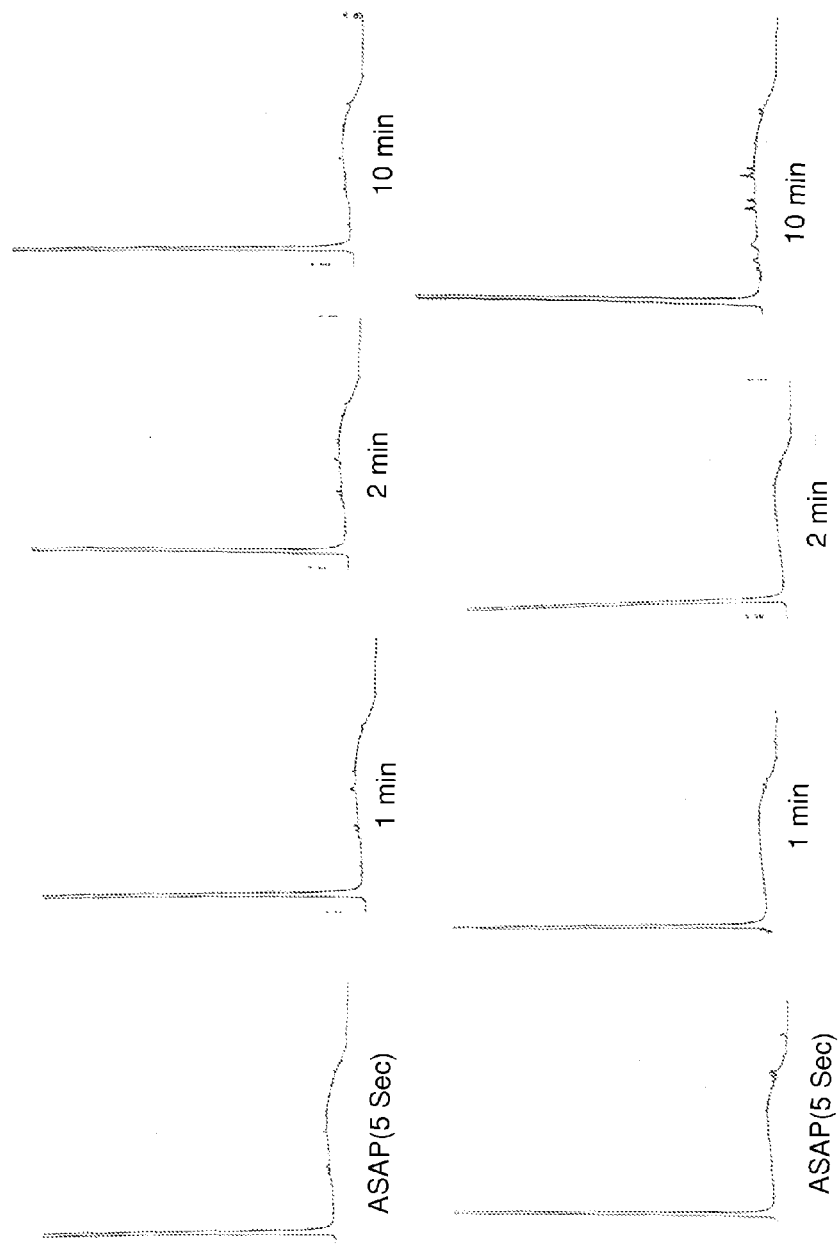

FIG. 4 HPLC profiles of esterification products of E4A with Hexanoly chloride (D) from different times of esterification reaction. Reaction products obtained from each time of reaction (5 sec, 1 min, 2 min, and 10 min) were fractionated by HPLC. The profile is plotted according to HPLC elution time and optical density of fractions. Reaction was performed at 0 C (Top row); and shows the results of HPLC profiles of esterification products of E4A with 2-ethylbutyryl chloride (E) from different times of esterification reaction. Reaction products obtained from each time of reaction (5 sec, 1 min, 2 min, and 10 min) were fractionated by HPLC. The profile is plotted according to HPLC elution time and optical density of fractions. Reaction was performed at 0 C. (bottom row)

Figure 5:
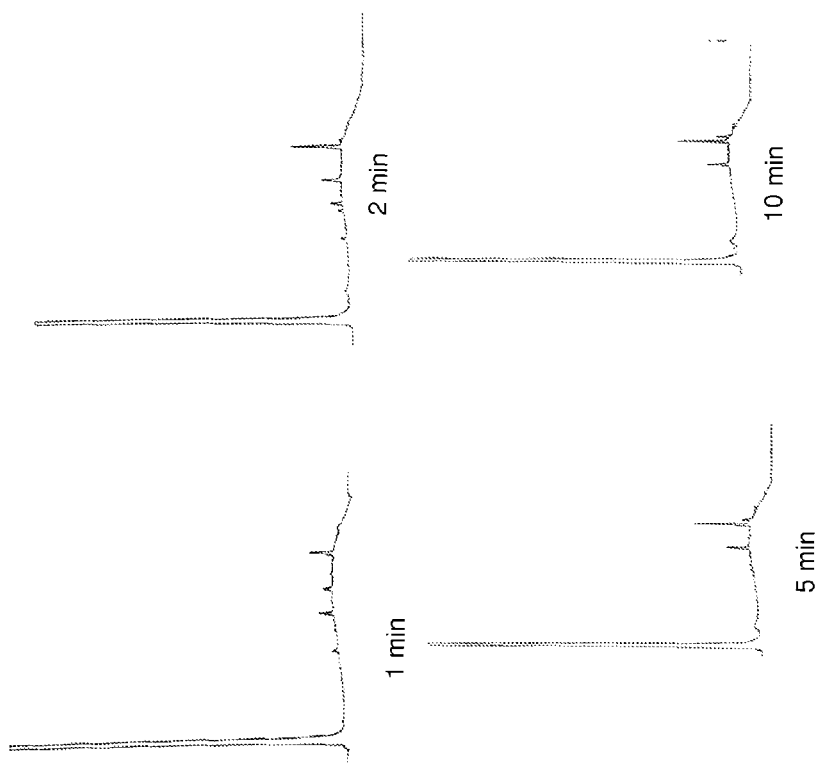

FIG. 5 HPLC profiles of esterification products of E4A with Acetyl chloride (H) from different times of esterification reaction. Reaction products obtained from each time of reaction (1 min, 2 min, 5 min and 10 min) were fractionated by HPLC. The profile is plotted according to HPLC elution time and optical density of fractions. Reaction was performed at Room temperature.

Figure 6:
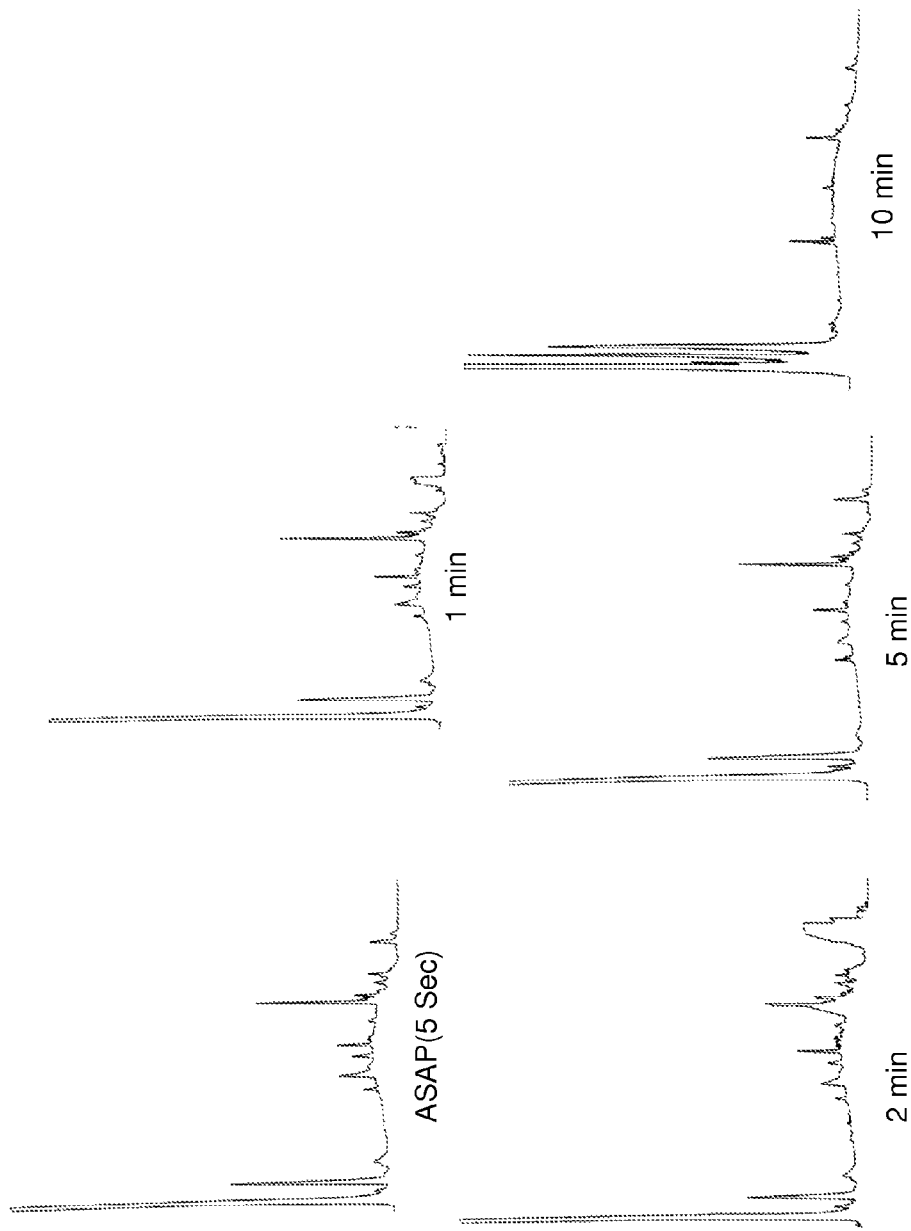

FIG. 6 HPLC profiles of esterification products of E4A with Crotonoyl chloride (I) from different times of esterification reaction. Reaction products obtained from each time of reaction (5 sec, 1 min, 2 min, 5 min and 10 min) were fractionated by HPLC. The profile is plotted according to HPLC elution time and optical density of fractions. Reaction was performed at Room temperature.

Figure 7:
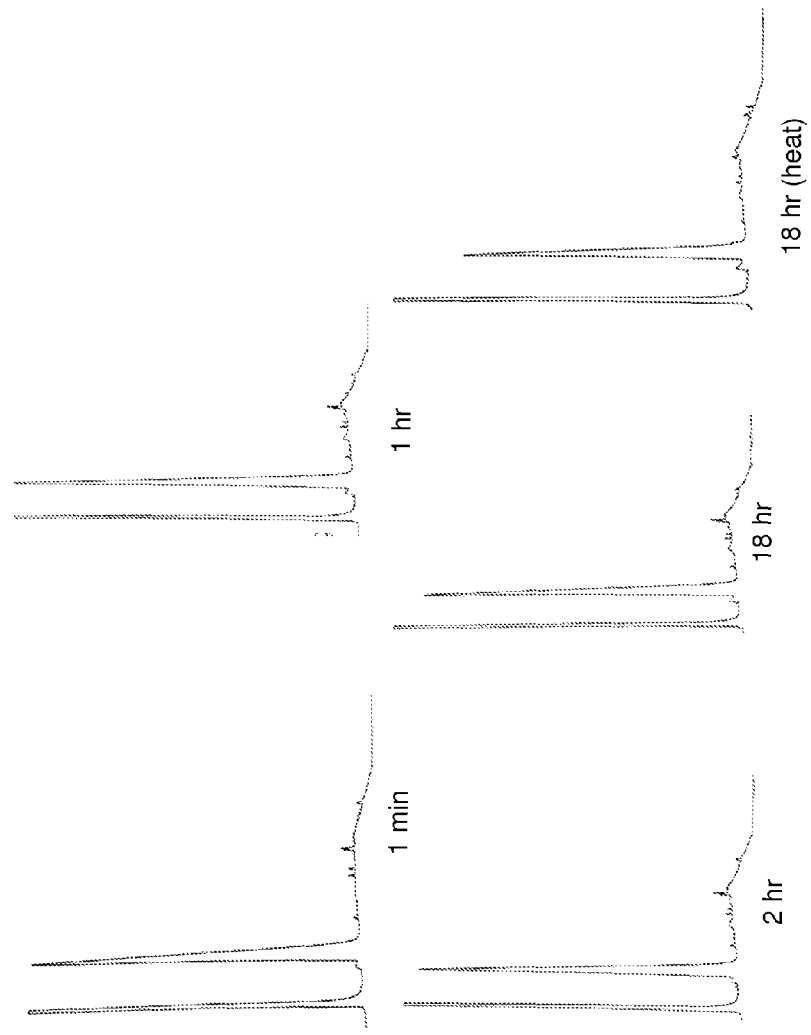

FIG. 7 HPLC profiles of esterification products of E4A with Cinnamoyl chloride (J) from different times of esterification reaction. Reaction products obtained from each time of reaction (1 min, 1 hour, 2 hours, 18 hours, 18 hours (heat)) were fractionated by HPLC. The profile is plotted according to HPLC elution time and optical density of fractions. Reaction was performed at Room temperature and 75 C.

Figure 8:
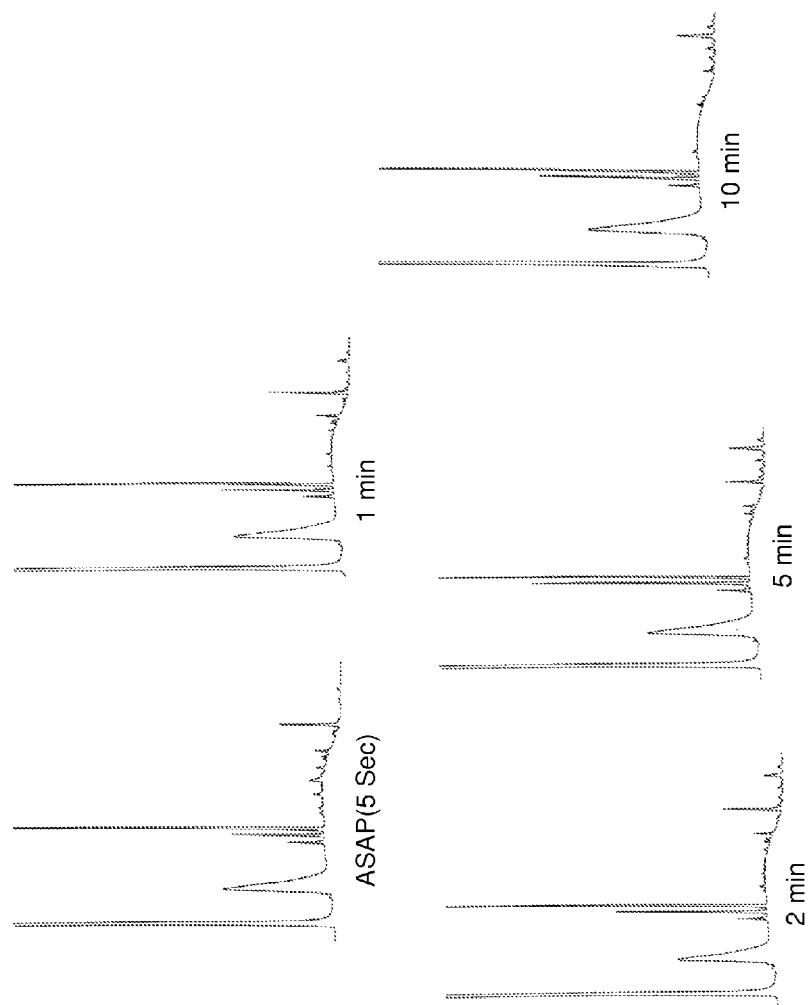

FIG. 8 HPLC profiles of esterification products of E4A with Benzoyl chloride (K) from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at 0 C.

Figure 9:
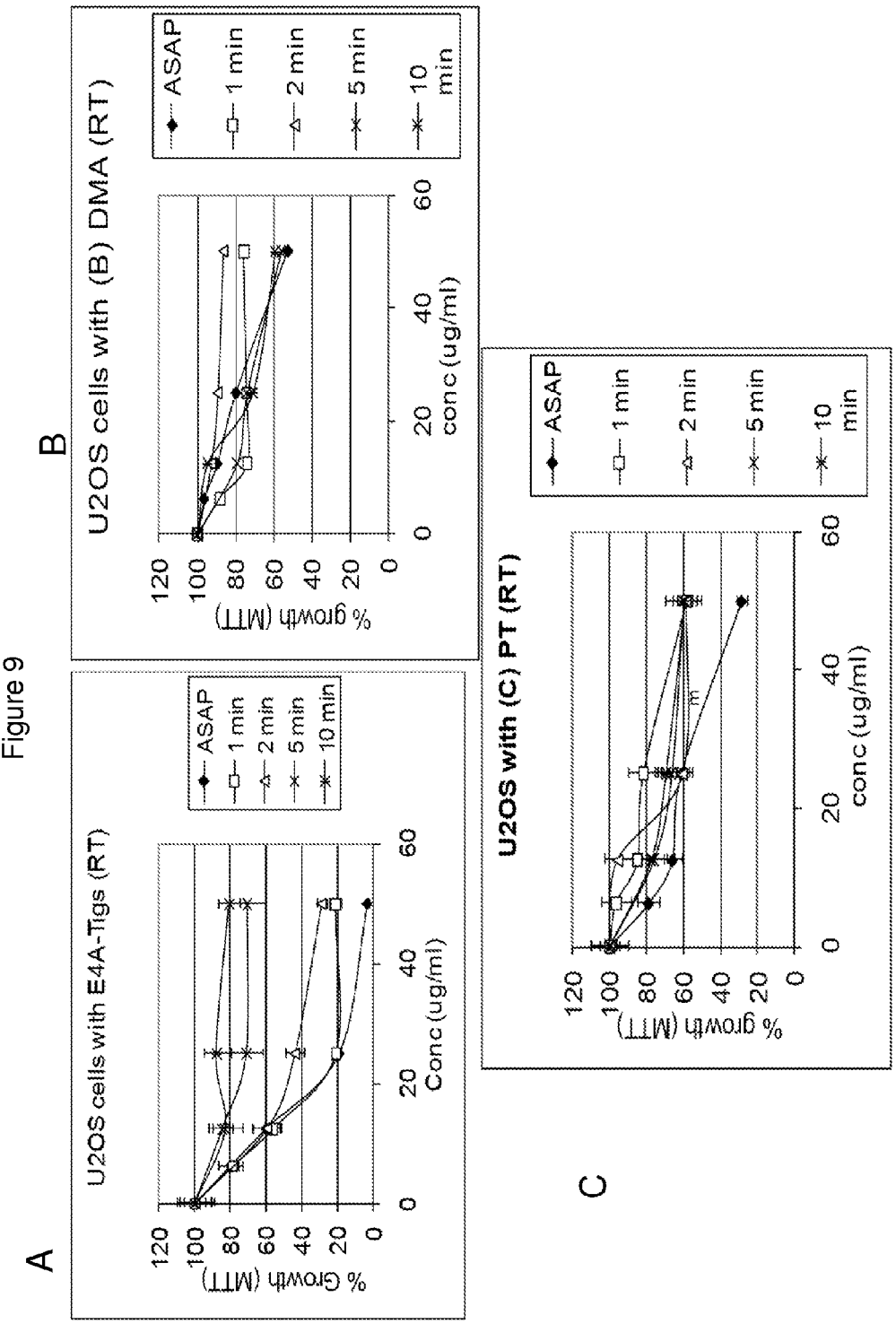

FIG. 9 MTT cytotoxic activity of times study at room temperature for A: E4A-Tigloyl; B: E4A-3,3-dimethylacryloly; C: E4A-4-pentenoyl.

Figure 10:
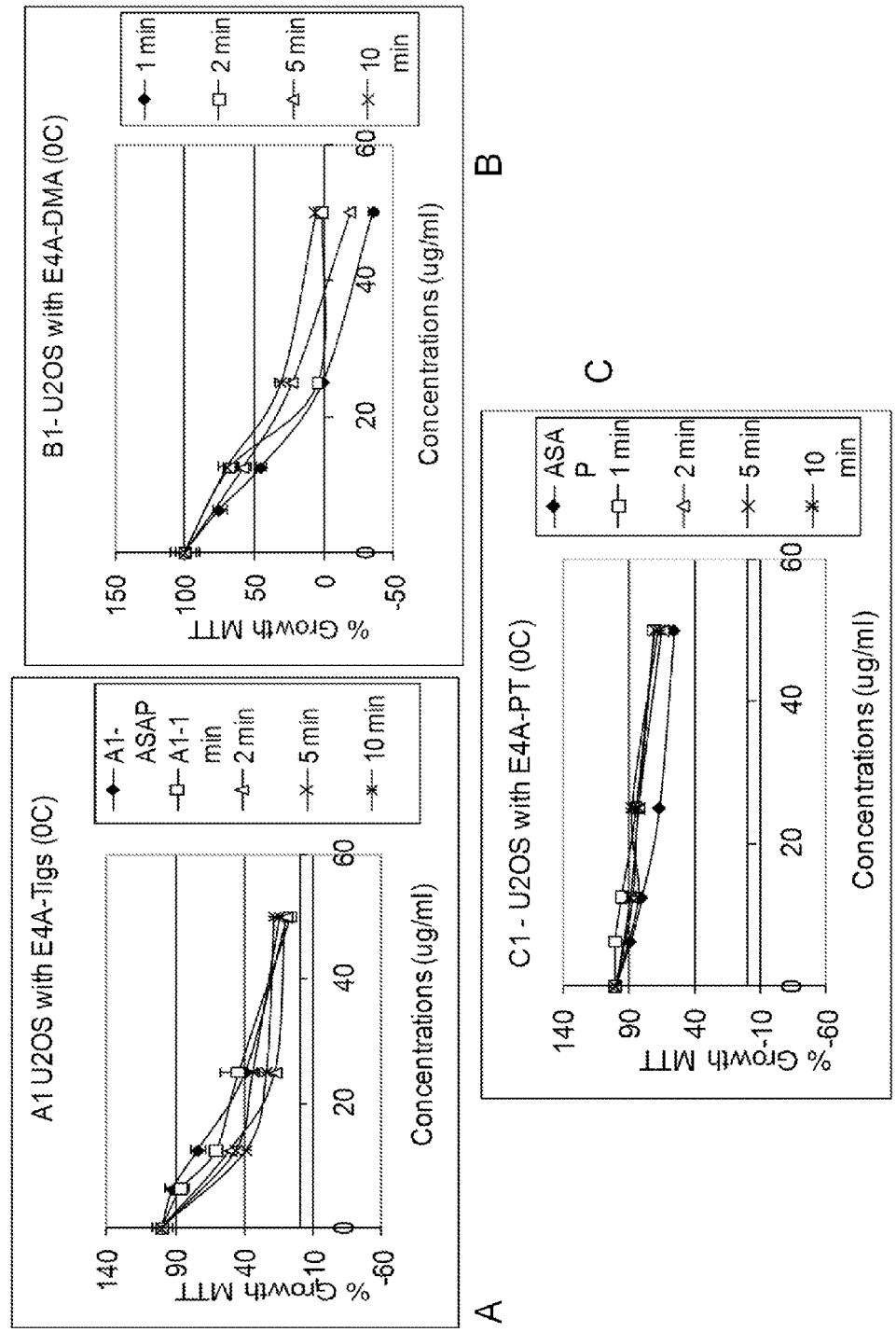

FIG. 10 MTT cytotoxic activity of times study at 0 C for A: E4A-Tigloyl; B: E4A-3,3-dimethylacryloly; C: E4A-4-pentenoyl.

Figure 11:
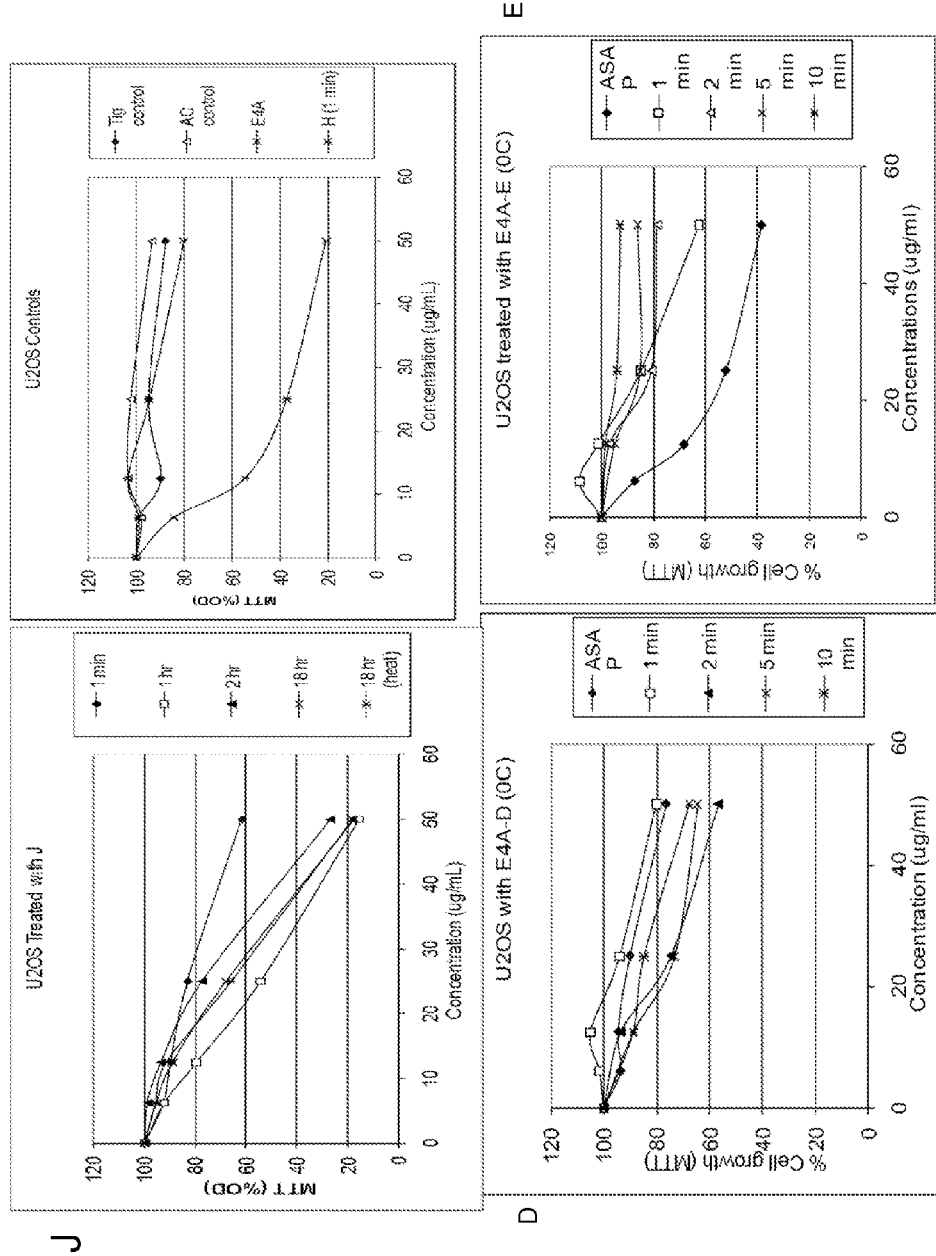

FIG. 11 MTT cytotoxic activity of times study for J: E4A-cinnamoyl; D: E4A-hexanoyl; E: E4A-2-ethylbutyryl; and controls: Tig control is tigloyl chloride without E4A; AC control is acetyl chloride without E4A; H is acetyl chloride with E4A reaction 1 min.

Figure 12:
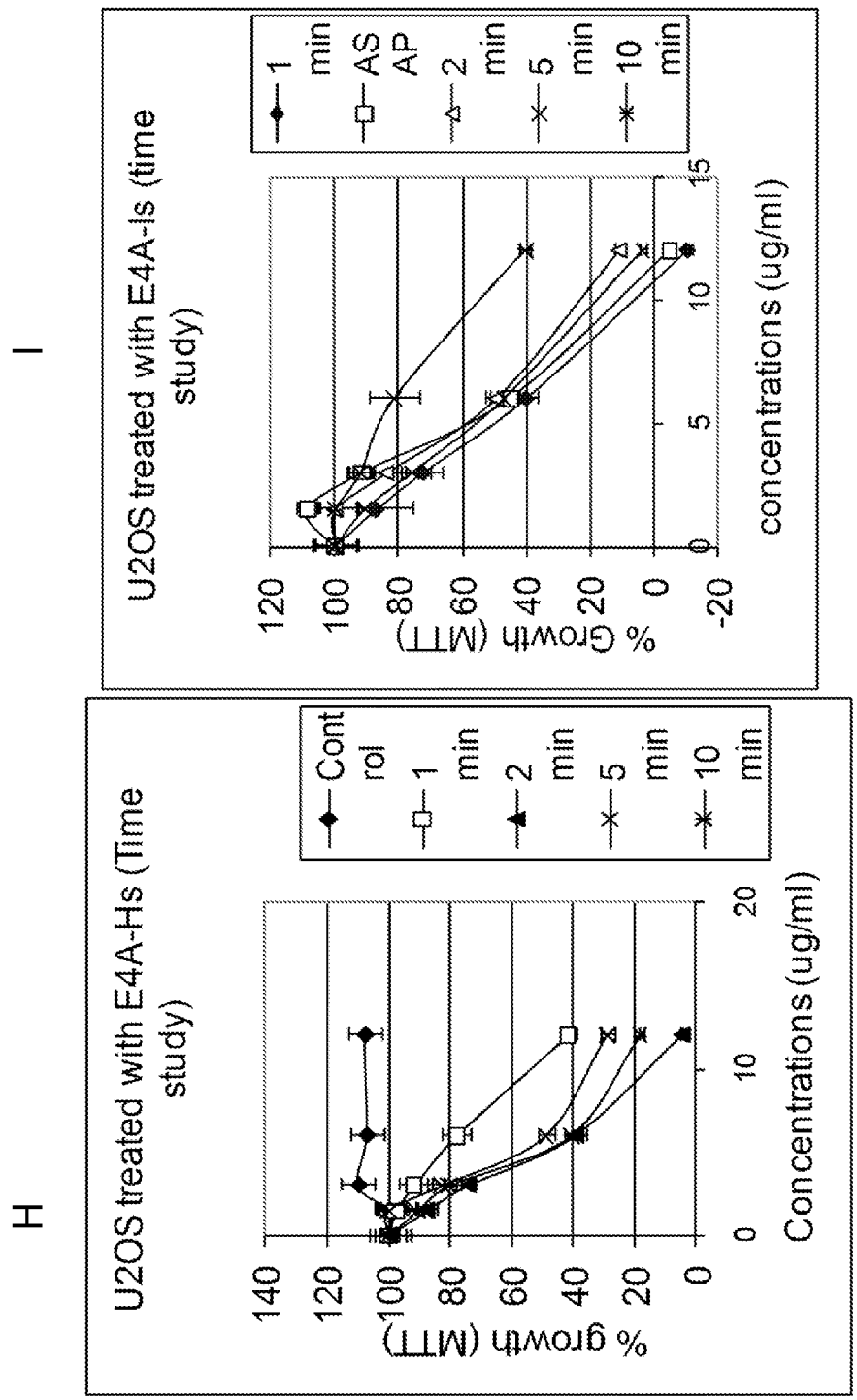
Figure 13:
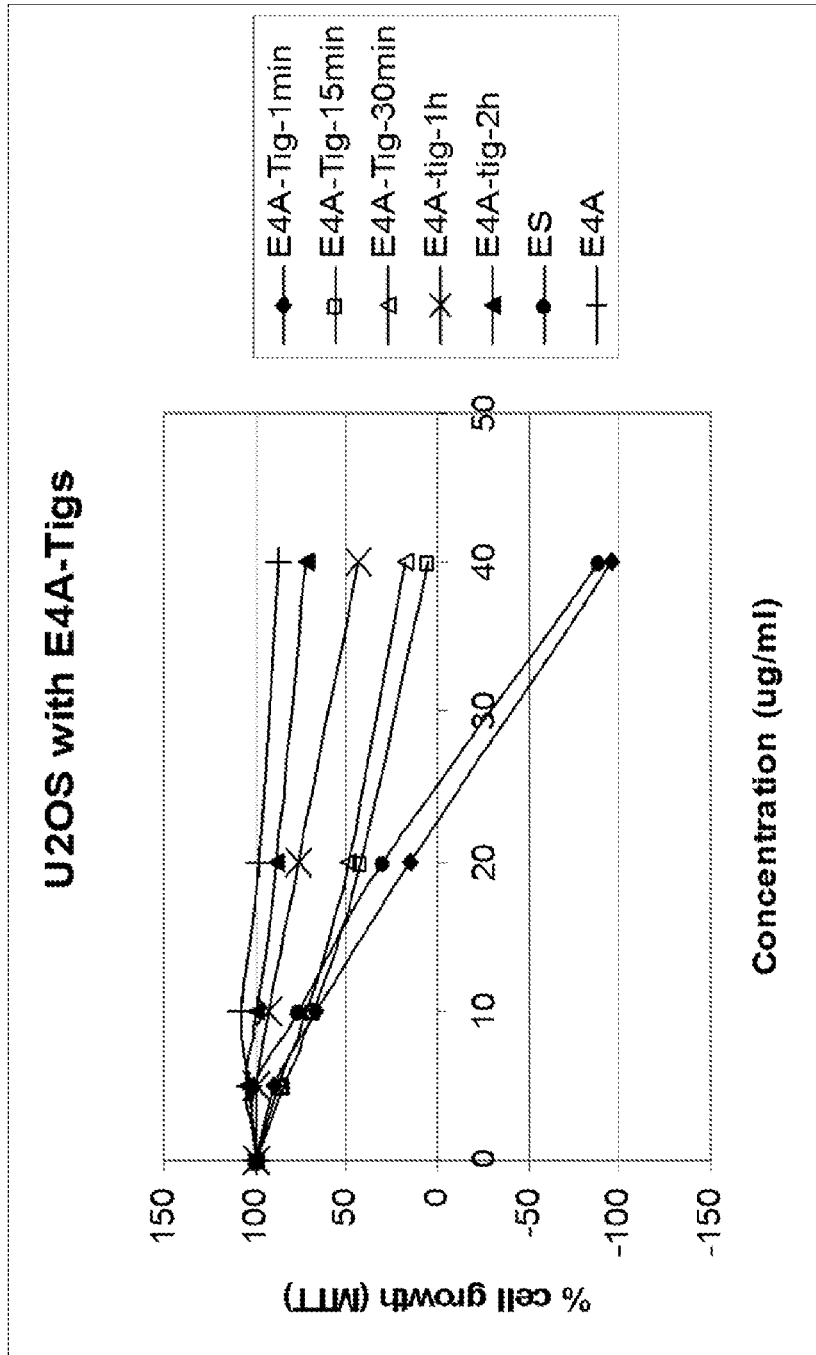
Figure 14:
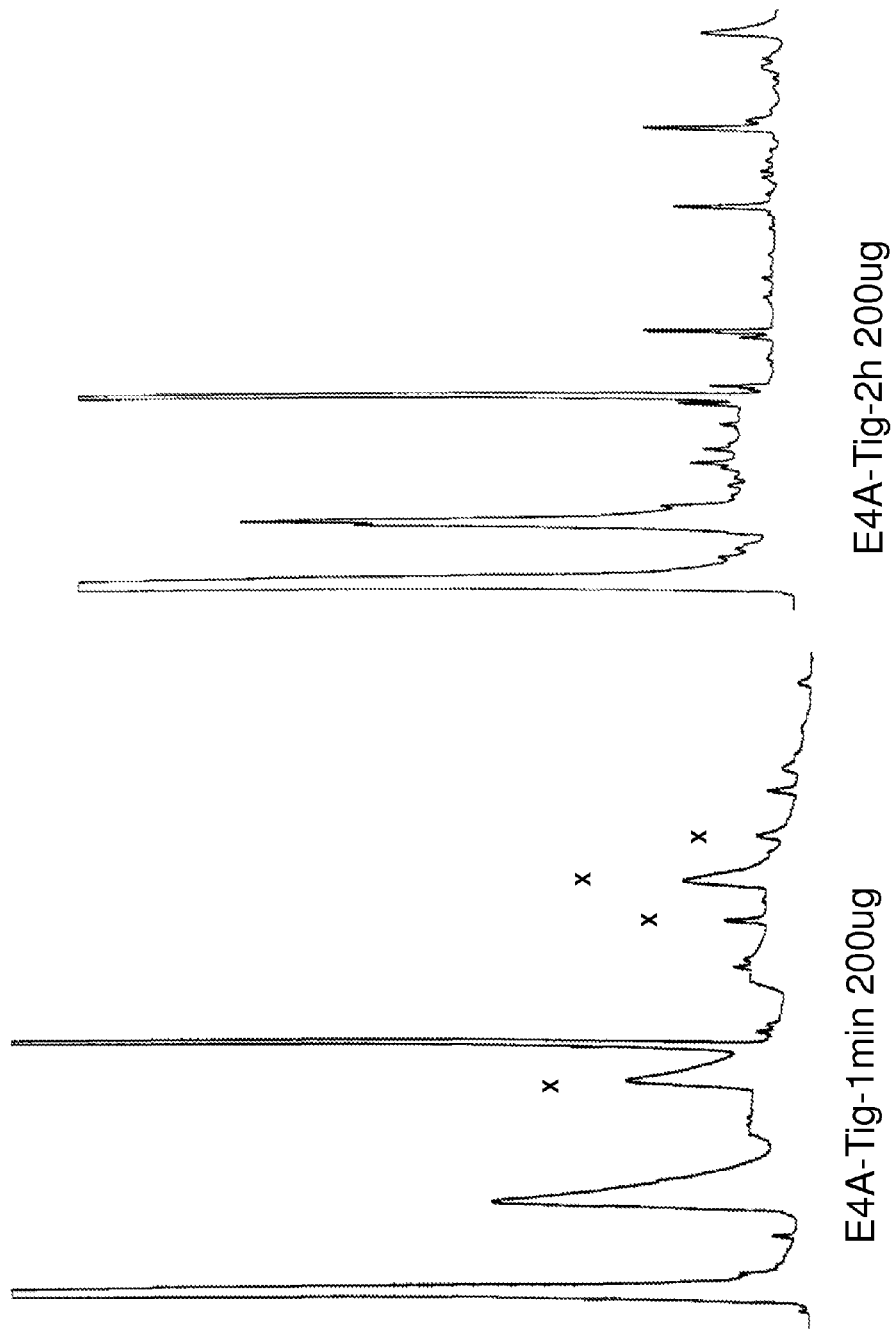
Figure 15:
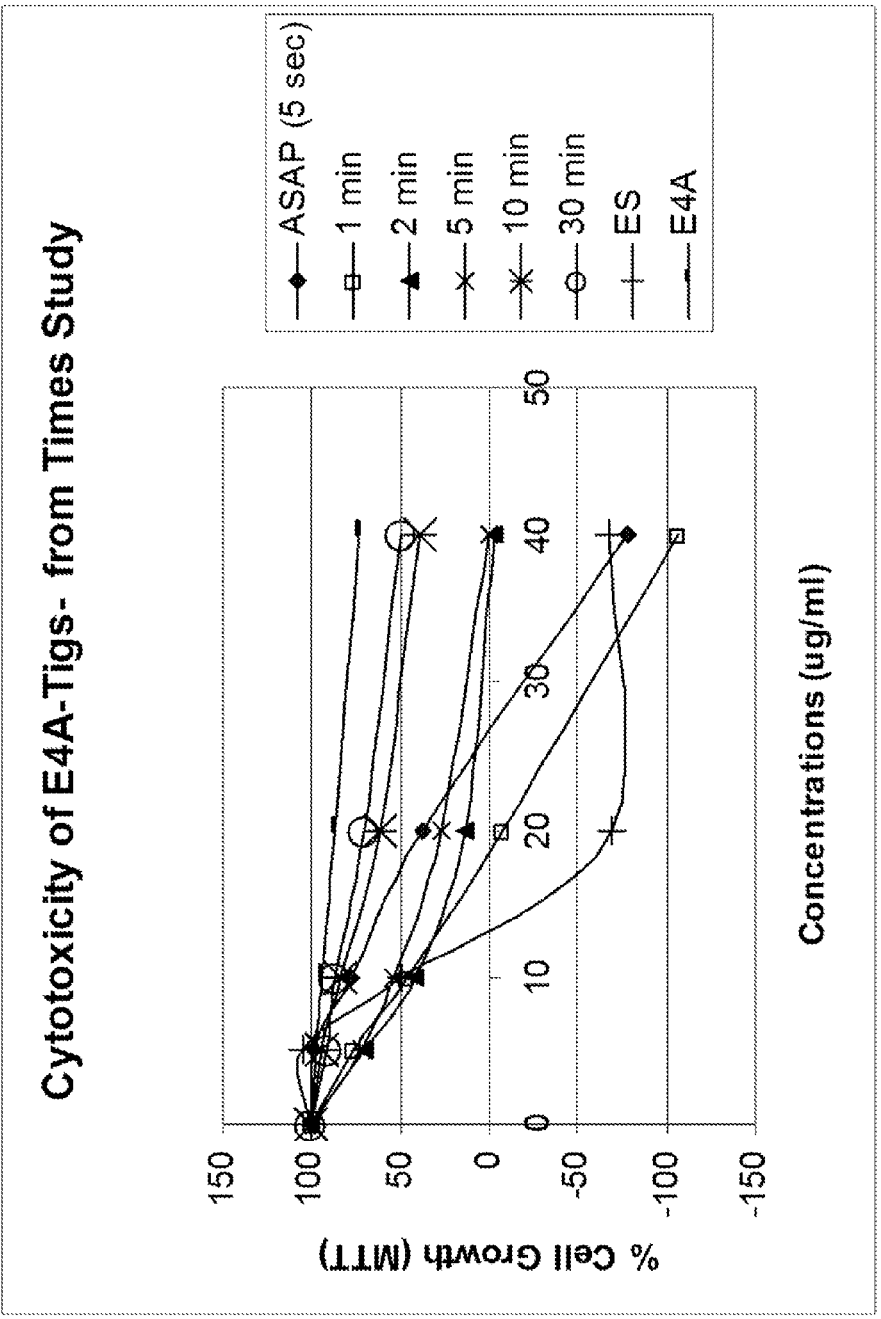

FIG. 12 MTT cytotoxic activity of times study for H: E4A-acetyl; I: E4A-crotonoyl FIG. 13 MTT cytotoxic activity of times study for E4A-Tig in 1 min, 15 min, 30 min, 1 hour, 2 hours FIG. 14 HPLC profiles of E4A-Tig in 1 min and 2 hours FIG. 15 MTT cytotoxic activity of times study for E4A-Tig. Results: E4A-Tigs from reaction of 5 sec to 1 min are most active. Activity decrease after 1 min of reaction. Minimum to no activity was obtained at 10 minutes or longer.

Figure 16:
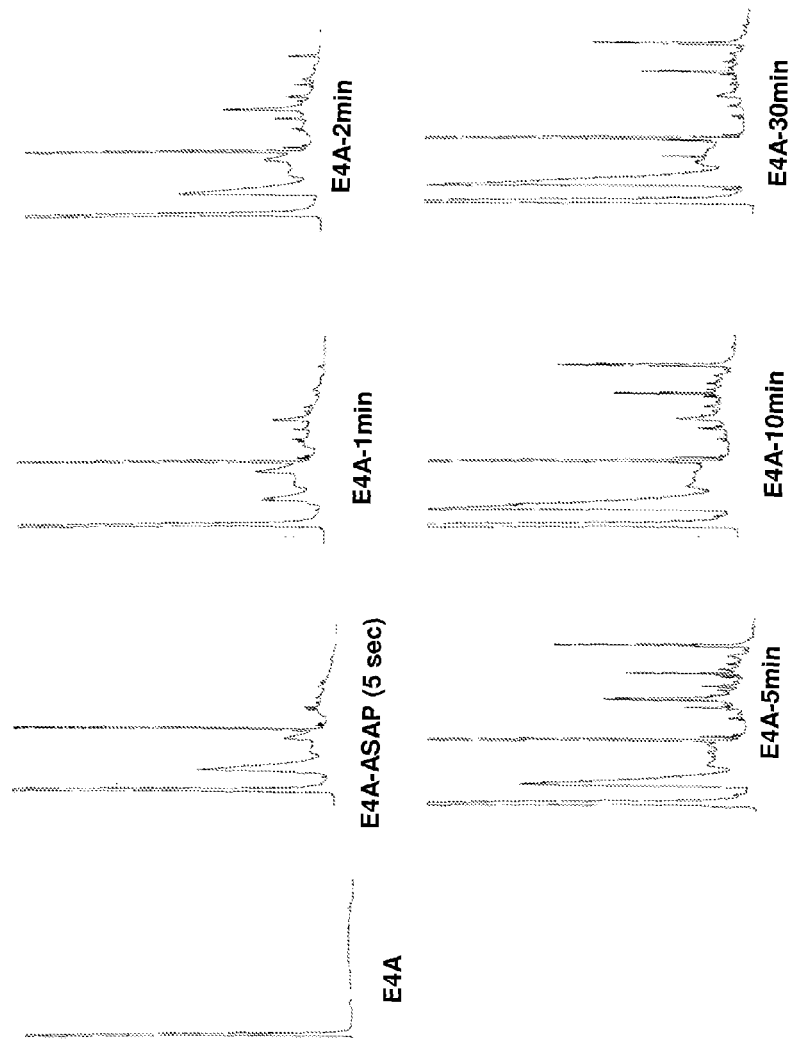

FIG. 16 Results of HPLC profiles of E4A-Tigs: E4A, E4A-ASAP (5 sec), E4A-1 min, E4A-2 min, E4A-5 min, E4A-10 min, E4A-30 min.

Figure 17:
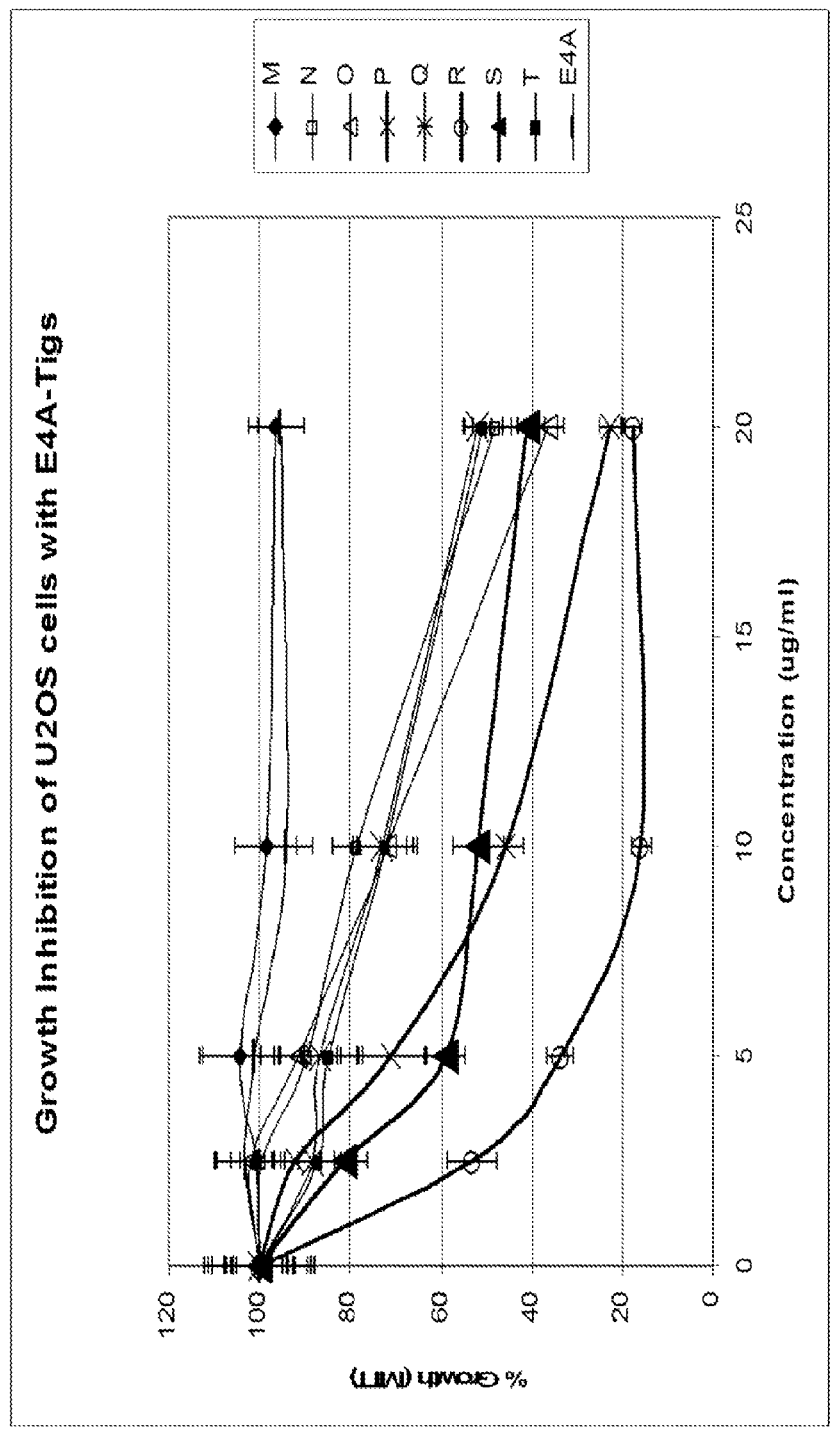

FIG. 17 Results of Activity order: M, N, O, P, Q, R, S, T, E4A; M=E4A has no activity.

Figure 18:
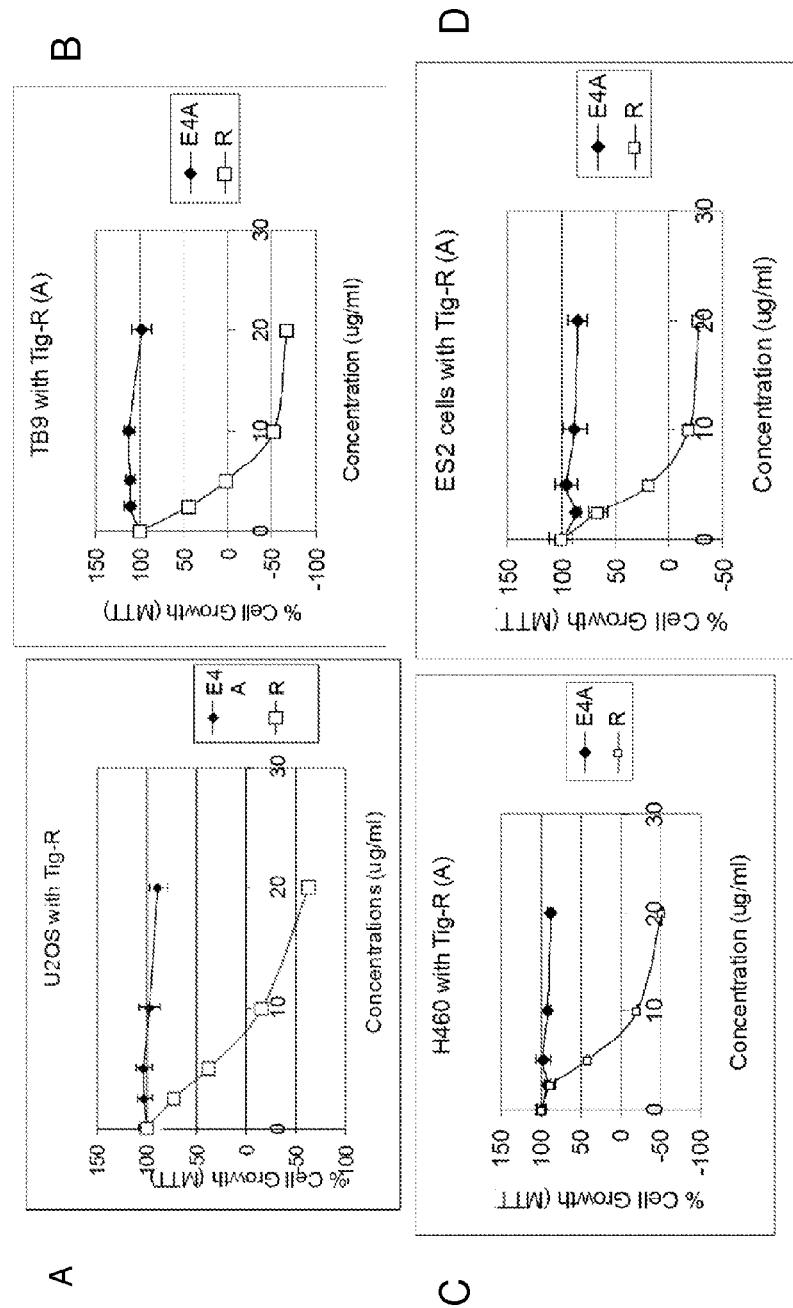
Figure 19:
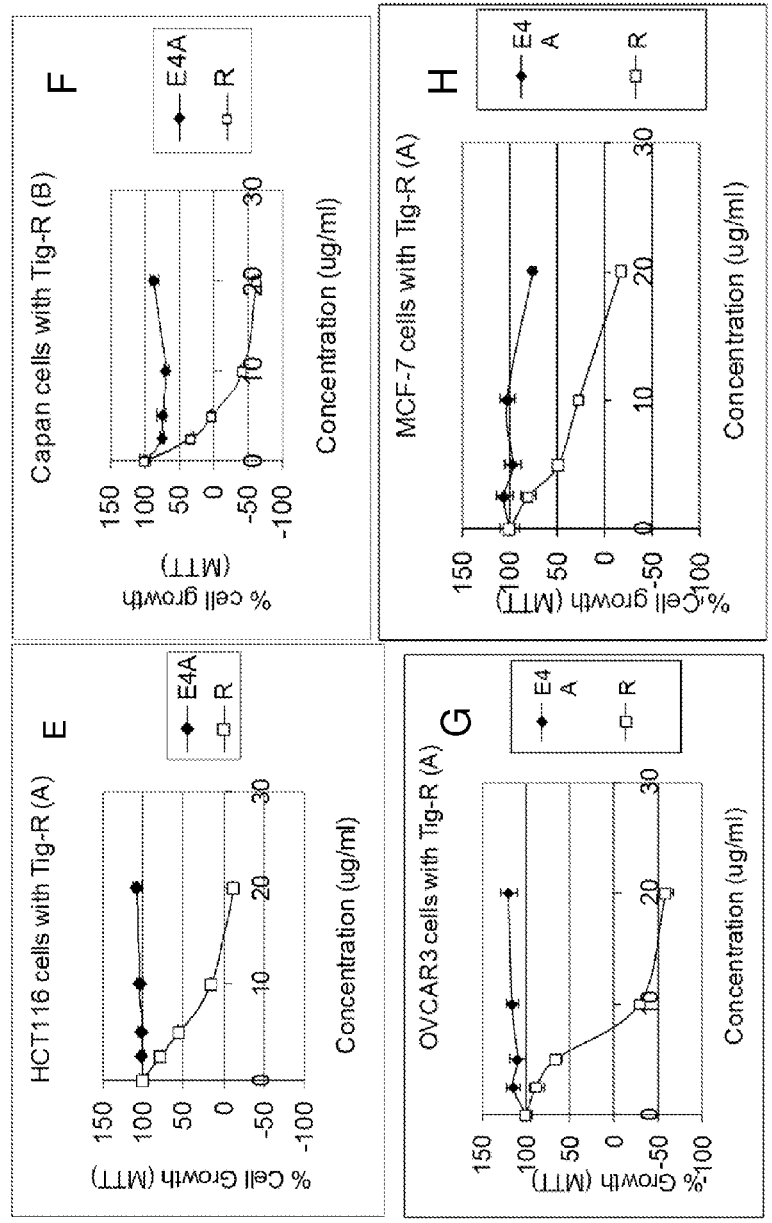
Figure 20:
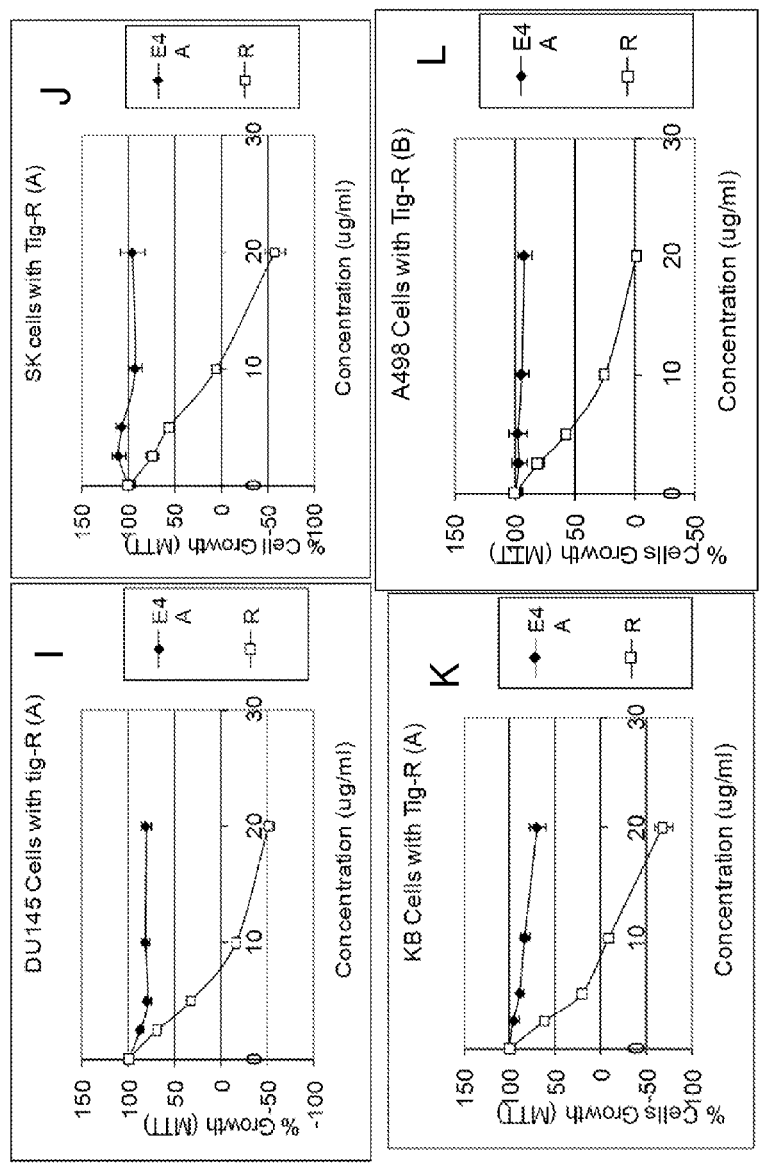
Figure 21:
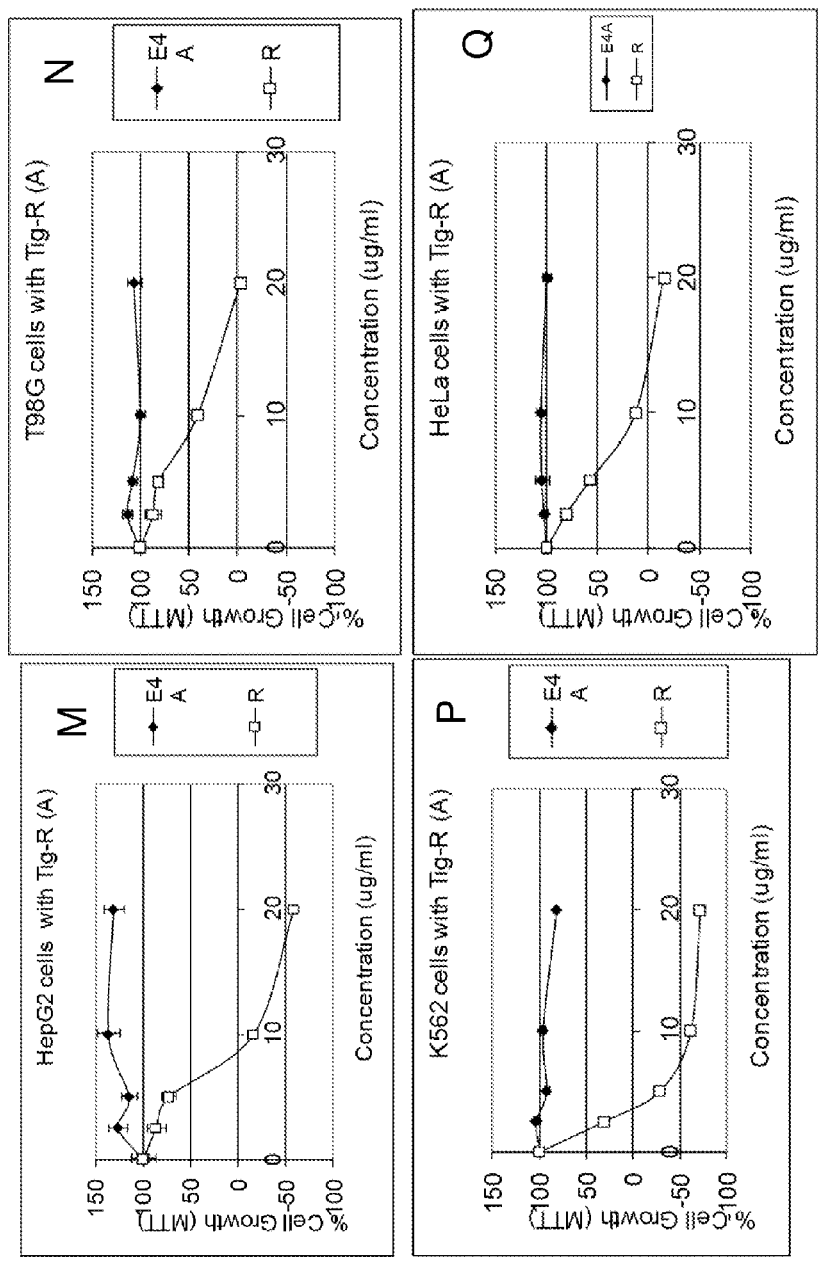
Figure 22:
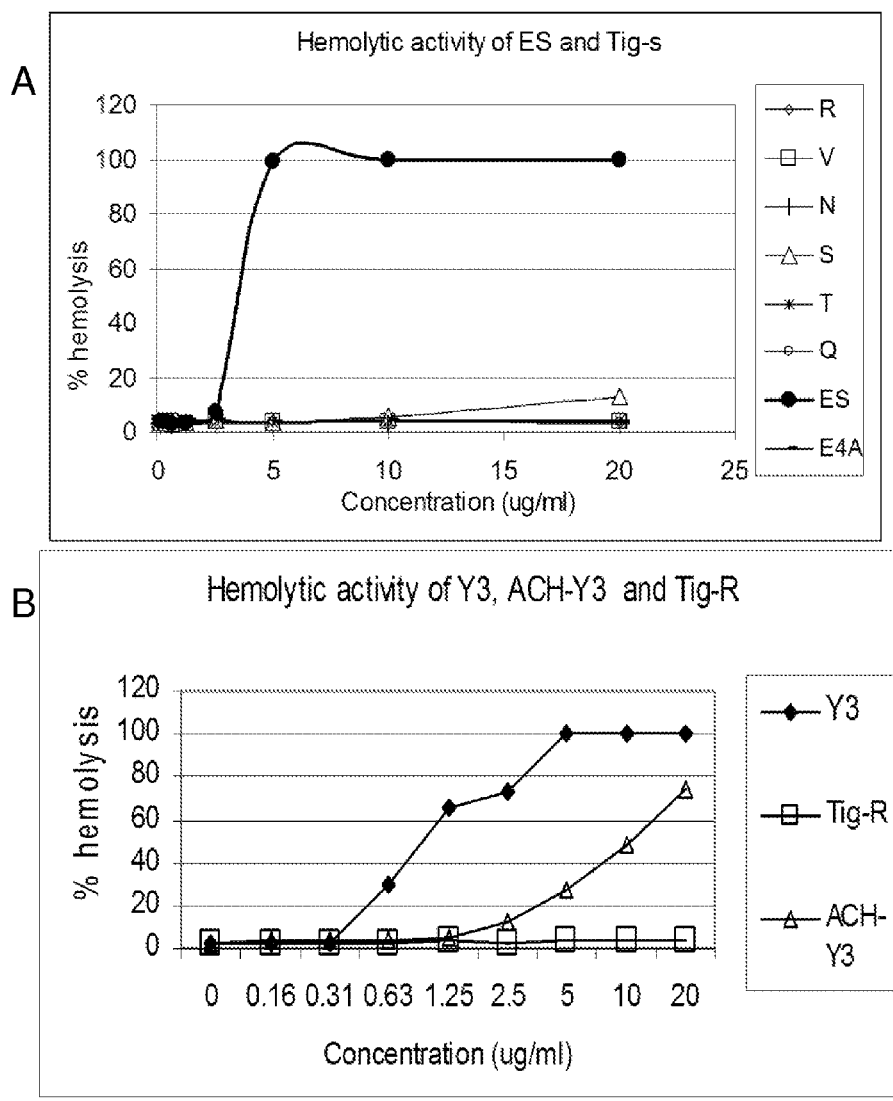
Figure 23:
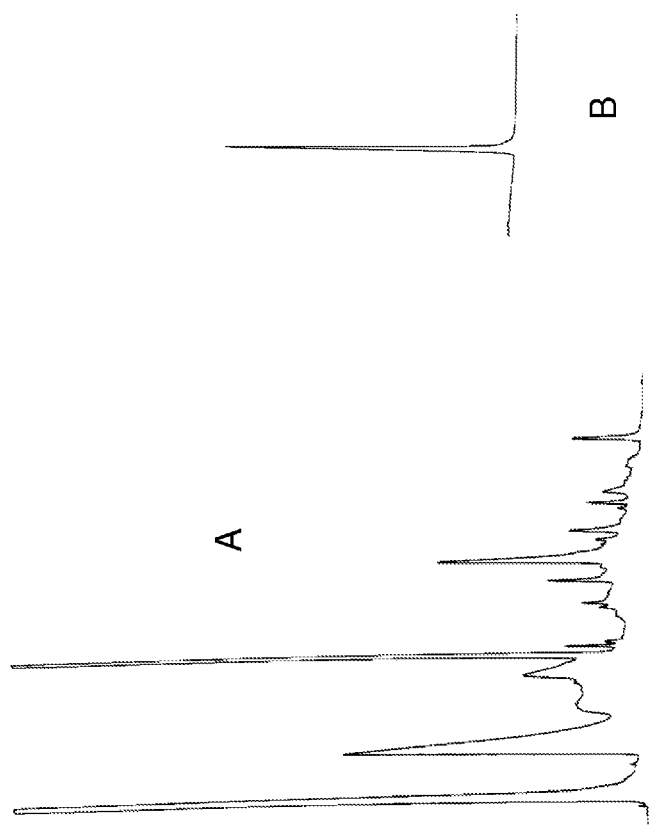

FIG. 18 Results of MTT cytotoxic activity of E4A-Tig-R in Cancer cells of different organs: A, Bone (U2OS) IC50=4.5 ug/ml; B, Bladder (TB9): IC50=2.5 ug/ml; C, Lung (H460): IC50=4.8 ug/ml; D, Ovary (ES2): IC50=2.8 ug/ml FIG. 19 Results of MTT cytotoxic activity of E4A-Tig-R in Cancer cells of different organs: E, Colon (HCT116) IC50=5.2 ug/ml; F, Pancreas (Capan) IC50=2.4 ug/ml; G, Ovary (OVCAR3) IC50=5.8 ug/ml; H, Breast (MCF-7) IC50=4.5 ug/ml FIG. 20 Results of MTT cytotoxic activity of E4A-Tig-R in Cancer cells of different organs: I, Prostate (DU145) IC50=3.6 ug/ml; J, Skin (SK-MeI-5) IC 50=5.1 ug/ml; K, Mouth (KB) IC 50=3 ug/ml; L, Kidney (A498) IC 50=3.5 ug/ml FIG. 21 Results of MTT cytotoxic activity of E4A-Tig-R in Cancer cells of different organs: M, Liver (HepG2) IC50=6 ug/ml; N, Brain (T98G) IC50=8 ug/ml; P, Leukemia (K562) IC 50=2 ug/ml; Q, Cervix (HeLa) IC 50=5 ug/ml FIG. 22 (A) Results: Tig-N, -Q, -R, -T-S and -V do not have hemolytic activity up to 20 ug/ml. The original compound ES lyse 100% red blood cells (RBC) at 5 ug/ml. (B) Results: compare to Y3, the ACH-Y3 is less potent in hemolytic activity. Tig-R has no hemolytic activity FIG. 23 (A) Results of HPLC profiles of reaction products. Multiple fractions were obtained. Individual fractions were collected for further studies.

(B) Results of purification of E4A-Tig-R.

Figure 24:
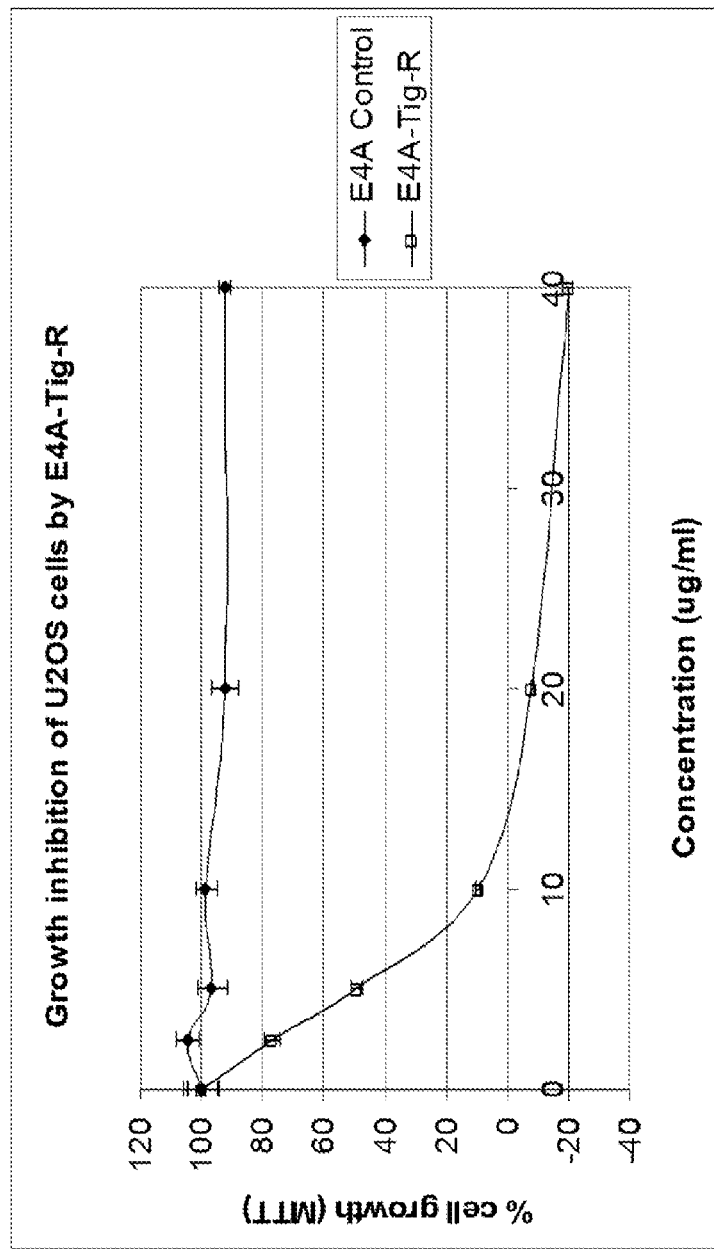

FIG. 24 Results of MTT assay of E4A-Tig-R with bone U2OS cell

Figure 25:
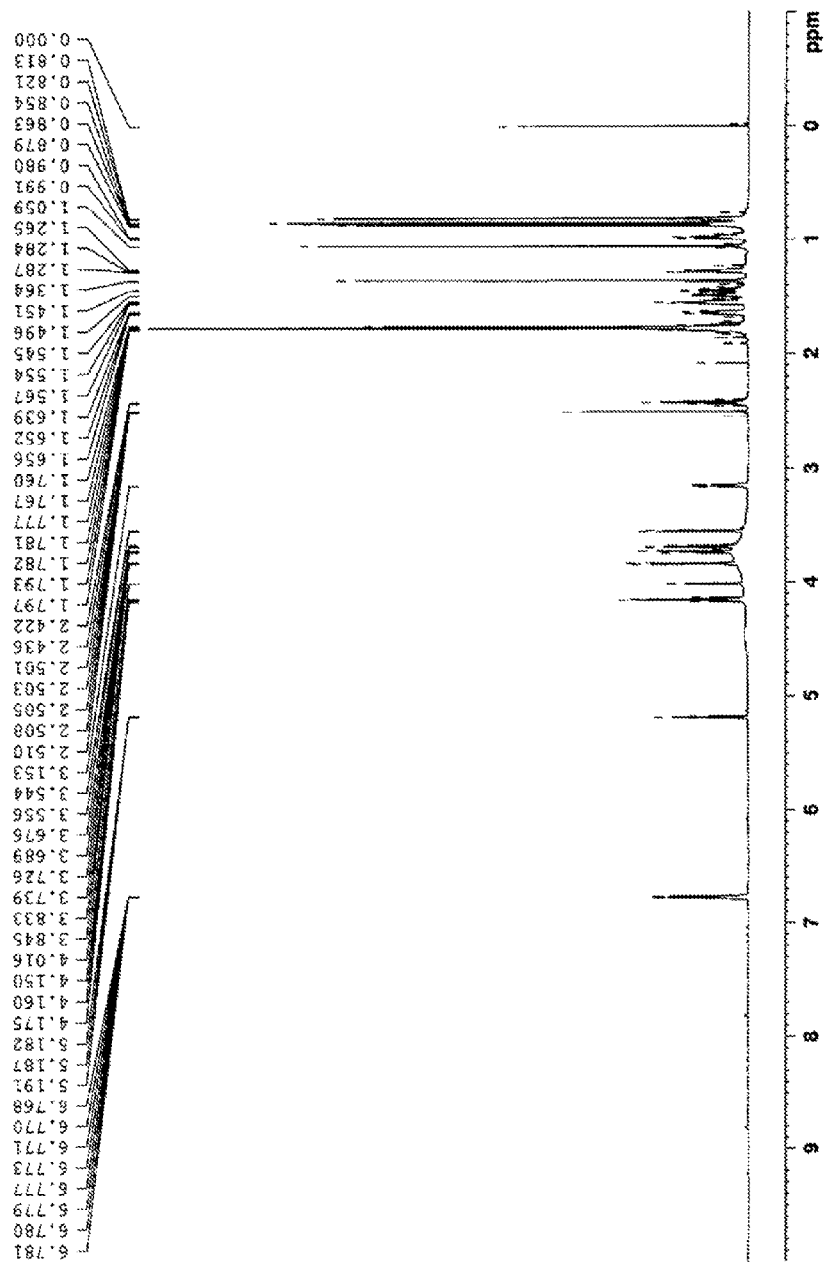

FIG. 25 Results of HNMR of E4A-Tig-R.

Figure 26:
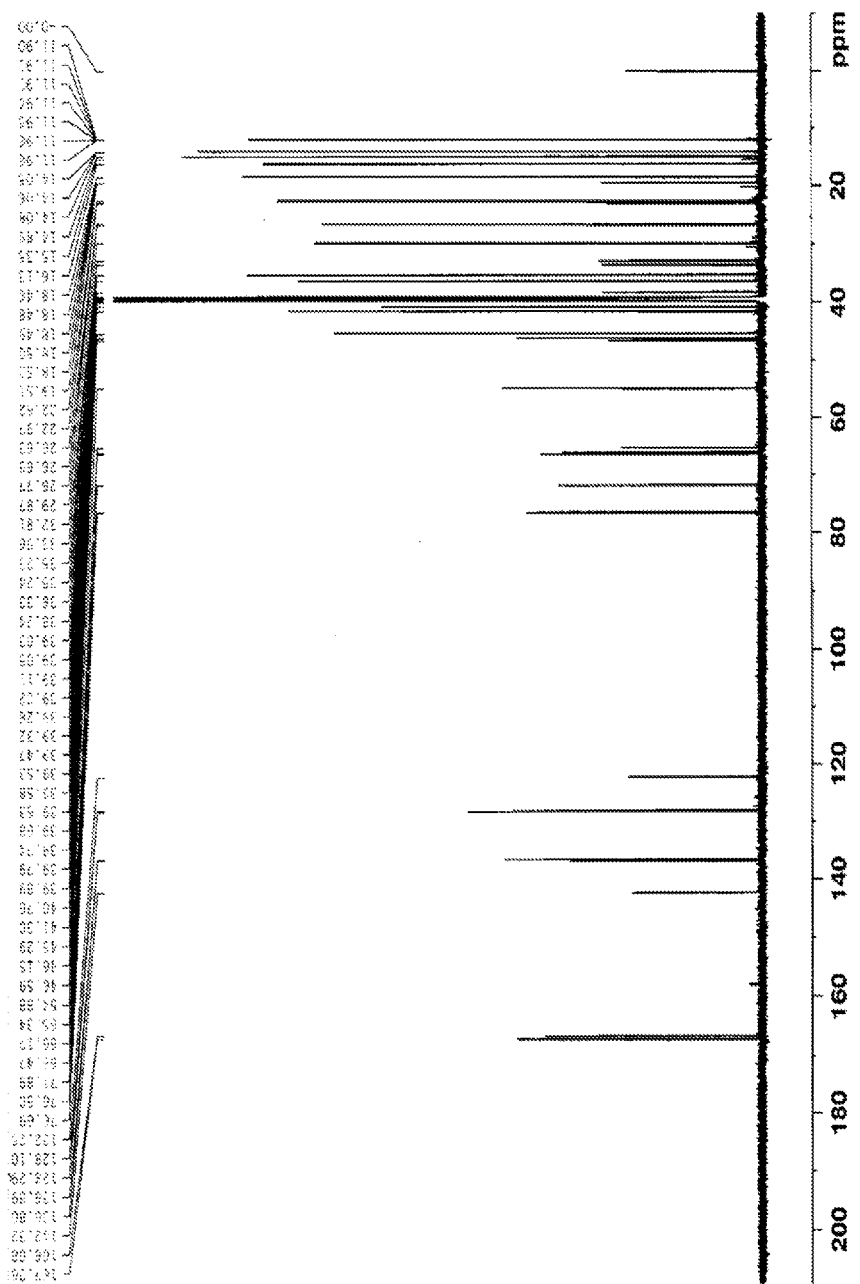

FIG. 26 Results of CNMR of E4A-Tig-R.

Figure 27:
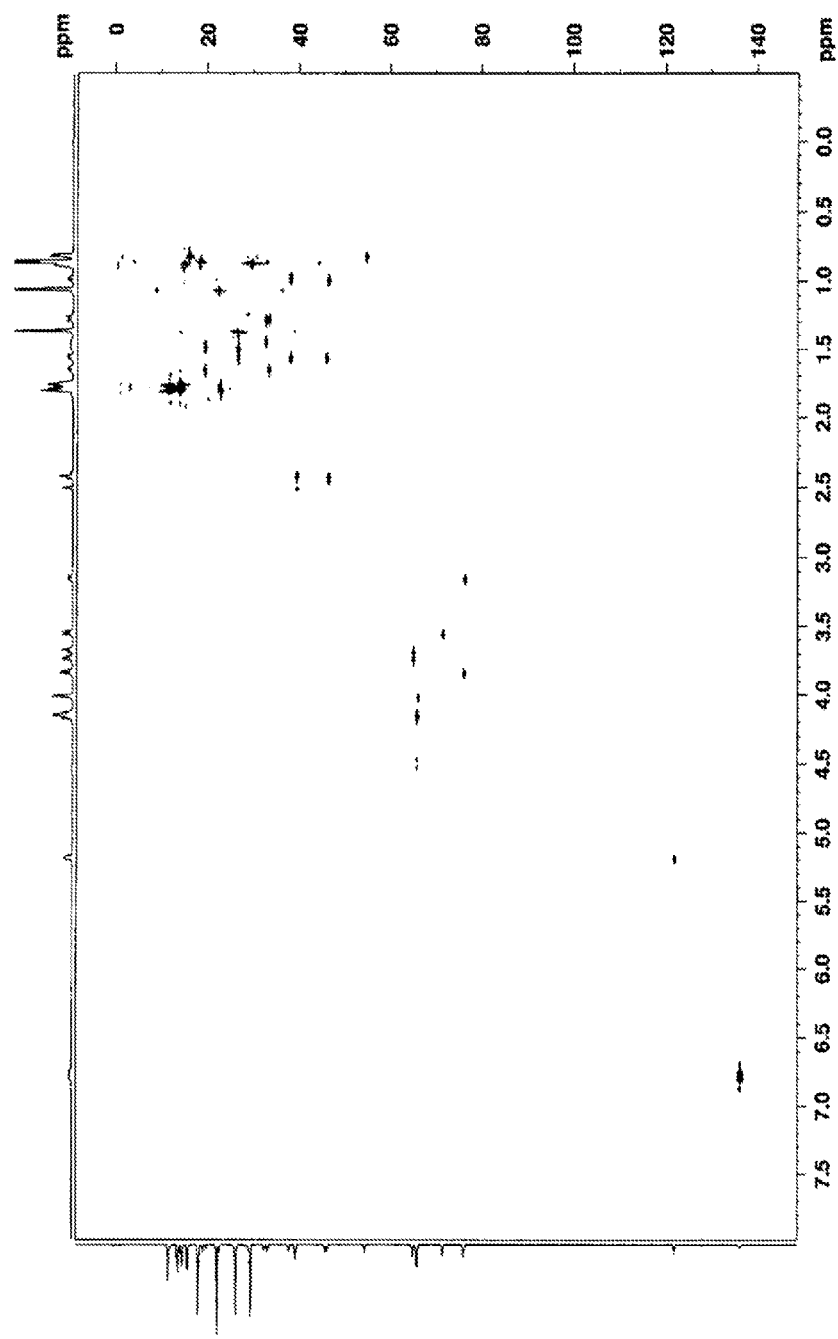

FIG. 27 Results of HMQC of E4A-Tig-R.

Figure 28:
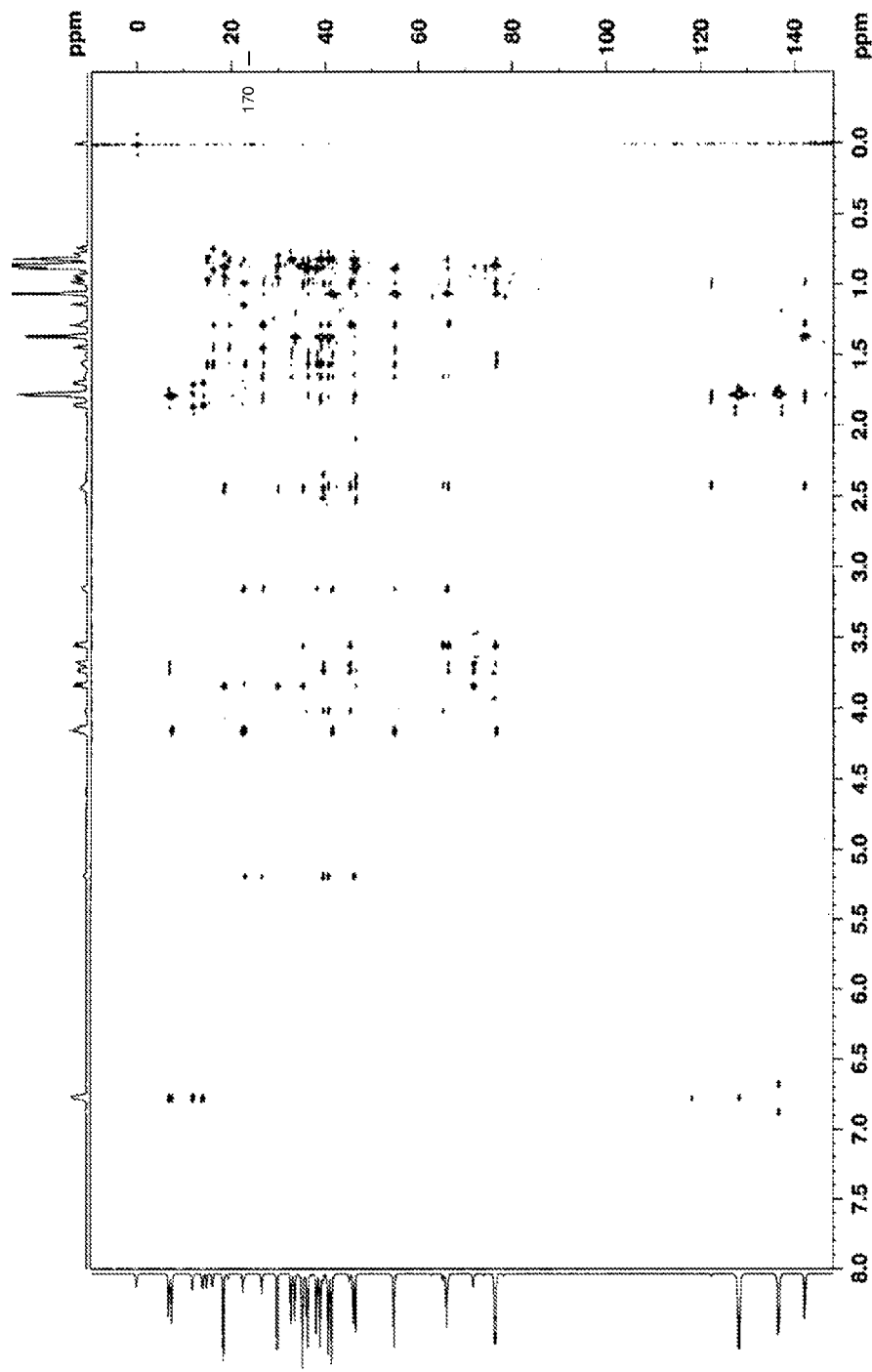

FIG. 28 Results of HMBC of E4A-Tig-R.

Figure 29:
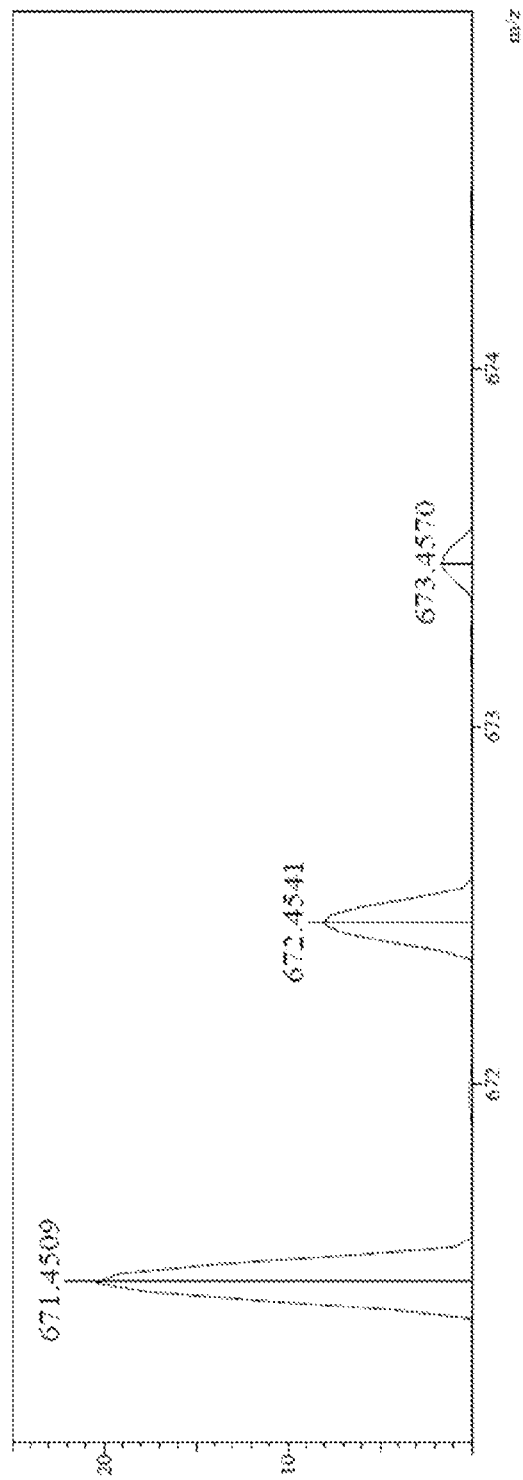
Figure 30:
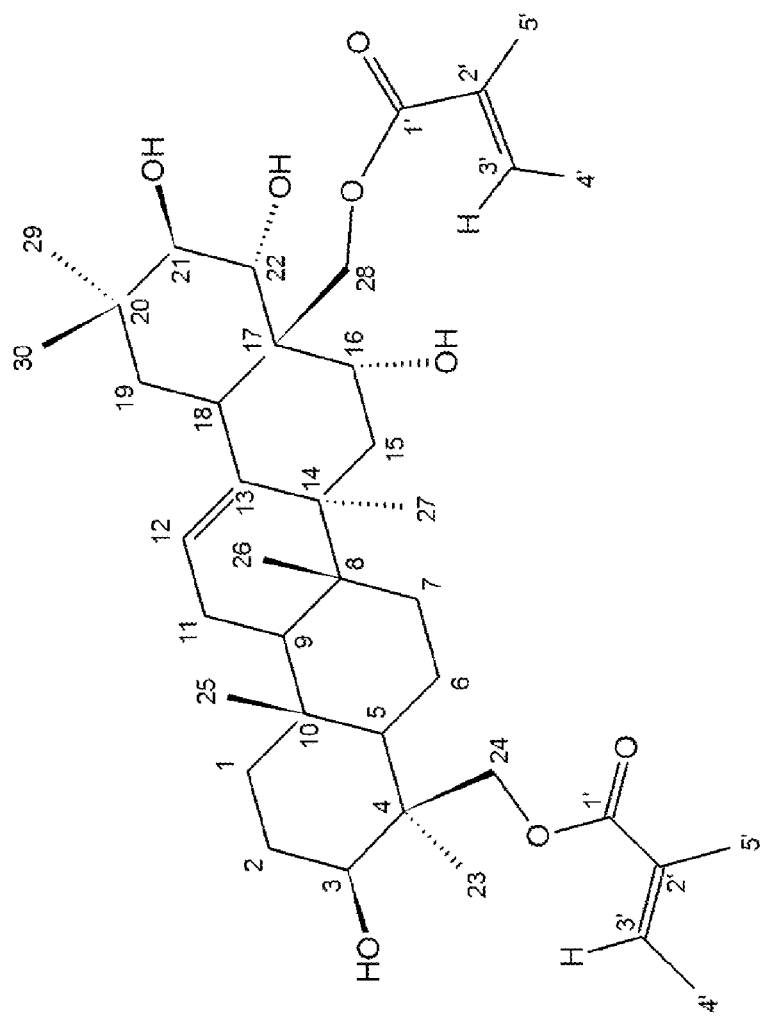

FIG. 29 The Mass spectrum of Tig-R (M+H) is 671.4509. The mass is consistent with the proposed structure FIG. 30 The Chemical Structure of E4A-Tig-R, 24,28-O-Tigloyl-3β,16α,21β,22α,24β,28-hexahydroxyolean-12-ene, Formular:C40H62O8, FW: 670.91548

Figure 31:
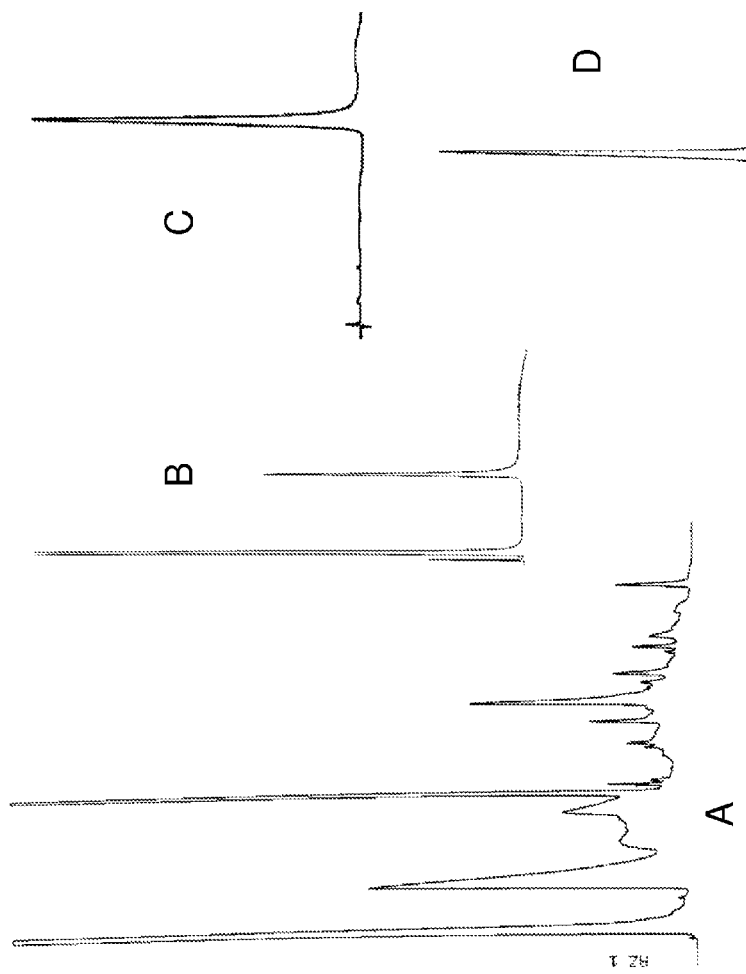

FIG. 31 (A) Results of HPLC profiles of reaction products. Multiple fractions were obtained. Individual fractions were collected for further studies.

(B) Results of purification of E4A-Tig-N. (C) Results of purification of E4A-Tig-S; (D) Results of purification of E4A-Tig-T.

Figure 32:
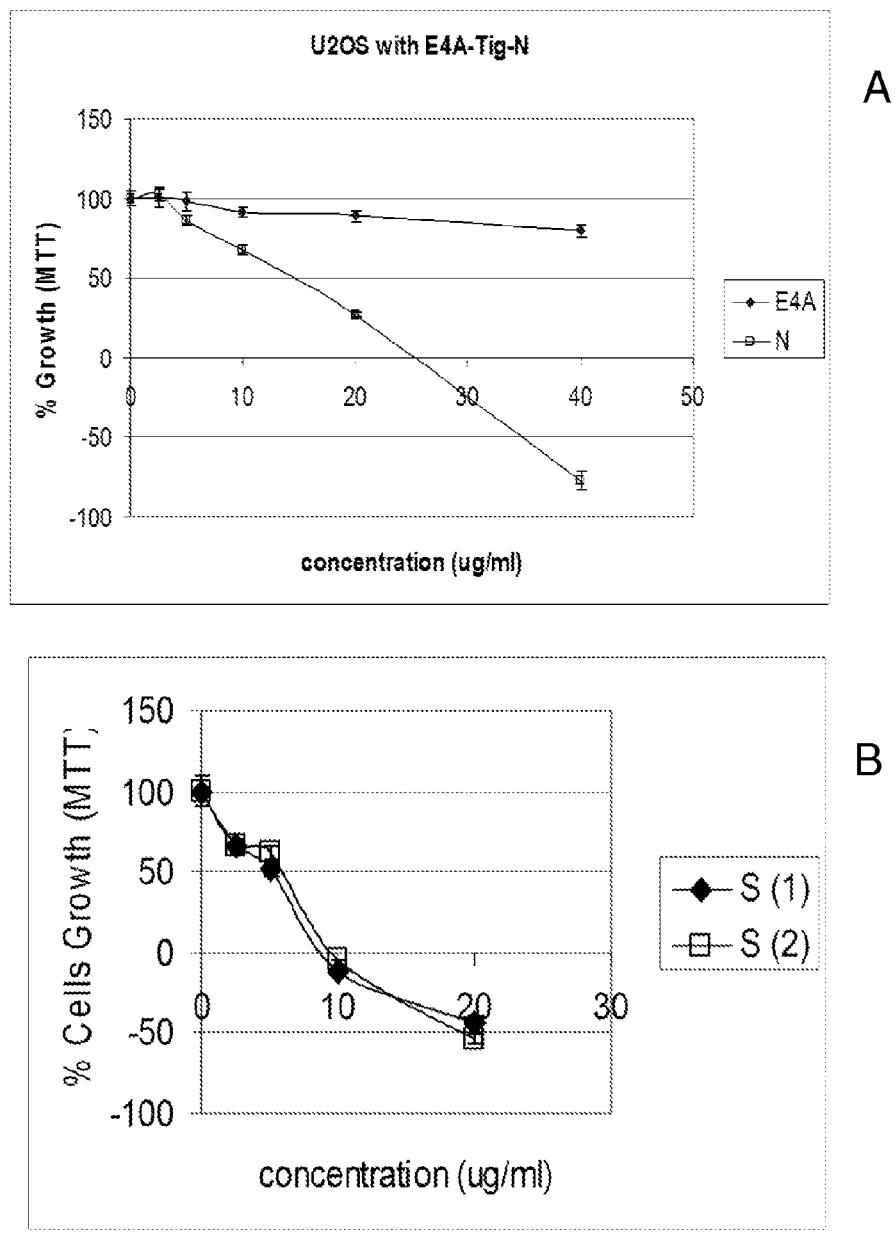
Figure 33:
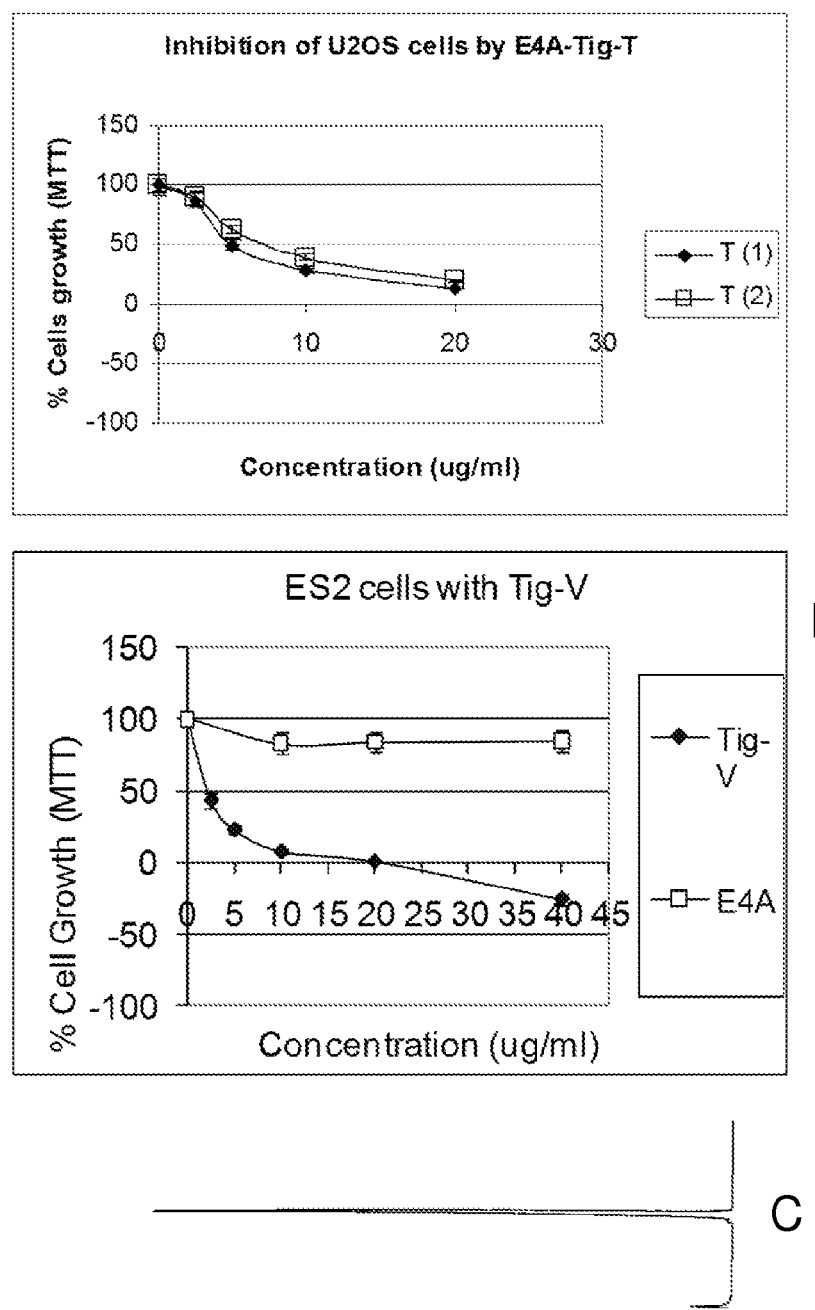

FIG. 32 (A) Results of MTT assay of E4A-Tig-N with bone U2OS cell; (B) Results of MTT assay of E4A-Tig-S with bone U2OS cell FIG. 33 (A) Results of MTT assay of E4A-Tig-T with bone U2OS cell; (B) shows the results of MTT assay of E4A-Tig-V with bone Ovary ES2 cell. IC50=2 ug/ml; (C) shows the results of purification of E4A-Tig-V.

Figure 34:
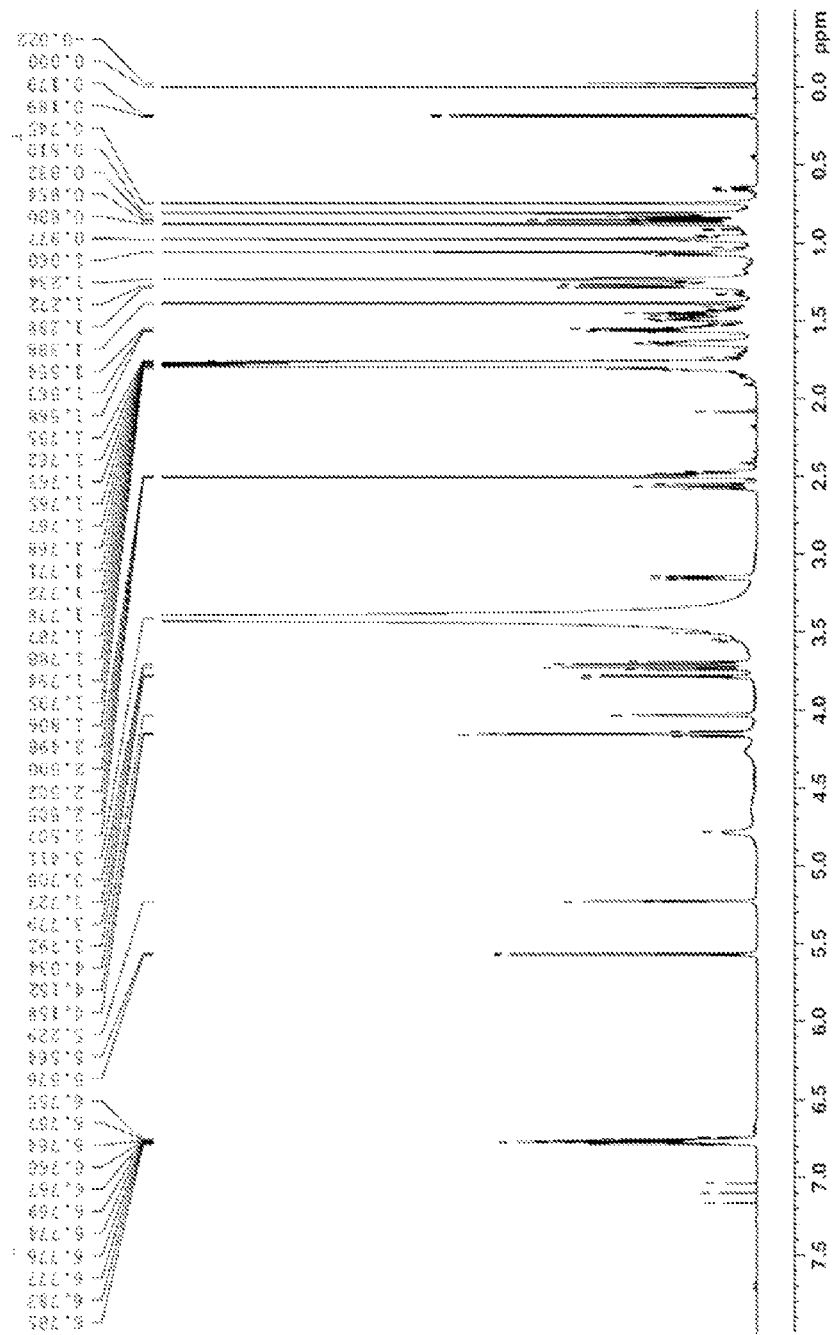

FIG. 34 Results of HNMR of E4A-Tig-V.

Figure 35:
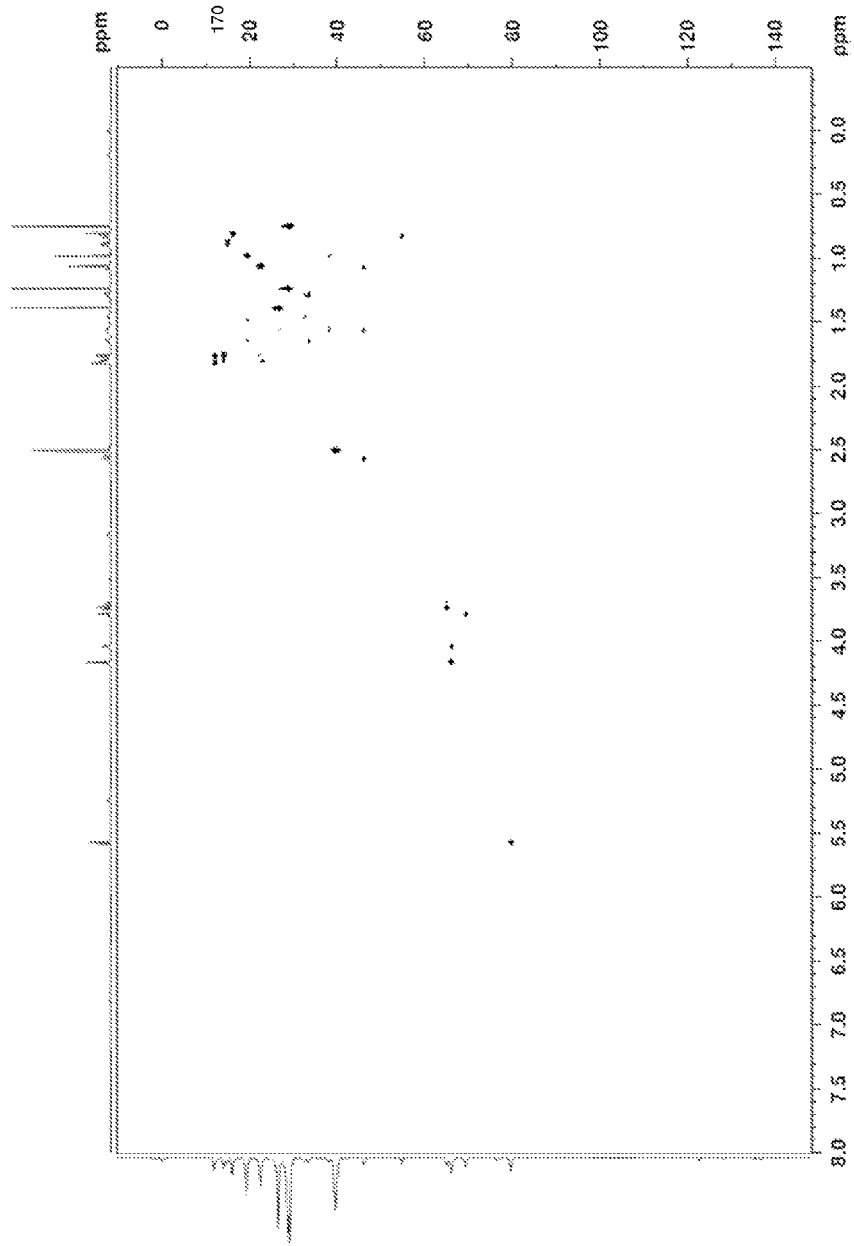

FIG. 35 Results of HMQC of E4A-Tig-V.

Figure 36:
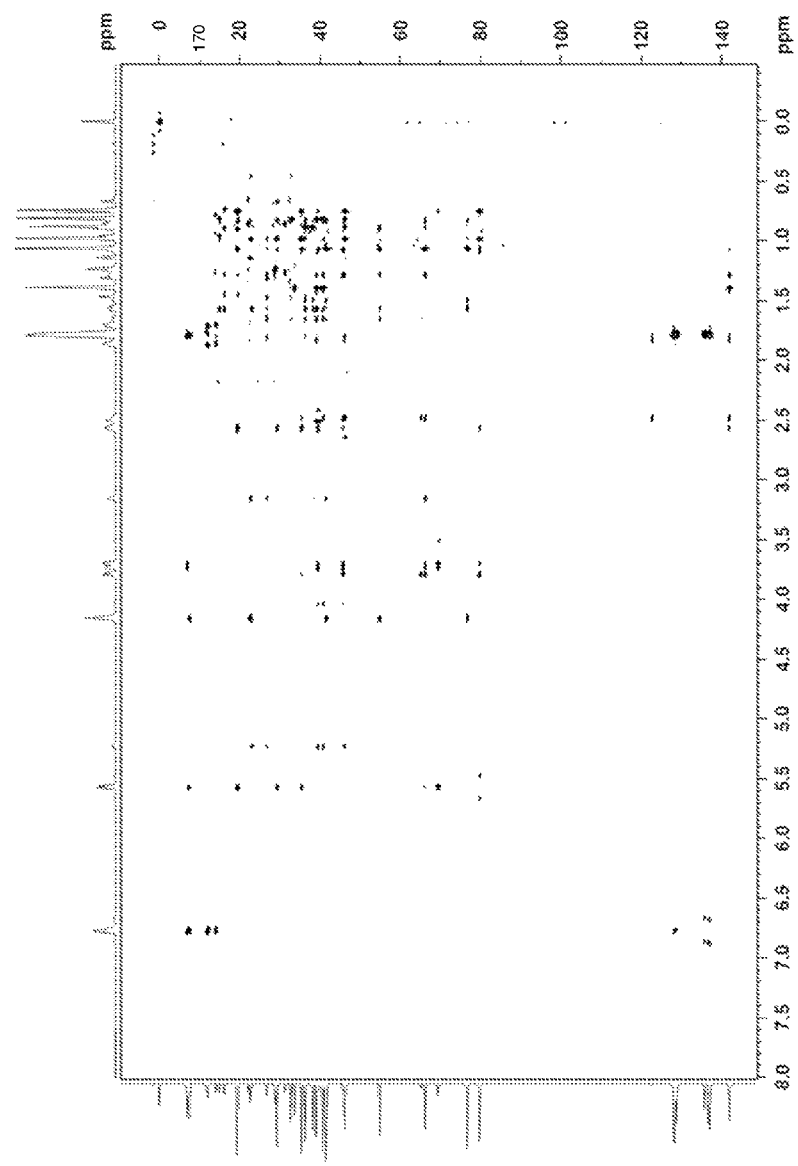

FIG. 36 Results of HMBC of E4A-Tig-V.

Figure 37:
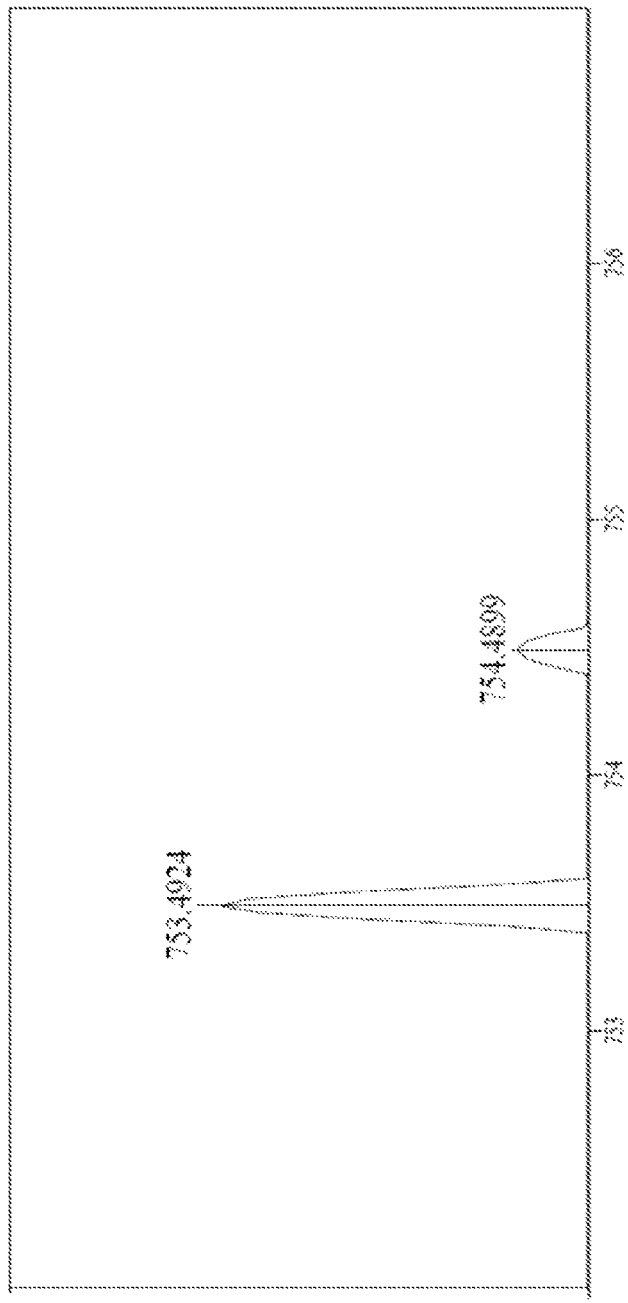

FIG. 37 Results of Mass Spectrum of E4A-Tig-V. The Tig-R (M+H) mass is 753.4924 which is consistent with the proposed formula (C45H68O9).

DETAILED DESCRIPTION OF THE INVENTION

This invention provides a method of synthesising new active compounds for pharmaceutical uses. This invention provides an anti adhesion therapy which uses the compound as a mediator or inhibitor of adhesion proteins and angiopoietins. It inhibits excess adhesion and inhibits cell attachment. It modulates angiogenesis. The compounds also use as mediator of cell adhesion receptor.

This invention provides compounds or a composition comprising the compounds provided in the invention for treating cancers; for inhibiting cancer growth, for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular disease; inhibiting NF-Kappa B activation; for treating brain edema, severe acute respiratory syndrome, respiratory viral diseases, chronic venous insufficiency, hypertension, chronic venous disease, oedema, inflammation, hemonhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for AntiMS, antianeurysm, antiasthmatic, anti-oedematous, anti-inflammatory, antibradykinic, anticapillarihemorrhagic, anticephalagic, anticervicobrachialgic, antieclamptic, anti-edemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cancer cells, antiparasitic; increase the expression of the genes: ANGPT2, DDIT3, LIF and NFKB1Z, and manufacturing an adjuvant composition and venotonic treatment.

This invention provides compounds, compositions and methods for treating cancer diseases, inhibiting cancer invasion, for inhibiting cancer growth or for inhibiting cancer metastasis, wherein the compounds comprise the structures selected from the formulae of the present application, wherein the compounds can be synthesized or isolated, wherein the compounds comprise the triterpenes, pentacyclic triterpenes, saponins, and compounds selected from formulae in this application, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer; wherein the cells comprise breast cell, leukocytic cell, liver cell, ovarian cell, bladder cell, prostatic cell, skin cell, bone cell, brain cell, leukemia cell, lung cell, colon cell, CNS cell, melanoma cell, renal cell, cervical cell, esophageal cell, testicular cell, spleenic cell, kidney cell, lymphatic cell, pancreatic cell, stomach cell and thyroid cell.

This invention shows that the presence of Tigloyl, angeloyl, Acetyl, Crotonoyl, 3,3-Dimethylartyloyl, senecioyl, Cinnamoyl, Pentenoyl, Hexanoyl, benzoyl, Ethylbutyryl, dibenzoyl, alkanoyl, alkenoyl, benzoyl alkyl substituted alkanoyl, alkanoyl substituted phenyl, alkenoyl substituted phenyl, aryl, acyl, heterocylic, heteroraryl, sugar moiety, or sugar moiety substituted with diangeloyl groups, at a pentacyclic triterpene, triterpene, triterpeniod, triterpeniod saponin or compound selected from formulae of the present application, produces inhibition of cancer growth, cancer invasion, cells invasion, cancer cell invasion, cell adhesion, cell circulation or cell attachment.

This invention shows that the presence of Tigloyl, angeloyl, Acetyl, Crotonoyl, 3,3-Dimethylartyloyl, senecioyl, Cinnamoyl, Pentenoyl, Hexanoyl, benzoyl, Ethylbutyryl, dibenzoyl, alkanoyl, alkenoyl, benzoyl alkyl substituted alkanoyl, alkanoyl substituted phenyl, alkenoyl substituted phenyl, aryl, acyl, heterocylic, heteroraryl, sugar moiety, or sugar moiety substituted with diangeloyl groups, at carbon position 21, 22, 24 and/or 28 of a pentacyclic triterpene, triterpene, triterpeniod, triterpeniod saponin or compound selected from formulae of the present application, produces inhibition of cancer growth, cancer invasion, cells invasion or cancer cell invasion. In an embodiment, the presence of group(s) selected from Tigloyl, angeloyl, Acetyl, Crotonoyl, 3,3-Dimethylartyloyl, senecioyl, Cinnamoyl, Pentenoyl, Hexanoyl, benzoyl, Ethylbutyryl, dibenzoyl, alkanoyl, alkenoyl, benzoyl alkyl substituted alkanoyl, alkanoyl substituted phenyl, alkenoyl substituted phenyl, aryl, acyl, heterocylic, heteroraryl, and sugar moiety, at carbon position 3, 8, 15, 21, 22, 24 and/or 28 of a triterpene, triterpeniod, triterpeniod saponin or compound selected from formulae of the present application produces activities including inhibition of cancer growth, cancer invasion, cells invasion, cancer cell invasion, cell adhesion, cell attachment or cell circulating. In embodiment, the presence of group at carbon position 24, produces activities. In embodiment, the presence of group at carbon position 24 and 28 produces activities. In embodiment, the presence of group at carbon position 24 and 21 produces activities. In embodiment, the presence of group at carbon position 24, 28 and 21, produces activities. In embodiment, the presence of group at carbon position 24, 28 and 22 produces activities. In embodiment, the presence of group at carbon position 24, 28 and 3 produces activities. In embodiment, the presence of group at carbon position 24, and 3 produces activities. In embodiment, the presence of group at carbon position 28 and 3 produces activities. In embodiment, the presence of group at carbon position 3 produces activities. In embodiment, the presence of group at carbon position 21 and 22 produces activities. This invention shows a method of synthesizing active compound by attaching functional group to a core compound, wherein the functional group(s) is/are selected from tigloyl, angeloyl, acetyl, crotonoyl, 3,3-Dimethylartyloyl, senecioyl, cinnamoyl, pentenoyl, hexanoyl, benzoyl, ethylbutyryl, dibenzoyl, alkanoyl, alkenoyl, benzoyl alkyl substituted alkanoyl, alkanoyl substituted phenyl, alkenoyl substituted phenyl, aryl, acyl, heterocylic, and heteroraryl, wherein the core compound is a 5 ring triterpene. In embodiment, the core compound is a 4 ring terpene. In embodiment, the core compound is a 3 ring terpene. In embodiment, the core compound is a 2 ring terpene. In embodiment, the core compound is a 1 ring terpene. The compounds provided in the invention are for treating cancers, inhibition of cancer growth, cancer invasion, cells invasion, cancer cell invasion; cell adhesion, cell attachment, cell circulating; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-Kappa B activation; for treating brain edema, severe acute respiratory syndrome, respiratory viral diseases, chronic venous insufficiency, hypertension, chronic venous disease, oedema, inflammation, hemonhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for AntiMS, antianeurysm, antiasthmatic, anti-oedematous, anti-inflammatory, antibradykinic, anticapillarihemorrhagic, anticephalagic, anticervicobrachialgic, antieclamptic, antiedemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, antiparasitic; increase the expression of the genes: ANGPT2, DDIT3, LIF and NFKB1Z, and manufacturing an adjuvant composition and venotonic treatment.

Experiments presented in this invention showed that the compound AKOH has no effect in inhibiting cancer growth, cancer invasion, cells invasion or cancer cell invasion. AKOH was obtained by removing the angeloyl groups from carbon positions 21 and 22 of the active Xanifolia Y(Y3). This invention shows that the ability for inhibiting cancer invasion, cells invasion or cancer cell invasion of Xanifolia Y(Y3) are lost by removing angeloyl groups from carbon positions 21 and 22.

Experiments presented in this invention showed that the core compound including E4A, E5A, Xanifolia Y-core have no effect in inhibiting cancer growth, cancer invasion, cells invasion or cancer cell invasion. Xanifolia Y-core was obtained by removing the angeloyl groups from carbon positions 21 and 22, and the sugar moieties from carbon 3 of the active Xanifolia Y(Y3). E4A (E IV A) was obtained by removing the groups from carbon positions 3, 21 and 22 of the active Escin. E5A (E V A) was obtained by removing the groups from carbon positions 3, 21 and 22 of the active Escin.

This invention showed that the core compound including E4A, E5A, Xanifolia Y-core and AKOH have no hemolytic activity and anti cancer activity.

This invention showed that Tig-N, Tig-Q, Tig-R, Tig-T Tig-S and Tig-V do not have hemolytic activity up to 20 ug/ml. The original compound ES lyse 100% red blood cells (RBC) at 5 ug/ml. Compare to Y3, the ACH-Y3 is less potent in hemolytic activity. Tig-R has no hemolytic activity. This invention showed that Tig-N, Tig-Q, Tig-R, Tig-T Tig-S and Tig-V have anti cancer activities.

This invention shows that the ability for inhibiting cancer growth, cancer invasion, cells invasion or cancer cell invasion are maintained when the sugar moieties are removed from carbon position 3 of an active compound, triterpene, triterpeniod, or triterpeniod saponin. Experiments presented in this invention showed that the compound ACH-Y3 has the ability to inhibit cancer invasion, cells invasion or cancer cell invasion. The compound ACH-Y3 was obtained by removing the sugar moieties from carbon position 3 of a active Xanifolia Y(Y3). This invention shows that the ability for inhibiting cancer invasion, cells invasion or cancer cell invasion are maintained when the sugar moieties are removed from the carbon position 3 of active Xanifolia Y(Y3).

A compound which has bio-activities including inhibiting cancer growth, inhibiting cancer invasion, cells invasion or cancer cell invasion is called active compound.

This invention provides a use for compounds, compositions, and methods for manufacturing medicament for treating cancers, inhibition of cancer growth, cancer invasion, cells invasion, cancer cell invasion; cell adhesion, cell attachment, cell circulating, or for inhibiting cancer metastasis, wherein the compounds comprise the structures selected from the formulae of the present application, wherein the compounds can be synthesized or isolated, wherein the compounds comprise the pentacyclic triterpenes, wherein the cells comprise cancer cells, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer. The method of inhibiting cancer invasion, cells invasion or cancer cell invasion activities uses non-cytotoxic drug concentrations. The method of inhibiting metastasis uses non-cytotoxic drug concentrations. There is no noticeable change in cell morphology.

This invention provides methods for treating cancers, inhibition of cancer growth, cancer invasion, cells invasion, cancer cell invasion; cell adhesion, cell attachment, cell circulating, migration, metastasis or growth of cancers, wherein the methods comprise affecting gene expression, wherein the methods comprise stimulating gene expression, or wherein the methods comprise inhibiting the gene expression, or wherein the methods comprise administering to a subject an effective amount of compounds, compositions in this application. In an embodiment, the method comprises contacting said cell with a compound selected from A1-18, A20-32, B1-18, B20-32, C1-18, C20-32, D1-18, D20-32, D1-18, D20-32, D1-18, D20-32, D1-18, D20-32, D1-18, D20-32, E1-18, E20-32, G1-18, G20-32, H1-18, H20-32, I1-18, I20-32, J1-18, J20-32, K1-18, K20-32, Xanifolia Y0, Y1, Y2, Y(Y3), Y5, Y7, Y8, Y9, Y10, Xanifolia (x), M10, Escin (bES), Aescin, ACH-Y(Y3), ACH-Y10, ACH-Y2, ACH-Y8, ACH-Y7, ACH-Y0, ACH-X, ACH-Z4, ACH-Z1, ACH-Escin (bES), ACH-M10 and a salt, ester, metabolite thereof, and the compounds selected from formulae 2A, and K.

In vitro studies show that a compound selected from structure (2A) or (K) inhibits cell adhesion to culture flasks. The compound blocks the function of these adhesive molecules on cells. In an embodiment, the selected compound blocks the function of these adhesive molecules on cells. In an embodiment, the selected compound blocks the function of these adhesive molecules on carcinoma cells. In an embodiment, the selected compound blocks the function of these adhesive molecules on the mesothelial cells. This invention provides an anti adhesion therapy which uses the compound as amediator or inhibitor of adhesion proteins and angiopoietins. It inhibits excess adhesion and inhibits cell attachment. This invention provides compounds for use as a mediator for cell circulating, cell moving and inflammatory diseases. In an embodiment, the selected compound binds to the adhesive proteins (by masking) on the membrane and inhibits the interaction of adhesion proteins with their receptors. In an embodiment, the selected compound's action on the membrane affects adhesion proteins' function in the membrane. The lost of adhesion activity of cancer cells is result from direct or indirect action of the selected compound on membrane proteins.

(Our purification methods and biological assays include the MTT assay in International Application No. PCT/US05/31900, filed Sep. 7, 2005, U.S. Ser. No. 11/289,142, filed Nov. 28, 2005, and U.S. Ser. No. 11/131,551, filed May 17, 2005, and PCT/US2008/002086, 1188-ALA-PCT, filed Feb. 15, 2008, the cell invasion experiments methods in International Application PCT/US2010/0042240, filed Jul. 16, 2010, the contents of which are incorporated herein by reference)

This invention provides a use of compounds or methods for inhibiting cancer invasion, cell invasion, cancer cell invasion, migration, metastasis or growth of cancers, wherein this invention comprises a process and method for administration of the composition, wherein administration is by intravenous injection, intravenous drip, intraperitoneal injection or oral administration; wherein administration is by intravenous drip: 0.003-0.03 mg/kg body weight of compound dissolved in 250 ml of 10% glucose solution or in 250 ml of 0.9% NaCl solution, or by intravenous injection: 0.003-0.03 mg/kg body weight per day of compound dissolved in 10-20 ml of 10% glucose solution or of 0.9% NaCl solution, or 0.01-0.03 mg/kg body weight of compound dissolved in 250 ml of 10% glucose solution or in 250 ml of 0.9% NaCl solution, or by intravenous injection: 0.01-0.03 mg/kg body weight per day of compound dissolved in 10-20 ml of 10% glucose solution or of 0.9% NaCl solution, or 0.01-0.05 mg/kg body weight of compound dissolved in 250 ml of 10% glucose solution or in 250 ml of 0.9% NaCl solution, or by intravenous injection: 0.01-0.05 mg/kg body weight per day of compound dissolved in 10-20 ml of 10% glucose solution or of 0.9% NaCl solution, or 0.05-0.2 mg/kg body weight of compound dissolved in 250 ml of 10% glucose solution or in 250 ml of 0.9% NaCl solution, or by intravenous injection: 0.05-0.2 mg/kg body weight per day of compound dissolved in 10-20 ml of 10% glucose solution or of 0.9% NaCl solution, or by intravenous drip: 0.1-0.2 mg/kg body weight per day of compound dissolved in 250 ml of 10% glucose solution or in 250 ml of 0.9% NaCl solution, or by intravenous injection: 0.1-0.2 mg/kg body weight per day compound dissolved in 10-20 ml of 10% glucose solution or of 0.9% NaCl solution, or by intraperitoneal injection (I.P.): 2.5 mg/kg body weight per day compound dissolved in 10% glucose solution or of 0.9% NaCl solution, or by oral administration wherein the dosage of mammal is 1-10 mg/kg, 10-30 mg/kg, 30-60 mg/kg, or 60-90 mg/kg body weight of compound, or by intravenous injection or intravenous drip wherein the dosage of mammal is 0.01-0.1 mg/kg body weight, 0.1-0.2 mg/kg, 0.2-0.4 mg/kg body weight, or 0.4-0.6 mg/kg body weight of compound, or by intraperitoneal injection (I.P.) wherein the dosage of mammal is 1-3 mg/kg, 3-5 mg/kg, 4-6 mg/kg, or 6-10 mg/kg body weight of compound.

This invention provides a use of compounds or methods for treating cancers, inhibition of cancer growth, cancer invasion, cells invasion, cancer cell invasion; cell adhesion, cell attachment, cell circulating, migration, metastasis or growth of cancers, wherein the invention comprises a pharmaceutical composition comprising the compound of this invention or a pharmaceutically acceptable salt thereof, and a pharmaceutically acceptable carrier or diluent, wherein said compound is present in a concentration of 0.01 ug/ml to 65 ug/ml, or wherein said compound is present in a concentration of 0.01 ug/ml to 40 ug/ml, or wherein said compound is present in a concentration of 0.01 ug/ml to 30 ug/ml, or wherein said compound is present in a concentration of 0.01 ug/ml to 10 ug/ml, or wherein said compound is present in a concentration of 0.01 ug/ml to 5 ug/ml, or wherein said compound is present in a concentration of 5 ug/ml to 10 ug/ml, or wherein said compound is present in a concentration of 0.1 ug/ml to 5 ug/ml, or wherein said compound is present in a concentration of 0.1 ug/ml to 7.5 ug/ml, or wherein said compound is present in a concentration of 0.1 ug/ml to 10 ug/ml, or wherein said compound is present in a concentration of 0.1 ug/ml to 15 ug/ml, or wherein said compound is present in a concentration of 0.1 ug/ml to 20 ug/ml, or wherein said compound is present in a concentration of 0.1 ug/ml to 30 ug/ml, or wherein said compound is present in a concentration of 1 ug/ml to 5 ug/ml, or wherein said compound is present in a concentration of 1 ug/ml to 7.5 ug/ml, or wherein said compound is present in a concentration of 1 ug/ml to 10 ug/ml, or wherein said compound is present in a concentration of 1 ug/ml to 15 ug/ml, or wherein said compound is present in a concentration of 1 ug/ml to 20 ug/ml, or wherein said compound is present in a concentration of 1 ug/ml to 30 ug/ml, or wherein said compound is present in a concentration of 3 ug/ml to 5 ug/ml, or wherein said compound is present in a concentration of 3 ug/ml to 7.5 ug/ml, or wherein said compound is present in a concentration of 3 ug/ml to 10 ug/ml, or wherein said compound is present in a concentration of 3 ug/ml to 15 ug/ml, or wherein said compound is present in a concentration of 3 ug/ml to 20 ug/ml, or wherein said compound is present in a concentration of 3 ug/ml to 30 ug/ml, or wherein said compound is present in a concentration of 4 ug/ml to 5 ug/ml, or wherein said compound is present in a concentration of 4 ug/ml to 7.5 ug/ml, or wherein said compound is present in a concentration of 4 ug/ml to 10 ug/ml, or wherein said compound is present in a concentration of 4 ug/ml to 15 ug/ml, or wherein said compound is present in a concentration of 4 ug/ml to 20 ug/ml, or wherein said compound is present in a concentration of 4 ug/ml to 30 ug/ml, or wherein said compound is present in a concentration of 5 ug/ml to 8 ug/ml, or wherein said compound is present in a concentration of 5 ug/ml to 9 ug/ml, or wherein said compound is present in a concentration of 5 ug/ml to 10 ug/ml, or wherein said compound is present in a concentration of 5 ug/ml to 15 ug/ml, or wherein said compound is present in a concentration of 5 ug/ml to 20 ug/ml, or wherein said compound is present in a concentration of 5 ug/ml to 30 ug/ml, or wherein said compound is present in a concentration of 7 ug/ml to 8 ug/ml, or wherein said compound is present in a concentration of 7 ug/ml to 9 ug/ml, or wherein said compound is present in a concentration of 7 ug/ml to 10 ug/ml, or wherein said compound is present in a concentration of 7 ug/ml to 15 ug/ml, or wherein said compound is present in a concentration of 7 ug/ml to 20 ug/ml, or wherein said compound is present in a concentration of 7 ug/ml to 30 ug/ml.

This invention provides a use of compounds or methods for treating cancers, inhibition of cancer growth, cancer invasion, cells invasion, cancer cell invasion; cell adhesion, cell attachment, cell circulating, migration, metastasis or growth of cancers, wherein the invention comprises a pharmaceutical composition comprising the compound of this invention or a pharmaceutically acceptable salt thereof, and a pharmaceutically acceptable carrier or diluent, wherein said compound is present in a concentration of 0.008 uM to 80 uM, or wherein said compound is present in a concentration of 0.01 uM to 60 uM, or wherein said compound is present in a concentration of 0.01 uM to 50 uM, or wherein said compound is present in a concentration of 0.01 uM to 40 uM, or wherein said compound is present in a concentration of 0.01 uM to 30 uM, or wherein said compound is present in a concentration of 0.01 uM to 20 uM, or wherein said compound is present in a concentration of 0.01 uM to 10 uM, or wherein said compound is present in a concentration of 5 uM to 10 uM, or wherein said compound is present in a concentration of 0.1 uM to 5 uM, or wherein said compound is present in a concentration of 0.1 uM to 7.5 uM, or wherein said compound is present in a concentration of 0.1 uM to 10 uM, or wherein said compound is present in a concentration of 0.1 uM to 15 uM, or wherein said compound is present in a concentration of 0.1 uM to 20 uM, or wherein said compound is present in a concentration of 0.1 uM to 30 uM or wherein said compound is present in a concentration of 0.1 uM to 40 uM, or wherein said compound is present in a concentration of 0.1 uM to 50 uM or wherein said compound is present in a concentration of 0.1 uM to 60 uM, or wherein said compound is present in a concentration of 0.1 uM to 80 uM, or wherein said compound is present in a concentration of 1 uM to 5 uM, or wherein said compound is present in a concentration of 1 uM to 7.5 uM, or wherein said compound is present in a concentration of 1 uM to 10 uM, or wherein said compound is present in a concentration of 1 uM to 15 uM, or wherein said compound is present in a concentration of 1 uM to 20 uM, or wherein said compound is present in a concentration of 1 uM to 30 uM or wherein said compound is present in a concentration of 1 uM to 40 uM, or wherein said compound is present in a concentration of 1 uM to 50 uM or wherein said compound is present in a concentration of 1 uM to 60 uM, or wherein said compound is present in a concentration of 1 uM to 80 uM, or wherein said compound is present in a concentration of 3 uM to 5 uM, or wherein said compound is present in a concentration of 3 uM to 7.5 uM, or wherein said compound is present in a concentration of 3 uM to 10 uM, or wherein said compound is present in a concentration of 3 uM to 15 uM, or wherein said compound is present in a concentration of 3 uM to 20 uM, or wherein said compound is present in a concentration of 3 uM to 30 uM or wherein said compound is present in a concentration of 3 uM to 40 uM, or wherein said compound is present in a concentration of 3 uM to 50 uM or wherein said compound is present in a concentration of 3 uM to 60 uM, or wherein said compound is present in a concentration of 3 uM to 80 uM, or wherein said compound is present in a concentration of 5 uM to 8 uM, or wherein said compound is present in a concentration of 5 uM to 10 uM, or wherein said compound is present in a concentration of 5 uM to 15 uM, or wherein said compound is present in a concentration of 5 uM to 20 uM, or wherein said compound is present in a concentration of 5 uM to 30 uM or wherein said compound is present in a concentration of 5 uM to 40 uM, or wherein said compound is present in a concentration of 5 uM to 50 uM or wherein said compound is present in a concentration of 5 uM to 60 uM, or wherein said compound is present in a concentration of 5 uM to 80 uM. or wherein said compound is present in a concentration of 7 uM to 8 uM, or wherein said compound is present in a concentration of 7 uM to 10 uM, or wherein said compound is present in a concentration of 7 uM to 15 uM, or wherein said compound is present in a concentration of 7 uM to 20 uM, or wherein said compound is present in a concentration of 7 uM to 30 uM or wherein said compound is present in a concentration of 7 uM to 40 uM, or wherein said compound is present in a concentration of 7 uM to 50 uM or wherein said compound is present in a concentration of 7 uM to 60 uM, or wherein said compound is present in a concentration of 7 uM to 80 uM.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains.

It is to be noted that the transitional term "comprising", which is synonymous with "including", "containing" or "characterized by", is inclusive or open-ended and does not exclude additional, un-recited elements or method steps.

Example 1

Tablet for Dose Containing 10 mg, 20 mg 30 mg of Active Compound

Citric acid 1-15 mg
Sodium chloride 1-8 mg
Water for injection (USP) q.s. to 1 mL Utilizing the above quantities, the active compound is dissolved at room temperature in a prepared solution of sodium chloride, citric acid, and sodium citrate in water for injection.

Example 3

Intravenous Drip Preparation 0.25-2.5 mg compound dissolved in 250 ml of 10% glucose solution or in 250 ml of 0.9% NaCl solution.

Intravenous drip preparation: 1-2.mg compound dissolved in 250 ml of 10% glucose solution or in 250 ml of 0.9% NaCl solution Treatment of angelic acid with one of the many standard chlorinating reagents including phosphorus ocychloride, phosphorus trichloride and thionyl chloride produces tigloyl chloride. Oxalyl chloride produces a 2:1 ratio of angeloyl chloride to tigloyl chloride. Treatment of potassium salt in diethyl ether with oxalyl chloride and catalytic DMF for 2 hr at 0 C produces pure angeloyl chloride.

| Active compound | 1 mg | 5 mg | 10 mg | 20 mg | 30 mg |
|---|---|---|---|---|---|
| Microcrystalline cellulose | 20 mg | 20 mg | 19.75 mg | 60 mg | 100 mg |
| Corn starch | 29 mg | 24.5 mg | 19.75 mg | 19.25 mg | 18.5 mg |
| Magnesium stearate | 0 mg | 0.5 mg | 0.5 mg | 0.75 mg | 1.5 mg |

The active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1, 5, 10, 20, 30 mg, respectively of active ingredient per tablet.

Example 2

Intravenous Solution Preparation

An intravenous dosage form of the active compound is prepared as follows:
Active compound 1-10 ug
Sodium citrate 5-50 mg

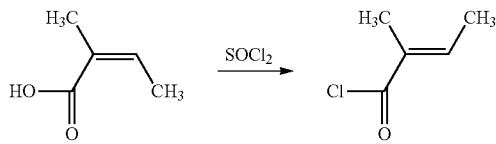

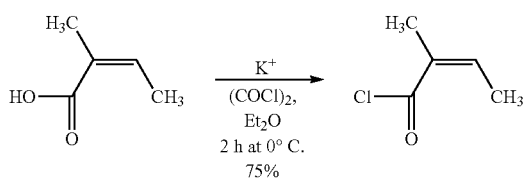

Acid Hydrolysis of the Following Compounds:
a) Xanifolia (Y),
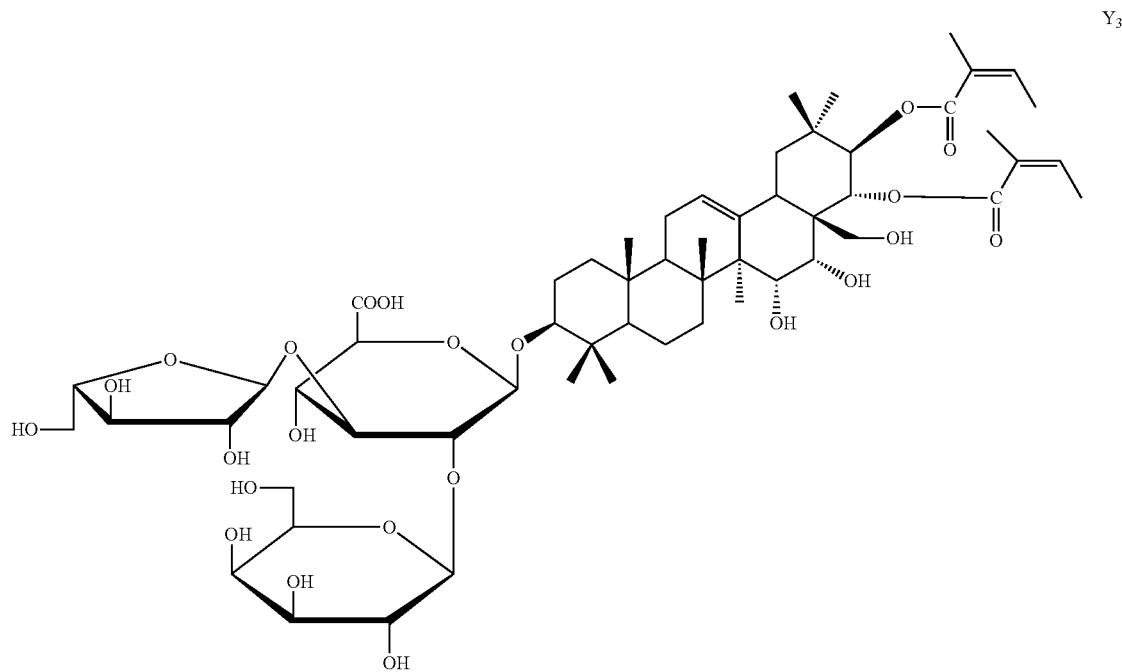
or chemical name: 3-O-[β-D-galactopyranosyl(1→2)]-α-L-arabinofuranosy(1→3)-β-D-glucuronopyranosyl-21,22-O-diangeloyl-3β,15α,16α,21β,22α,28-hexahydroxyolean-12-ene;
c) Xanifolia (Y2),
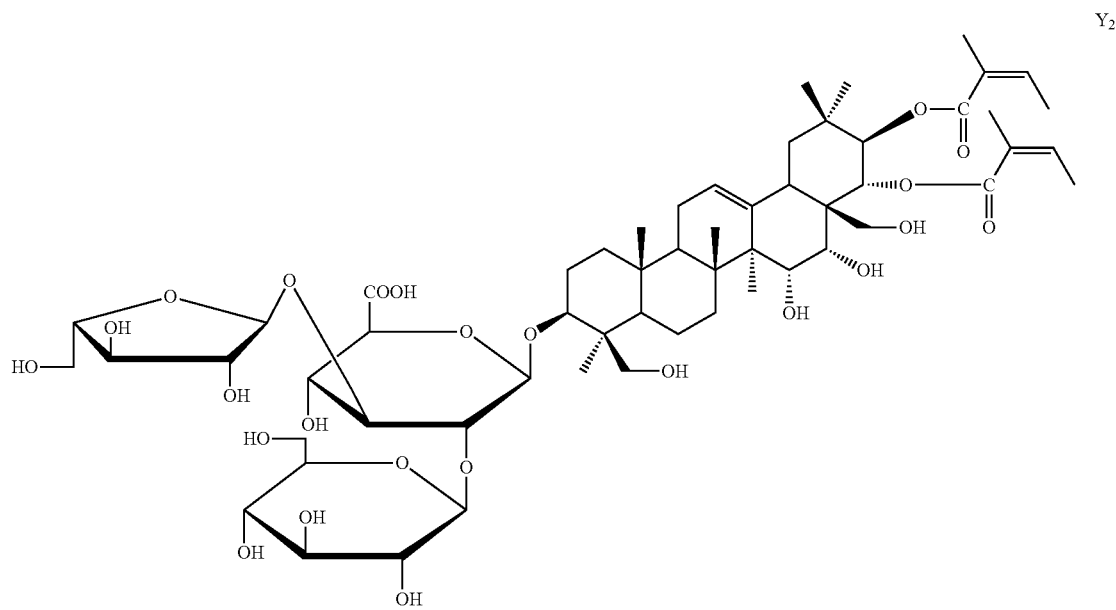

or chemical name: 3-O-[β-D-glucopyranosyl-(1→2)]α-L-arabinofuranosy(1→3)-β-D-glucuronopyranosyl-21,22-O-diangeloyl-3β,15α,16α,21β,22α,24β,28-heptahydroxy-olean-12-ene;
d) Xanifolia (Y8),
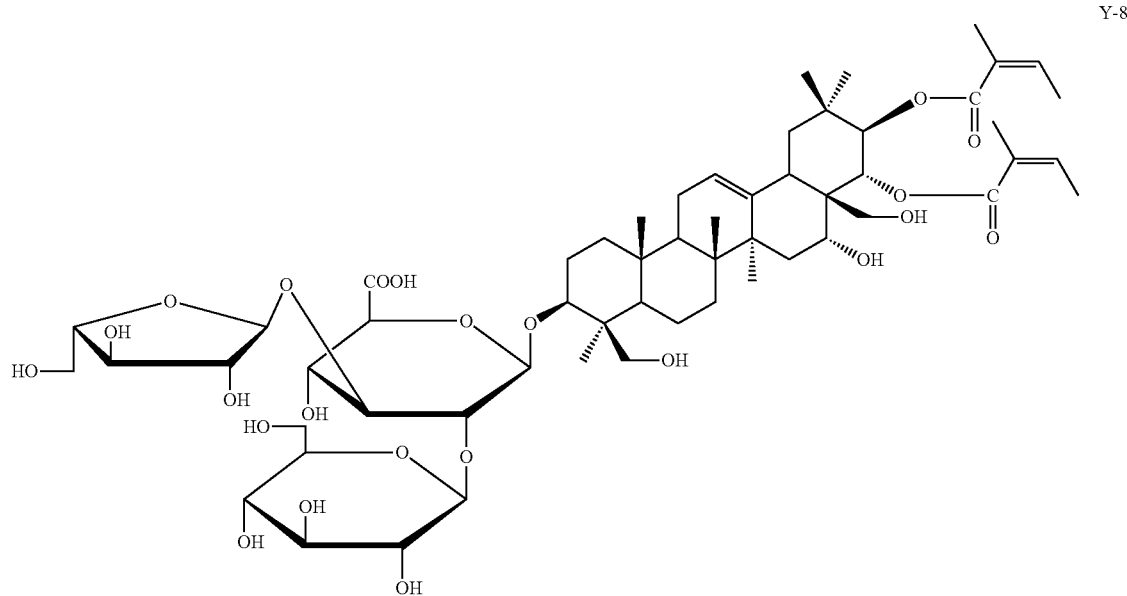
or chemical name: 3-O-[β-glucopyranosyl(1→2)]-α-arabinofuranosyl(1→3)-β-glucuronopyranosyl-21,22-O-diangeloyl-3β,16α,21β,22α,24β,28-hexahydroxyolean-12-ene;
f) Xanifolia (Y10),
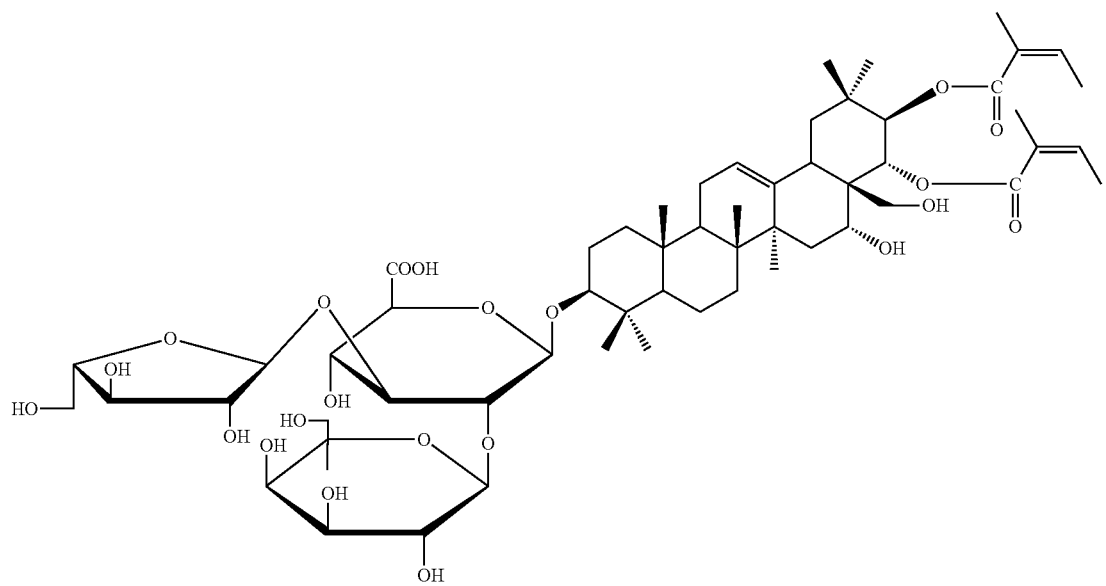

or chemical name: 3-O-[β-galactopyranosyl(1→2)]-α-arabinofuranosyl(1→3)-β-glucuronopyranosyl-21,22-O-diangeloyl-3β,16α,21β,22α,28-pentahydroxyolean-12-ene.
j) Structure (M10)
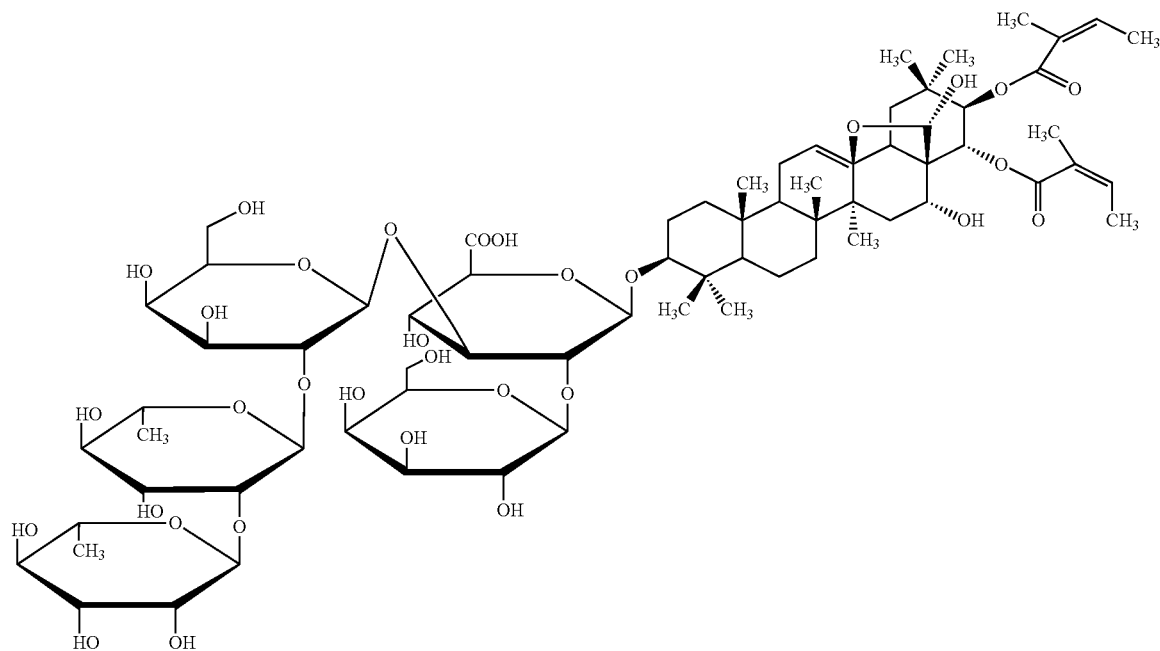
m) Structure (bES):
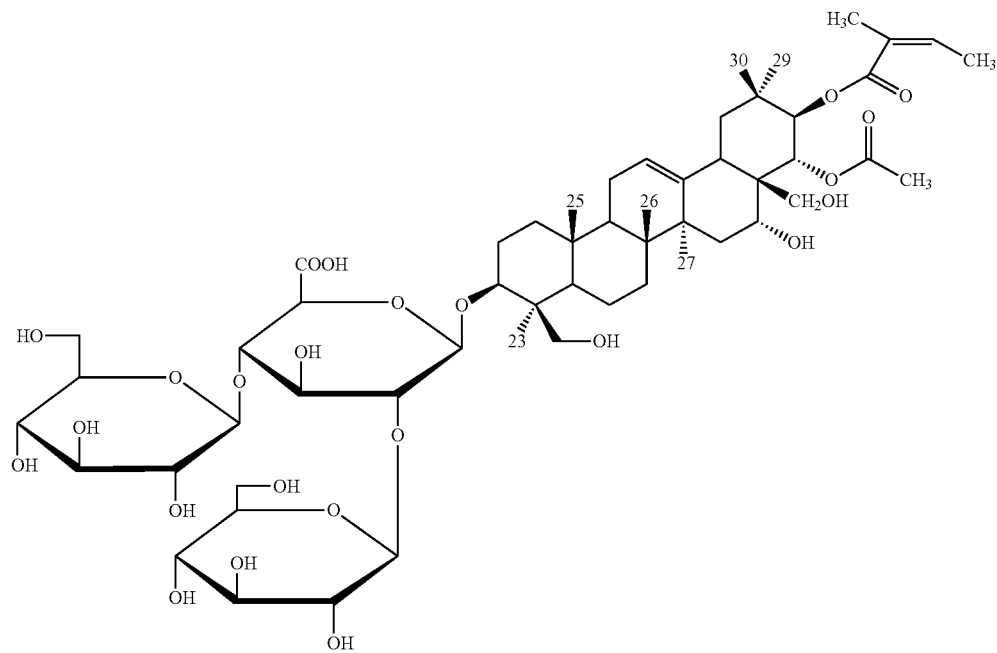

After acid hydrolysis of the above, an isolated, purified or synthesized compound is produced having a structure (ACH) selected from following:

ACH-Y

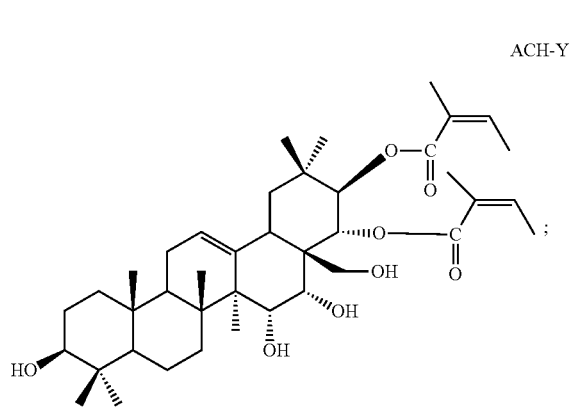

ACH-Y10

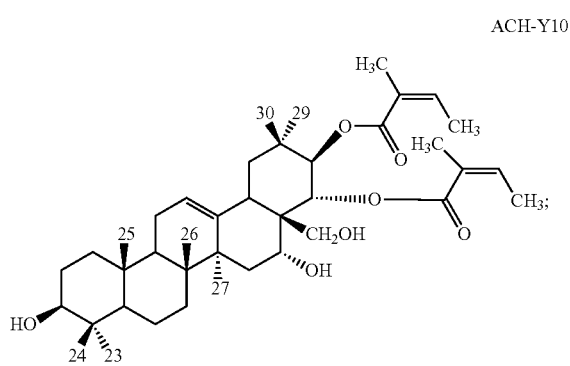

ACH-Y2

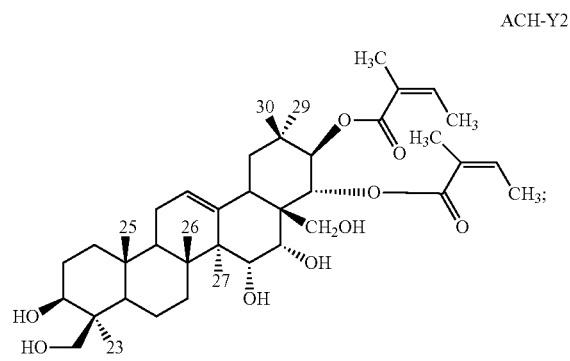

ACH-bES

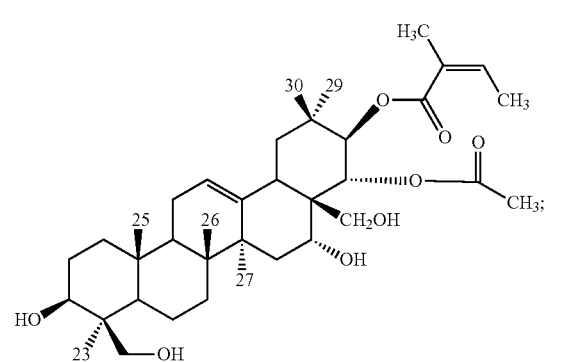

ACH-M10

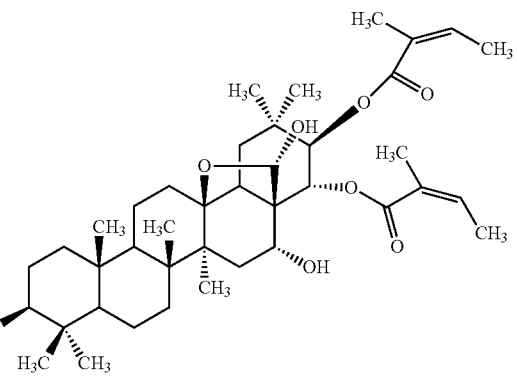

The composition comprises bioactive compounds from natural plants or synthesis. The program is based on our purification methods and biological assays including the MTT assay. See International Application No. PCT/US05/31900, filed Sep. 7, 2005, U.S. Ser. No. 11/289,142, filed Nov. 28, 2005, and U.S. Ser. No. 11/131,551, filed May 17, 2005, and PCT/US2008/002086, 1188-ALA-PCT, filed Feb. 15, 2008, Ser. No. 12/344,682, 1020-B1-US, filed Dec. 29, 2008, the contents of which are incorporated herein by reference. The details of Analysis of gene expression of ES2 cells after Y-treatment by Microarray, Data Analysis Methods and Western blot in PCT/US2008/002086, 1188-ALA-PCT, filed Feb. 15, 2008, and the cell invasion experiments methods in International Application PCT/US2010/0042240, filed Jul. 16, 2010, the contents of which are incorporated herein by reference.

The Haemolytic Assay

Erythrocytes (RBC) were isolated from human blood (EDTA whole blood, collected randomly). 50 ul of the 10% RBC suspension (in PBS) was added to 2 ml of sample solutions (concentration range from 0.1 ug/ml to 400 ug/ml) in PBS. The mixture was vortexed briefly and sat for 60 min at room temperature. The mixture was spun at 3K for 10 min and the relative amounts of lysed hemoglobin in the supernatant were measured at 540 nm. The synthetic compounds of present application were tested with this method.

Acid Hydrolysis of Saponin 15 mg Xanifolia-Y was dissolved in 1 ml of methanol. 1 ml of 2N HCl was then added. The mixture was refluxed in 80 C water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (ACH-Y) was achieved by HPLC with isocratic elution of 80-100% acetonitrile. Repeating the experiment with compounds Z4, Y10, Y2, Y8, Y7, Y0, X, M10 and ESCIN (bES) gives the following compounds respectively: ACH-Z4, ACH-Y10, ACH-Y2, ACH-Y8, ACH-Y7, ACH-Y0, ACH-X, ACH-E, ACH-Z5, ACH-M10 and ACH-bES. Experiments methods in International Application PCT/US2010/0042240, filed Jul. 16, 2010, the contents of which are incorporated herein by reference.

Removal of the Acyl Group by Alkaline Hydrolysis 20 mg of Xanifolia-Y was dissolved in 0.5 ml of 1N NaOH. The solution was incubated in 80 C water bath for 4 hours. It was cooled to room temperature before being neutralized with 0.5 ml 1N HCl (adjust pH to about 3). The mixture was extracted with 2 ml 1-butanol 3 times. The butanol fractions were collected and lyophilized. The hydrolyzed saponin was further purified with HPLC in a C-18 column eluted with 25% acetonitrile.

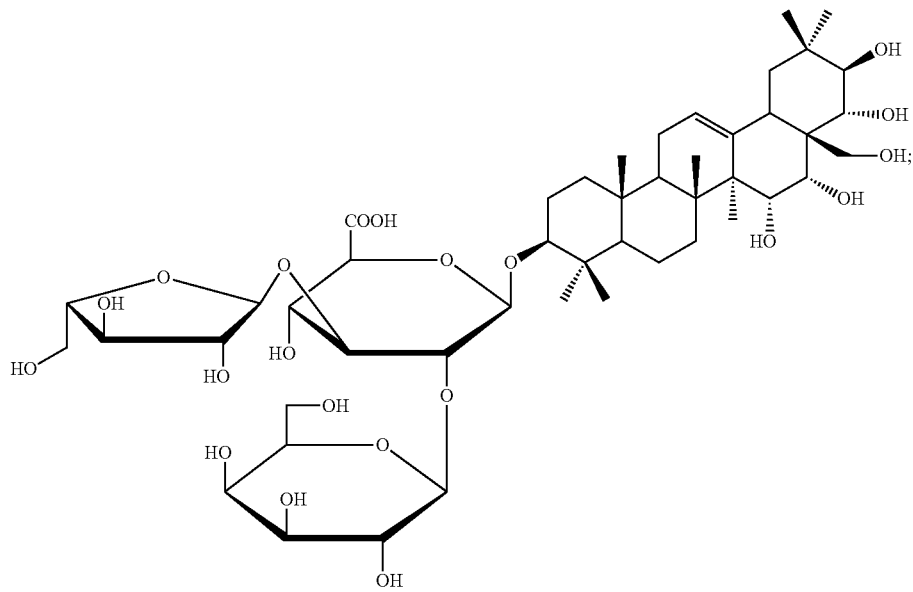
AKOH-Y
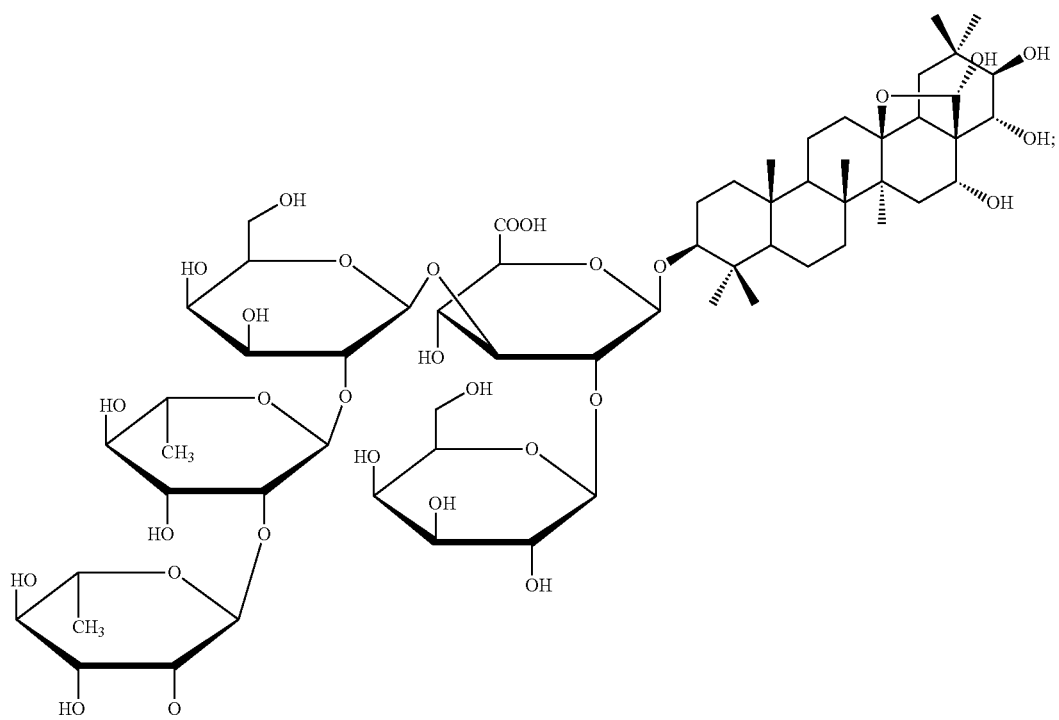
AKOH-M10

Compounds AKOH-Y and AKOH-M10 do not show the ability to inhibit cancer growth, cancer invasion, cells invasion or cancer cell invasion.

Core Compound

A core compound or pentacyclic triterpenes, hydroxylated triterpenes is obtained by acid and alkaline hydroysis of saponin from natural sources. A pentacyclic triterpene can also be obtained by synthetic methods. A method for synthesizing the core compound is as follows:

Beta-Escin, compound Y, Y10, Y2, Y8, Y7, Y0, X, or M10 dissolved in 1M NaOH (20 mg/ml) was incubated at 70 C for 5 hours. The hydrolyzed solution was neutralized with HCl and the water was evaporated by lyophilization. The product was dissolved in 50% methanol and 1N HCl. The mixture was incubated at 70 C for 5 hours. The solution was neutralized with NaOH. The hydrolyzed product was extracted with ethylacetate, which was subsequently removed by evaporation. Further purification of the hydrolyzed product of core compounds including (E4A) were archived with FPLC chromatography in a C18 column equilibrated with 70% acetonitrile/TFA at the flow rate of 1 ml/min. The core compounds are obtained.

The core compounds do not show the ability to inhibit cancer growth, cancer invasion, or cell adhesion.

The Structures of Core Compounds:

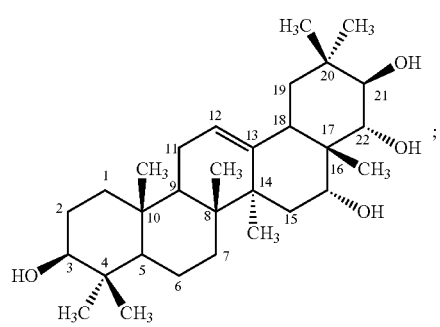

(A)

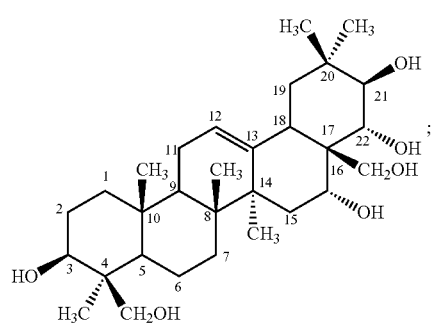

(B)

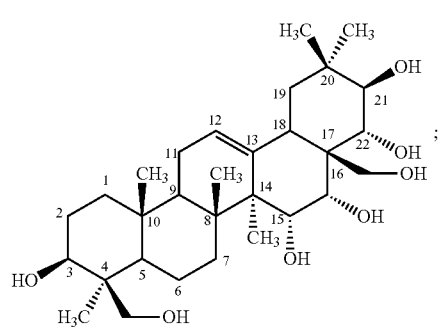

(C)

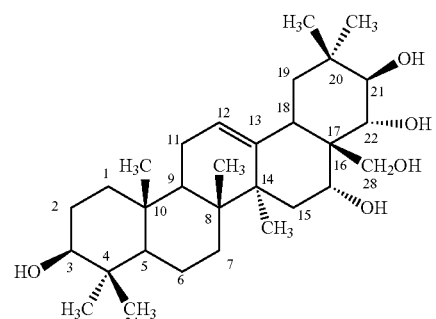

(D)

(E)

also named as bES-core, E IV A, ES4A, E4A or (E);

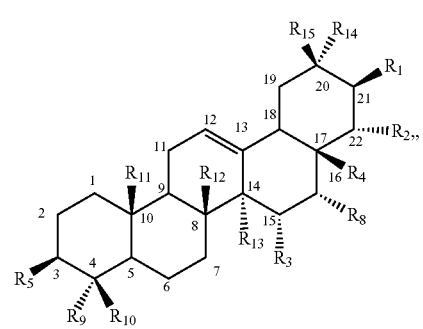

also named as ES V, E5A or (F)

(G)

wherein R1, R2, R5, R8 represent OH; R3 represents OH, H or absent; R4, R10 represent CH3 or CH2OH; R9, R11, R12, R13, R14, R15 represent CH3;

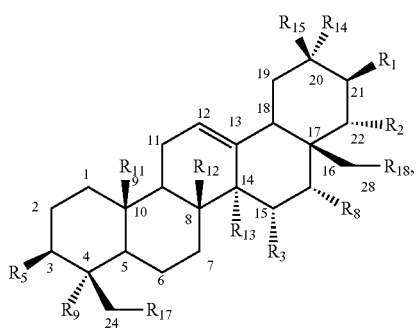

(H)

wherein R1, R2, R5, R8, R17, R18 represent OH; R3 represents OH, H or absent; R9, R11, R12, R13, R14, R15 represent CH3.

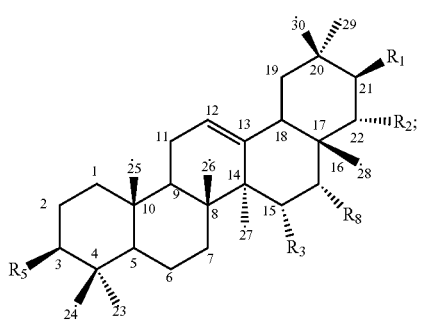

(J)

A typical numbering 1 to 30 of carbon positions of a pentacyclic triterpene.

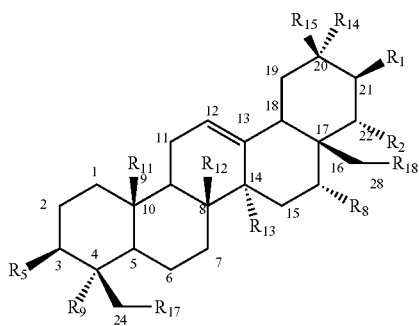

wherein R1, R2, R5, R8, R17, R18 represent OH; R9, R11, R12, R13, R14, R15 represent CH3, also named E4A or (E).

This invention provides a method of synthesizing new active compounds. A method of attaching functional groups to the core compounds [including but not limited to (A), (B), (C), (D), (E), (F), (G), (H)] involves esterification of core compounds with acyl chloride including but not limited to Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride or Ethylbutyryl chloride for 5 sec, 1 min, 2 min, 5 min, 10 min, 30 min, 1 hr, 2 hr, 18 hr, 2 days or 3 days at 0 C, 25 C or 75 C temperature. At the end of reaction, 5 ml of 2N HCl or 1M NaHCO3 is added to the reaction mixture. The solution is then extracted 3 times with 10 ml of ethyl acetate which is then evaporated under vacuum and at 45 C and lyophilization. The reaction product is dissolved in 80% acetonitrile-0.005% Trifluoroacetic acid. The active esterification products are purified with HPLC. MTT activity was performed to test the activity of acyl chloride, solution after the reaction, individual fractions, and individual compounds. The core compounds are synthetic, semi synthetic or from natural source. The core compounds are including terpene, isoprene, triterpenes, and hydroxylated triterpenes.

MTT activity of acylation of core compounds in different reaction time period of (ASAP)5 sec, 1 min, 2 min, 5 min, 10 min, 30 min, 1 hr, 2 hr, 18 hr, 2 days or 3 days at 0 C, 25 C or 75 C temperature were studied. HPLC profiles of esterification products of core compound E4A with acyl chloride including tigloyl chloride, angeloyl chloride, acetyl chloride, crotonoyl chloride, 3,3-Dimethylartyloyl chloride, senecioyl chloride, cinnamoyl chloride, pentenoyl chloride, hexanoyl chloride, benzoyl chloride or ethylbutyryl chloride show that the compounds vary in composition when the time or temperature of the reaction is changed. See FIGS. 1-21

The peaks, fractions and compounds are selected according to the activities of times studies and the changes of peaks. Selecting the HPLC fractions for isolation is according to the cytotoxic activity of the reaction product obtained at a specific time. The compounds having strong to weak activities are selected and isolated. The anti cancer activities are the MU studies of bone (U2OS), lung (H460), bladder (HTB-9), ovary (ES2), colon (HCT116), pancreas (Capan), ovary (OVCAR3), prostate (DU145), skin (SK-MeI-5), mouth (KB), kidney (A498), breast (MCF-7), liver (HepG2), brain (T98G), leukemia (K562), cervix (HeLa).

Esterification of core compound E4A with Tigloyl chloride and isolation of the compounds with HPLC give the following compounds:

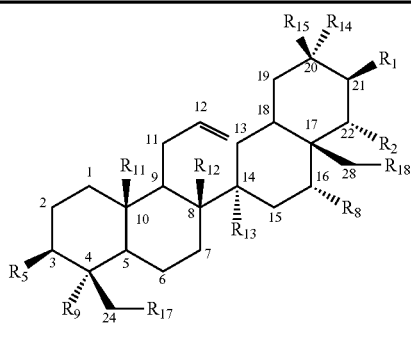

| | R1 | R2 | R5 | R8 | R17 | R18 | Cytotoxicity activity |
|---|---|---|---|---|---|---|---|
| E4A | OH | OH | OH | OH | OH | OH | none |
| A1 | OH | OH | OH | OH | O-Tig | OH | moderate |
| A2 | OH | OH | OH | OH | OH | O-Tig | moderate |
| A3 | OH | OH | OH | OH | O-Tig | O-Tig | strong |
| A4 | O-Tig | OH | OH | OH | O-Tig | O-Tig | moderate |
| A5 | OH | O-Tig | OH | OH | O-Tig | O-Tig | moderate |
| A6 | OH | OH | O-Tig | OH | O-Tig | O-Tig | moderate |
| A7 | OH | OH | OH | O-Tig | O-Tig | O-Tig | moderate |
| A8 | O-Tig | O-Tig | OH | OH | O-Tig | O-Tig | weak |
| A9 | OH | O-Tig | O-Tig | OH | O-Tig | O-Tig | weak |
| A10 | OH | OH | O-Tig | O-Tig | O-Tig | O-Tig | weak |
| A11 | O-Tig | OH | O-Tig | OH | O-Tig | O-Tig | weak |
| A12 | OH | O-Tig | OH | O-Tig | O-Tig | O-Tig | weak |
| A13 | O-Tig | OH | OH | O-Tig | O-Tig | O-Tig | weak |
| A14 | OH | O-Tig | O-Tig | OH | O-Tig | O-Tig | weak |
| A15 | O-Tig | O-Tig | O-Tig | OH | O-Tig | O-Tig | weak |
| A16 | O-Tig | O-Tig | OH | O-Tig | O-Tig | O-Tig | weak |

| | R1 | R2 | R5 | R8 | R17 | R18 | Cytotoxicity activity |
|---|---|---|---|---|---|---|---|
| A17 | O-Tig | OH | O-Tig | O-Tig | O-Tig | O-Tig | weak |
| A18 | OH | O-Tig | O-Tig | O-Tig | O-Tig | O-Tig | weak |
| A19 | O-Tig | O-Tig | O-Tig | O-Tig | O-Tig | O-Tig | none |
| A20 | O-Tig | O-Tig | OH | OH | OH | O-Tig | moderate |
| A21 | O-Tig | O-Tig | OH | OH | O-Tig | OH | moderate |
| A22 | O-Tig | O-Tig | OH | O-Tig | OH | OH | moderate |
| A23 | O-Tig | O-Tig | O-Tig | OH | OH | OH | moderate |
| A24 | O-Tig | O-Tig | OH | OH | OH | OH | moderate |
| A25 | O-Tig | OH | OH | OH | OH | O-Tig | moderate |
| A26 | OH | O-Tig | OH | OH | OH | O-Tig | moderate |
| A27 | OH | OH | O-Tig | OH | OH | O-Tig | moderate |
| A28 | OH | OH | OH | O-Tig | OH | O-Tig | moderate |
| A29 | O-Tig | OH | OH | OH | O-Tig | OH | moderate |
| A30 | OH | O-Tig | OH | OH | O-Tig | OH | moderate |
| A31 | OH | OH | O-Tig | OH | O-Tig | OH | moderate |
| A32 | OH | OH | OH | O-Tig | O-Tig | OH | moderate |

Esterification of core compound E4A with Angeloyl chloride and isolation of the compounds with HPLC give the following compounds:

| | R1 | R2 | R5 | R8 | R17 | R18 | Cytotoxicity activity |
|---|---|---|---|---|---|---|---|
| E4A | OH | OH | OH | OH | OH | OH | none |
| G1 | OH | OH | OH | OH | O-Ang | OH | moderate |
| G2 | OH | OH | OH | OH | OH | O-Ang | moderate |
| G3 | OH | OH | OH | OH | O-Ang | O-Ang | strong |
| G4 | O-Ang | OH | OH | OH | O-Ang | O-Ang | moderate |
| G5 | OH | O-Ang | OH | OH | O-Ang | O-Ang | moderate |
| G6 | OH | OH | O-Ang | OH | O-Ang | O-Ang | moderate |
| G7 | OH | OH | OH | O-Ang | O-Ang | O-Ang | moderate |
| G8 | O-Ang | O-Ang | OH | OH | O-Ang | O-Ang | weak |
| G9 | OH | O-Ang | O-Ang | OH | O-Ang | O-Ang | weak |
| G10 | OH | OH | O-Ang | O-Ang | O-Ang | O-Ang | weak |
| G11 | O-Ang | OH | O-Ang | OH | O-Ang | O-Ang | weak |
| G12 | OH | O-Ang | OH | O-Ang | O-Ang | O-Ang | weak |
| G13 | O-Ang | OH | OH | O-Ang | O-Ang | O-Ang | weak |
| G14 | OH | O-Ang | O-Ang | OH | O-Ang | O-Ang | weak |
| G15 | O-Ang | O-Ang | O-Ang | OH | O-Ang | O-Ang | weak |
| G16 | O-Ang | O-Ang | OH | O-Ang | O-Ang | O-Ang | weak |
| G17 | O-Ang | OH | O-Ang | O-Ang | O-Ang | O-Ang | weak |
| G18 | OH | O-Ang | O-Ang | O-Ang | O-Ang | O-Ang | weak |
| G19 | O-Ang | O-Ang | O-Ang | O-Ang | O-Ang | O-Ang | none |
| G20 | O-Ang | O-Ang | OH | OH | OH | O-Ang | moderate |
| G21 | O-Ang | O-Ang | OH | OH | O-Ang | OH | moderate |
| G22 | O-Ang | O-Ang | OH | O-Ang | OH | OH | moderate |
| G23 | O-Ang | O-Ang | O-Ang | OH | OH | OH | moderate |
| G24 | O-Ang | O-Ang | OH | OH | OH | OH | moderate |
| G25 | O-Ang | OH | OH | OH | OH | O-Ang | moderate |
| G26 | OH | O-Ang | OH | OH | OH | O-Ang | moderate |
| G27 | OH | OH | O-Ang | OH | OH | O-Ang | moderate |
| G28 | OH | OH | OH | O-Ang | OH | O-Ang | moderate |
| G29 | O-Ang | OH | OH | OH | O-Ang | OH | moderate |
| G30 | OH | O-Ang | OH | OH | O-Ang | OH | moderate |
| G31 | OH | OH | O-Ang | OH | O-Ang | OH | moderate |
| G32 | OH | OH | OH | O-Ang | O-Ang | OH | moderate |

Esterification of core compound E4A with (3,3-Dimethylartyloyl chloride) senecioyl chloride and isolation of the compounds with HPLC give the following compounds:

Sen=senecioyl

| | R1 | R2 | R5 | R8 | R17 | R18 | Cytotoxicity activity |
|---|---|---|---|---|---|---|---|
| E4A | OH | OH | OH | OH | OH | OH | none |
| B1 | OH | OH | OH | OH | O-Sen | OH | moderate |
| B2 | OH | OH | OH | OH | OH | O-Sen | moderate |
| B3 | OH | OH | OH | OH | O-Sen | O-Sen | strong |
| B4 | O-Sen | OH | OH | OH | O-Sen | O-Sen | moderate |
| B5 | OH | O-Sen | OH | OH | O-Sen | O-Sen | moderate |
| B6 | OH | OH | O-Sen | OH | O-Sen | O-Sen | moderate |
| B7 | OH | OH | OH | O-Sen | O-Sen | O-Sen | moderate |
| B8 | O-Sen | O-Sen | OH | OH | O-Sen | O-Sen | weak |
| B9 | OH | O-Sen | O-Sen | OH | O-Sen | O-Sen | weak |
| B10 | OH | OH | O-Sen | O-Sen | O-Sen | O-Sen | weak |
| B11 | O-Sen | OH | O-Sen | OH | O-Sen | O-Sen | weak |
| B12 | OH | O-Sen | OH | O-Sen | O-Sen | O-Sen | weak |
| B13 | O-Sen | OH | OH | O-Sen | O-Sen | O-Sen | weak |
| B14 | OH | O-Sen | O-Sen | OH | O-Sen | O-Sen | weak |
| B15 | O-Sen | O-Sen | O-Sen | OH | O-Sen | O-Sen | weak |
| B16 | O-Sen | O-Sen | OH | O-Sen | O-Sen | O-Sen | weak |
| B17 | O-Sen | OH | O-Sen | O-Sen | O-Sen | O-Sen | weak |
| B18 | OH | O-Sen | O-Sen | O-Sen | O-Sen | O-Sen | weak |
| B19 | O-Sen | O-Sen | O-Sen | O-Sen | O-Sen | O-Sen | none |
| B20 | O-Sen | O-Sen | OH | OH | OH | O-Sen | moderate |
| B21 | O-Sen | O-Sen | OH | OH | O-Sen | OH | moderate |
| B22 | O-Sen | O-Sen | OH | O-Sen | OH | OH | moderate |
| B23 | O-Sen | O-Sen | OH | OH | OH | OH | moderate |
| B24 | O-Sen | O-Sen | OH | OH | OH | OH | moderate |
| B25 | O-Sen | OH | OH | OH | OH | O-Sen | moderate |
| B26 | OH | O-Sen | OH | OH | OH | O-Sen | moderate |
| B27 | OH | OH | O-Sen | OH | OH | O-Sen | moderate |

|     | R1   | R2   | R5    | R8    | R17   | R18   | Cytotoxicity activity |
|-----|------|------|-------|-------|-------|-------|-----------|
| B28 | OH   | OH   | OH    | O-Sen | OH    | O-Sen | moderate  |
| B29 | O-Sen| OH   | OH    | OH    | O-Sen | OH    | moderate  |
| B30 | OH   | O-Sen| OH    | OH    | O-Sen | OH    | moderate  |
| B31 | OH   | OH   | O-Sen | OH    | O-Sen | OH    | moderate  |
| B32 | OH   | OH   | OH    | O-Sen | O-Sen | OH    | moderate  |

Esterification of core compound E4A with 4-Pentenoyl chloride and isolation of the compounds with HPLC give the following compounds:

Pen=4-Pentenoyl

|      | R1    | R2    | R5    | R8    | R17   | R18   | Cytotoxicity activity |
|------|-------|-------|-------|-------|-------|-------|-----------|
| E4A  | OH    | OH    | OH    | OH    | OH    | OH    | none      |
| C1   | OH    | OH    | OH    | OH    | O—Pen | OH    | moderate  |
| C2   | OH    | OH    | OH    | OH    | OH    | O—Pen | moderate  |
| C3   | OH    | OH    | OH    | OH    | O—Pen | O—Pen | strong    |
| C4   | O—Pen | OH    | OH    | OH    | O—Pen | O—Pen | moderate  |
| C5   | OH    | O—Pen | OH    | OH    | O—Pen | O—Pen | moderate  |
| C6   | OH    | OH    | O—Pen | OH    | O—Pen | O—Pen | moderate  |
| C7   | OH    | OH    | OH    | O—Pen | O—Pen | O—Pen | moderate  |
| C8   | O—Pen | O—Pen | OH    | OH    | O—Pen | O—Pen | weak      |
| C9   | OH    | O—Pen | O—Pen | OH    | O—Pen | O—Pen | weak      |
| C10  | OH    | OH    | O—Pen | O—Pen | O—Pen | O—Pen | weak      |
| C11  | O—Pen | OH    | O—Pen | OH    | O—Pen | O—Pen | weak      |
| C12  | OH    | O—Pen | OH    | O—Pen | O—Pen | O—Pen | weak      |
| C13  | O—Pen | OH    | OH    | O—Pen | O—Pen | O—Pen | weak      |
| C14  | OH    | O—Pen | O—Pen | OH    | O—Pen | O—Pen | weak      |
| C15  | O—Pen | O—Pen | O—Pen | OH    | O—Pen | O—Pen | weak      |
| C16  | O—Pen | O—Pen | OH    | O—Pen | O—Pen | O—Pen | weak      |
| C17  | O—Pen | OH    | O—Pen | O—Pen | O—Pen | O—Pen | weak      |
| C18  | OH    | O—Pen | O—Pen | O—Pen | O—Pen | O—Pen | weak      |
| C19  | O—Pen | O—Pen | O—Pen | O—Pen | O—Pen | O—Pen | none      |
| C20  | O—Pen | O—Pen | OH    | OH    | OH    | O—Pen | moderate  |
| C21  | O—Pen | O—Pen | OH    | OH    | O—Pen | OH    | moderate  |
| C22  | O—Pen | O—Pen | OH    | O—Pen | OH    | OH    | moderate  |
| C23  | O—Pen | O—Pen | O—Pen | OH    | OH    | OH    | moderate  |
| C24  | O—Pen | O—Pen | OH    | OH    | OH    | OH    | moderate  |
| C25  | O—Pen | OH    | OH    | OH    | OH    | O—Pen | moderate  |
| C26  | OH    | O—Pen | OH    | OH    | OH    | O—Pen | moderate  |
| C27  | OH    | OH    | O—Pen | OH    | OH    | O—Pen | moderate  |
| C28  | OH    | OH    | OH    | O—Pen | OH    | O—Pen | moderate  |
| C29  | O—Pen | OH    | OH    | OH    | O—Pen | OH    | moderate  |
| C30  | OH    | O—Pen | OH    | OH    | O—Pen | OH    | moderate  |
| C31  | OH    | OH    | O—Pen | OH    | O—Pen | OH    | moderate  |
| C32  | OH    | OH    | OH    | O—Pen | O—Pen | OH    | moderate  |

Esterification of core compound E4A with Hexanoyl chloride and isolation of the compounds with HPLC give the following compounds:

Hex=Hexanoyl

|       | R1    | R2    | R5    | R8    | R17   | R18   | Cytotoxicity activity |
|-------|-------|-------|-------|-------|-------|-------|-----------|
| E4AF  | OH    | OH    | OH    | OH    | OH    | OH    | none      |
| D1    | OH    | OH    | OH    | OH    | O—Hex | OH    | moderate  |
| D2    | OH    | OH    | OH    | OH    | OH    | O—Hex | moderate  |
| D3    | OH    | OH    | OH    | OH    | O—Hex | O—Hex | strong    |
| D4    | O—Hex | OH    | OH    | OH    | O—Hex | O—Hex | moderate  |
| D5    | OH    | O—Hex | OH    | OH    | O—Hex | O—Hex | moderate  |
| D6    | OH    | OH    | O—Hex | OH    | O—Hex | O—Hex | moderate  |
| D7    | OH    | OH    | OH    | O—Hex | O—Hex | O—Hex | moderate  |
| D8    | O—Hex | O—Hex | OH    | OH    | O—Hex | O—Hex | weak      |
| D9    | OH    | O—Hex | O—Hex | OH    | O—Hex | O—Hex | weak      |
| D10   | OH    | OH    | O—Hex | O—Hex | O—Hex | O—Hex | weak      |
| D11   | O—Hex | OH    | O—Hex | OH    | O—Hex | O—Hex | weak      |
| D12   | OH    | O—Hex | OH    | O—Hex | O—Hex | O—Hex | weak      |
| D13   | O—Hex | OH    | OH    | O—Hex | O—Hex | O—Hex | weak      |
| D14   | OH    | O—Hex | O—Hex | OH    | O—Hex | O—Hex | weak      |
| D15   | O—Hex | O—Hex | O—Hex | OH    | O—Hex | O—Hex | weak      |
| D16   | O—Hex | O—Hex | OH    | O—Hex | O—Hex | O—Hex | weak      |
| D17   | O—Hex | OH    | O—Hex | O—Hex | O—Hex | O—Hex | weak      |
| D18   | OH    | O—Hex | O—Hex | O—Hex | O—Hex | O—Hex | weak      |
| D19   | O—Hex | O—Hex | O—Hex | O—Hex | O—Hex | O—Hex | none      |
| D20   | O—Hex | O—Hex | OH    | OH    | OH    | O—Hex | moderate  |
| D21   | O—Hex | O—Hex | OH    | OH    | O—Hex | OH    | moderate  |
| D22   | O—Hex | O—Hex | OH    | O—Hex | OH    | OH    | moderate  |
| D23   | O—Hex | O—Hex | O—Hex | OH    | OH    | OH    | moderate  |
| D24   | O—Hex | O—Hex | OH    | OH    | OH    | OH    | moderate  |
| D25   | O—Hex | OH    | OH    | OH    | OH    | O—Hex | moderate  |
| D26   | OH    | O—Hex | OH    | OH    | OH    | O—Hex | moderate  |
| D27   | OH    | OH    | O—Hex | OH    | OH    | O—Hex | moderate  |
| D28   | OH    | OH    | OH    | O—Hex | OH    | O—Hex | moderate  |
| D29   | O—Hex | OH    | OH    | OH    | O—Hex | OH    | moderate  |
| D30   | OH    | O—Hex | OH    | OH    | O—Hex | OH    | moderate  |
| D31   | OH    | OH    | O—Hex | OH    | O—Hex | OH    | moderate  |
| D32   | OH    | OH    | OH    | O—Hex | O—Hex | OH    | moderate  |

Esterification of core compound E4A with 2-Ethylbutyryl chloride and isolation of the compounds with HPLC give the following compounds:

Eth=2-Ethylbutyryl

| | R1 | R2 | R5 | R8 | R17 | R18 | Cytotoxicity activity |
|---|---|---|---|---|---|---|---|
| E4AF | OH | OH | OH | OH | OH | OH | none |
| E1 | OH | OH | OH | OH | O—Eth | OH | moderate |
| E2 | OH | OH | OH | OH | OH | O—Eth | moderate |
| E3 | OH | OH | OH | OH | O—Eth | O—Eth | strong |
| E4 | O—Eth | OH | OH | OH | O—Eth | O—Eth | moderate |
| E5 | OH | O—Eth | OH | OH | O—Eth | O—Eth | moderate |
| E6 | OH | OH | O—Eth | OH | O—Eth | O—Eth | moderate |
| E7 | OH | OH | OH | O—Eth | O—Eth | O—Eth | moderate |
| E8 | O—Eth | O—Eth | OH | OH | O—Eth | O—Eth | weak |
| E9 | OH | O—Eth | O—Eth | OH | O—Eth | O—Eth | weak |
| E10 | OH | OH | O—Eth | O—Eth | O—Eth | O—Eth | weak |
| E11 | O—Eth | OH | O—Eth | OH | O—Eth | O—Eth | weak |
| E12 | OH | O—Eth | OH | O—Eth | O—Eth | O—Eth | weak |
| E13 | O—Eth | OH | OH | O—Eth | O—Eth | O—Eth | weak |
| E14 | OH | O—Eth | O—Eth | OH | O—Eth | O—Eth | weak |
| E15 | O—Eth | O—Eth | O—Eth | OH | O—Eth | O—Eth | weak |
| E16 | O—Eth | O—Eth | OH | O—Eth | O—Eth | O—Eth | weak |
| E17 | O—Eth | OH | O—Eth | O—Eth | O—Eth | O—Eth | weak |
| E18 | OH | O—Eth | O—Eth | O—Eth | O—Eth | O—Eth | weak |
| E19 | O—Eth | O—Eth | O—Eth | O—Eth | O—Eth | O—Eth | none |
| E20 | O—Eth | O—Eth | OH | OH | OH | O—Eth | moderate |
| E21 | O—Eth | O—Eth | OH | OH | O—Eth | OH | moderate |
| E22 | O—Eth | O—Eth | OH | O—Eth | OH | OH | moderate |
| E23 | O—Eth | O—Eth | O—Eth | OH | OH | OH | moderate |
| E24 | O—Eth | O—Eth | OH | OH | OH | OH | moderate |
| E25 | O—Eth | OH | OH | OH | OH | O—Eth | moderate |
| E26 | OH | O—Eth | OH | OH | OH | O—Eth | moderate |
| E27 | OH | OH | O—Eth | OH | OH | O—Eth | moderate |
| E28 | OH | OH | OH | O—Eth | OH | O—Eth | moderate |
| E29 | O—Eth | OH | OH | OH | O—Eth | OH | moderate |
| E30 | OH | O—Eth | OH | OH | O—Eth | OH | moderate |
| E31 | OH | OH | O—Eth | OH | O—Eth | OH | moderate |
| E32 | OH | OH | OH | O—Eth | O—Eth | OH | moderate |

Esterification of core compound E4A with Acetyl chloride (H) and isolation of the compounds with HPLC give the following compounds:

Acy=Acetyl

| | R1 | R2 | R5 | R8 | R17 | R18 | Cytotoxicity activity |
|---|---|---|---|---|---|---|---|
| E4A | OH | OH | OH | OH | OH | OH | none |
| H1 | OH | OH | OH | OH | O—Acy | OH | moderate |
| H2 | OH | OH | OH | OH | OH | O—Acy | moderate |
| H3 | OH | OH | OH | OH | O—Acy | O—Acy | strong |
| H4 | O—Acy | OH | OH | OH | O—Acy | O—Acy | moderate |
| H5 | OH | O—Acy | OH | OH | O—Acy | O—Acy | moderate |
| H6 | OH | OH | O—Acy | OH | O—Acy | O—Acy | moderate |
| H7 | OH | OH | OH | O—Acy | O—Acy | O—Acy | moderate |
| H8 | O—Acy | O—Acy | OH | OH | O—Acy | O—Acy | weak |
| H9 | OH | O—Acy | O—Acy | OH | O—Acy | O—Acy | weak |
| H10 | OH | OH | O—Acy | O—Acy | O—Acy | O—Acy | weak |
| H11 | O—Acy | OH | O—Acy | OH | O—Acy | O—Acy | weak |
| H12 | OH | O—Acy | OH | O—Acy | O—Acy | O—Acy | weak |
| H13 | O—Acy | OH | OH | O—Acy | O—Acy | O—Acy | weak |
| H14 | OH | O—Acy | O—Acy | OH | O—Acy | O—Acy | weak |
| H15 | O—Acy | O—Acy | O—Acy | OH | O—Acy | O—Acy | weak |
| H16 | O—Acy | O—Acy | OH | O—Acy | O—Acy | O—Acy | weak |
| H17 | O—Acy | OH | O—Acy | O—Acy | O—Acy | O—Acy | weak |
| H18 | OH | O—Acy | O—Acy | O—Acy | O—Acy | O—Acy | weak |
| H19 | O—Acy | O—Acy | O—Acy | O—Acy | O—Acy | O—Acy | none |
| H20 | O—Acy | O—Acy | OH | OH | OH | O—Acy | moderate |
| H21 | O—Acy | O—Acy | OH | OH | O—Acy | OH | moderate |
| H22 | O—Acy | O—Acy | OH | O—Acy | OH | OH | moderate |
| H23 | O—Acy | O—Acy | O—Acy | OH | OH | OH | moderate |
| H24 | O—Acy | O—Acy | OH | OH | OH | OH | moderate |
| H25 | O—Acy | OH | OH | OH | OH | O—Acy | moderate |
| H26 | OH | O—Acy | OH | OH | OH | O—Acy | moderate |
| H27 | OH | OH | O—Acy | OH | OH | O—Acy | moderate |
| H28 | OH | OH | OH | O—Acy | OH | O—Acy | moderate |
| H29 | O—Acy | OH | OH | OH | O—Acy | OH | moderate |
| H30 | OH | O—Acy | OH | OH | O—Acy | OH | moderate |
| H31 | OH | OH | O—Acy | OH | O—Acy | OH | moderate |
| H32 | OH | OH | OH | O—Acy | O—Acy | OH | moderate |

Esterification of core compound E4A with Crotonoyl chloride and isolation of the compounds with HPLC give the following compounds:

Cro=Crotonoyl

| | R1 | R2 | R5 | R8 | R17 | R18 | Cytotoxicity activity |
|---|---|---|---|---|---|---|---|
| E4A | OH | OH | OH | OH | OH | OH | none |
| I1 | OH | OH | OH | OH | O-Cro | OH | moderate |
| I2 | OH | OH | OH | OH | OH | O-Cro | moderate |
| I3 | OH | OH | OH | OH | O-Cro | O-Cro | strong |
| I4 | O-Cro | OH | OH | OH | O-Cro | O-Cro | moderate |
| I5 | OH | O-Cro | OH | OH | O-Cro | O-Cro | moderate |
| I6 | OH | OH | O-Cro | OH | O-Cro | O-Cro | moderate |
| I7 | OH | OH | OH | O-Cro | O-Cro | O-Cro | moderate |

| | R1 | R2 | R5 | R8 | R17 | R18 | Cytotoxicity activity |
|---|---|---|---|---|---|---|---|
| I 8 | O-Cro | O-Cro | OH | OH | O-Cro | O-Cro | weak |
| I 9 | OH | O-Cro | O-Cro | OH | O-Cro | O-Cro | weak |
| I 10 | OH | OH | O-Cro | O-Cro | O-Cro | O-Cro | weak |
| I 11 | O-Cro | OH | O-Cro | OH | O-Cro | O-Cro | weak |
| I 12 | OH | O-Cro | OH | O-Cro | O-Cro | O-Cro | weak |
| I 13 | O-Cro | OH | OH | O-Cro | O-Cro | O-Cro | weak |
| I 14 | OH | O-Cro | O-Cro | OH | O-Cro | O-Cro | weak |
| I 15 | O-Cro | O-Cro | O-Cro | OH | O-Cro | O-Cro | weak |
| I 16 | O-Cro | O-Cro | OH | OH | O-Cro | O-Cro | weak |
| I 17 | O-Cro | OH | O-Cro | O-Cro | O-Cro | O-Cro | weak |
| I 18 | OH | O-Cro | O-Cro | O-Cro | O-Cro | O-Cro | weak |
| I 19 | O-Cro | O-Cro | O-Cro | O-Cro | O-Cro | O-Cro | none |
| I 20 | O-Cro | O-Cro | OH | OH | OH | O-Cro | moderate |
| I 21 | O-Cro | O-Cro | OH | OH | O-Cro | OH | moderate |
| I 22 | O-Cro | O-Cro | OH | O-Cro | OH | OH | moderate |
| I 23 | O-Cro | O-Cro | O-Cro | OH | OH | OH | moderate |
| I 24 | O-Cro | O-Cro | OH | OH | OH | OH | moderate |
| I 25 | O-Cro | OH | OH | OH | OH | O-Cro | moderate |
| I 26 | OH | O-Cro | OH | OH | OH | O-Cro | moderate |
| I 27 | OH | OH | O-Cro | OH | OH | O-Cro | moderate |
| I 28 | OH | OH | OH | O-Cro | OH | O-Cro | moderate |
| I 29 | O-Cro | OH | OH | OH | O-Cro | OH | moderate |
| I 30 | OH | O-Cro | OH | OH | O-Cro | OH | moderate |
| I 31 | OH | OH | O-Cro | OH | O-Cro | OH | moderate |
| I 32 | OH | OH | OH | O-Cro | O-Cro | OH | moderate |

Esterification of core compound E4A with Cinnamoyl chloride and isolation of the compounds with HPLC give the following compounds:

Cin=Cinnamoyl

| | R1 | R2 | R5 | R8 | R17 | R18 | Cytotoxicity activity |
|---|---|---|---|---|---|---|---|
| E4A | OH | OH | OH | OH | OH | OH | none |
| J1 | OH | OH | OH | OH | O-Cin | OH | moderate |
| J2 | OH | OH | OH | OH | OH | O-Cin | moderate |
| J3 | OH | OH | OH | OH | O-Cin | O-Cin | strong |
| J4 | O-Cin | OH | OH | OH | O-Cin | O-Cin | moderate |
| J5 | OH | O-Cin | OH | OH | O-Cin | O-Cin | moderate |
| J6 | OH | OH | O-Cin | OH | O-Cin | O-Cin | moderate |
| J7 | OH | OH | OH | O-Cin | O-Cin | O-Cin | moderate |
| J8 | O-Cin | O-Cin | OH | OH | O-Cin | O-Cin | weak |
| J9 | OH | O-Cin | O-Cin | OH | O-Cin | O-Cin | weak |
| J10 | OH | OH | O-Cin | O-Cin | O-Cin | O-Cin | weak |
| J11 | O-Cin | OH | O-Cin | OH | O-Cin | O-Cin | weak |
| J12 | OH | O-Cin | OH | O-Cin | O-Cin | O-Cin | weak |
| J13 | O-Cin | OH | OH | O-Cin | O-Cin | O-Cin | weak |
| J14 | OH | O-Cin | O-Cin | OH | O-Cin | O-Cin | weak |
| J15 | O-Cin | O-Cin | O-Cin | OH | O-Cin | O-Cin | weak |
| J16 | O-Cin | O-Cin | OH | O-Cin | O-Cin | O-Cin | weak |
| J17 | O-Cin | OH | O-Cin | O-Cin | O-Cin | O-Cin | weak |
| J18 | OH | O-Cin | O-Cin | O-Cin | O-Cin | O-Cin | weak |
| J19 | O-Cin | O-Cin | O-Cin | O-Cin | O-Cin | O-Cin | none |
| J20 | O-Cin | O-Cin | OH | OH | OH | O-Cin | moderate |
| J21 | O-Cin | O-Cin | OH | OH | O-Cin | OH | moderate |
| J22 | O-Cin | O-Cin | OH | O-Cin | OH | OH | moderate |
| J23 | O-Cin | O-Cin | O-Cin | OH | OH | OH | moderate |
| J24 | O-Cin | O-Cin | OH | OH | OH | OH | moderate |
| J25 | O-Cin | OH | OH | OH | OH | O-Cin | moderate |
| J26 | OH | O-Cin | OH | OH | OH | O-Cin | moderate |
| J27 | OH | OH | O-Cin | OH | OH | O-Cin | moderate |
| J28 | OH | OH | OH | O-Cin | OH | O-Cin | moderate |
| J29 | O-Cin | OH | OH | OH | O-Cin | OH | moderate |
| J30 | OH | O-Cin | OH | OH | O-Cin | OH | moderate |
| J31 | OH | OH | O-Cin | OH | O-Cin | OH | moderate |
| J32 | OH | OH | OH | O-Cin | O-Cin | OH | moderate |

Esterification of core compound E4A with benzoyl chloride and isolation of the compounds with HPLC give the following compounds:

Ben=benzoyl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Ben | OH | moderate |
| K2 | OH | OH | OH | OH | OH | O-Ben | moderate |
| K3 | OH | OH | OH | OH | O-Ben | O-Ben | strong |
| K4 | O-Ben | OH | OH | OH | O-Ben | O-Ben | moderate |
| K5 | OH | O-Ben | OH | OH | O-Ben | O-Ben | moderate |
| K6 | OH | OH | O-Ben | OH | O-Ben | O-Ben | moderate |
| K7 | OH | OH | OH | O-Ben | O-Ben | O-Ben | moderate |
| K8 | O-Ben | O-Ben | OH | OH | O-Ben | O-Ben | weak |
| K9 | OH | O-Ben | O-Ben | OH | O-Ben | O-Ben | weak |
| K10 | OH | OH | O-Ben | O-Ben | O-Ben | O-Ben | weak |
| K11 | O-Ben | OH | O-Ben | OH | O-Ben | O-Ben | weak |
| K12 | OH | O-Ben | OH | O-Ben | O-Ben | O-Ben | weak |
| K13 | O-Ben | OH | OH | O-Ben | O-Ben | O-Ben | weak |
| K14 | OH | O-Ben | O-Ben | OH | O-Ben | O-Ben | weak |
| K15 | O-Ben | O-Ben | O-Ben | OH | O-Ben | O-Ben | weak |
| K16 | O-Ben | O-Ben | OH | O-Ben | O-Ben | O-Ben | weak |
| K17 | O-Ben | OH | O-Ben | O-Ben | O-Ben | O-Ben | weak |
| K18 | OH | O-Ben | O-Ben | O-Ben | O-Ben | O-Ben | weak |
| K19 | O-Ben | O-Ben | O-Ben | O-Ben | O-Ben | O-Ben | none |
| K20 | O-Ben | O-Ben | OH | OH | OH | O-Ben | moderate |
| K21 | O-Ben | O-Ben | OH | OH | O-Ben | OH | moderate |
| K22 | O-Ben | O-Ben | OH | O-Ben | OH | OH | moderate |
| K23 | O-Ben | O-Ben | O-Ben | OH | OH | OH | moderate |

-continued

| | R1 | R2 | R5 | R8 | R17 | R18 | Cytotoxicity activity |
|---|---|---|---|---|---|---|---|
| K24 | O-Ben | O-Ben | OH | OH | OH | OH | moderate |
| K25 | O-Ben | OH | OH | OH | OH | O-Ben | moderate |
| K26 | OH | O-Ben | OH | OH | OH | O-Ben | moderate |
| K27 | OH | OH | O-Ben | OH | OH | O-Ben | moderate |
| K28 | OH | OH | OH | O-Ben | OH | O-Ben | moderate |
| K29 | O-Ben | OH | OH | OH | O-Ben | OH | moderate |
| K30 | OH | O-Ben | OH | OH | O-Ben | OH | moderate |
| K31 | OH | OH | O-Ben | OH | O-Ben | OH | moderate |
| K32 | OH | OH | OH | O-Ben | O-Ben | OH | moderate |

Esterification of E4A-Tig-N with senecioyl chloride and isolation of the compounds with HPLC give the following compounds:

| | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Sen-1 | OH | OH | OH | OH | O-Tig | O-Sen | strong |
| Tig-Sen-2 | O-Sen | OH | OH | OH | O-Tig | O-Sen | moderate |
| Tig-Sen-3 | OH | O-Sen | OH | OH | O-Tig | O-Sen | moderate |
| Tig-Sen-4 | OH | OH | O-Sen | OH | O-Tig | O-Sen | moderate |
| Tig-Sen-5 | O-Sen | OH | OH | OH | O-Tig | OH | moderate |
| Tig-Sen-6 | OH | O-Sen | OH | OH | O-Tig | OH | moderate |

Esterification of E4A-Tig-N with Crotonoyl chloride and isolation of the compounds with HPLC give the following compounds:

| | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Cro-1 | OH | OH | OH | OH | O-Tig | O-Cro | strong |
| Tig-Cro-2 | O-Cro | OH | OH | OH | O-Tig | O-Cro | moderate |
| Tig-Cro-3 | OH | O-Cro | OH | OH | O-Tig | O-Cro | moderate |
| Tig-Cro-4 | OH | OH | O-Cro | OH | O-Tig | O-Cro | moderate |
| Tig-Cro-5 | O-Cro | OH | OH | OH | O-Tig | OH | moderate |
| Tig-Cro-6 | OH | O-Cro | OH | OH | O-Tig | OH | moderate |

Esterification of E4A-Tig-N with Acetyl chloride and isolation of the compounds with HPLC give the following compounds:

| | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Acy-1 | OH | OH | OH | OH | O-Tig | O—Acy | strong |
| Tig-Acy-2 | O—Acy | OH | OH | OH | O-Tig | O—Acy | moderate |
| Tig-Acy-3 | OH | O—Acy | OH | OH | O-Tig | O—Acy | moderate |
| Tig-Acy-4 | OH | OH | O—Acy | OH | O-Tig | O—Acy | moderate |
| Tig-Acy-5 | O—Acy | OH | OH | OH | O-Tig | OH | moderate |
| Tig-Acy-6 | OH | O—Acy | OH | OH | O-Tig | OH | moderate |

Esterification of E4A-Tig-N with 4-Pentenoyl chloride and isolation of the compounds with HPLC give the following compounds:

| | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Pen-1 | OH | OH | OH | OH | O-Tig | O—Pen | strong |
| Tig-Pen-2 | O—Pen | OH | OH | OH | O-Tig | O—Pen | moderate |
| Tig-Pen-3 | OH | O—Pen | OH | OH | O-Tig | O—Pen | moderate |
| Tig-Pen-4 | OH | OH | O—Pen | OH | O-Tig | O—Pen | moderate |
| Tig-Pen-5 | O—Pen | OH | OH | OH | O-Tig | OH | moderate |
| Tig-Pen-6 | OH | O—Pen | OH | OH | O-Tig | OH | moderate |

Esterification of E4A-Tig-N with Hexanoly chloride and isolation of the compounds with HPLC give the following compounds:

| | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Hex-1 | OH | OH | OH | OH | O-Tig | O—Hex | strong |
| Tig-Hex-2 | O—Hex | OH | OH | OH | O-Tig | O—Hex | moderate |
| Tig-Hex-3 | OH | O—Hex | OH | OH | O-Tig | O—Hex | moderate |
| Tig-Hex-4 | OH | OH | O—Hex | OH | O-Tig | O—Hex | moderate |
| Tig-Hex-5 | O—Hex | OH | OH | OH | O-Tig | OH | moderate |
| Tig-Hex-6 | OH | O—Hex | OH | OH | O-Tig | OH | moderate |

Esterification of E4A-Tig-N with Cinnamoyl chloride and isolation of the compounds with HPLC give the following compounds:

| | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Cin-1 | OH | OH | OH | OH | O-Tig | O-Cin | strong |
| Tig-Cin-2 | O-Cin | OH | OH | OH | O-Tig | O-Cin | moderate |
| Tig-Cin-3 | OH | O-Cin | OH | OH | O-Tig | O-Cin | moderate |
| Tig-Cin-4 | OH | OH | O-Cin | OH | O-Tig | O-Cin | moderate |
| Tig-Cin-5 | O-Cin | OH | OH | OH | O-Tig | OH | moderate |
| Tig-Cin-6 | OH | O-Cin | OH | OH | O-Tig | OH | moderate |

Esterification of E4A-Tig-N with Angeloyl chloride and isolation of the compounds with HPLC give the following compounds:

| | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Ang-1 | OH | OH | OH | OH | O-Tig | O-Ang | strong |
| Tig-Ang-2 | O-Ang | OH | OH | OH | O-Tig | O-Ang | moderate |
| Tig-Ang-3 | OH | O-Ang | OH | OH | O-Tig | O-Ang | moderate |
| Tig-Ang-4 | OH | OH | O-Ang | OH | O-Tig | O-Ang | moderate |
| Tig-Ang-5 | O-Ang | OH | OH | OH | O-Tig | OH | moderate |
| Tig-Ang-6 | OH | O-Ang | OH | OH | O-Tig | OH | moderate |

Esterification of E4A-Tig-N with 2-Ethylbutyryl chloride and isolation of the compounds with HPLC give the following compounds:

| | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Eth-1 | OH | OH | OH | OH | O-Tig | O—Eth | strong |
| Tig-Eth-2 | O—Eth | OH | OH | OH | O-Tig | O—Eth | moderate |
| Tig-Eth-3 | OH | O—Eth | OH | OH | O-Tig | O—Eth | moderate |
| Tig-Eth-4 | OH | OH | O—Eth | OH | O-Tig | O—Eth | moderate |
| Tig-Eth-5 | O—Eth | OH | OH | OH | O-Tig | OH | moderate |
| Tig-Eth-6 | OH | O—Eth | OH | OH | O-Tig | OH | moderate |

Esterification of compound (A), (B), (C), (D), (E), (F), (G), (H) with acyl chloride including Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride or Ethylbutyryl chloride The compounds vary in composition when the time or temperature of the reaction is changed. The peaks, fractions and compounds are selected according to the activities of times studies and the changes of peaks. The compounds having strong to weak activities are selected and isolated. The anti cancer activities are the MTT studies of bone (U2OS), lung (H460), bladder (HTB-9), ovary (ES2), colon (HCT116), pancreas (Capan), ovary (OVCAR3), prostate (DU145), skin (SK-Mel-5), mouth (KB), kidney (A498), breast (MCF-7), liver (HepG2), brain (T98G), leukemia (K562), cervix (HeLa). The active esterification products are purified with HPLC. The reaction product of mixtures and individual compounds are tested with MTT Cytotoxic Assay. Details of method are in Experiment 3 of the present application. A second esterification of compound can be selected from the above experiment results to produce new active compounds. A partial esterification compound is selected from the above experiments to perform a second or repeated with a third esterification with different acyl chloride in order to produce new active compounds with the experiments in the present application.

A method is 1) Dissolving core compound or triterpenes core, hydroxylated triterpenes core in pyridine; 2) Adding acyl chloride; 3, The mixture is stirred for length of time including 5 sec, 1 min, 2 min, 5 min, 10 min, 30 min, 1 hr, 2 hr, 18 hr, 2 days or 3 days at different temperature; 4) At the end of reaction, aqueous solution of acid or weak base, or water is added to the reaction mixture; 5) The solution is then extracted of ethyl acetate and lyophilization; 6) Dissolving the reaction product in acetonitrile with Trifluoroacetic acid or DMSO; 7) Testing the reaction product of mixtures and individual fractions with MTT cytotoxic assay; 8) Selecting the HPLC fractions for isolation is according to the cytotoxic activity of the reaction product obtained at a specific reaction time; 10) Purifying the active esterification products with HPLC; 11) Collecting the products; 12) Testing the products; wherein the core compound is terpene, isoprene, or triterpene core or hydroxylated triterpenes core; wherein the core compound was dissolved in pyridine; wherein the acyl chloride including Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride and Ethylbutyryl chloride; wherein the reaction time for the mixture is stirred for 5 sec, 1 min, 2 min, 5 min, 10 min, 30 min, 1 hr, 2 hr, 18 hr, 2 days or 3 days; wherein the temperature is 0 C, 25 C, 50 or 75 C temperature; wherein the acid including HCl or the base including NaHCO3 is added to the reaction mixture; wherein the solution is then extracted 3 times with ethyl acetate and lyophilization; wherein the reaction product is dissolved in 80% acetonitrile-0.005% Trifluoroacetic acid or DMSO; wherein selecting the HPLC fractions for isolation is according to the cytotoxic activity of the reaction product obtained at a reaction time of 5 sec, 1 min, 2 min, 5 min, 10 min, 30 min, 1 hr, 2 hr, 18 hr, 2 days or 3 days. In an embodiment, the reaction time may be over 3 days. In an embodiment, the experiment may be performed under 0 C. In an embodiment, the experiment may be performed over 75 C.

The anti cancer activities of Tig-R compound: IC50 of bone (U2OS) is 4.5 ug/ml, lung (H460) is 4.8 ug/ml, bladder (HTB-9) is 2.5 ug/ml, ovary (ES2) is 2.8 ug/ml, colon (HCT116) is 5.2 ug/ml, pancreas (Capan) 2.4 ug/ml, ovary (OVCAR3) is 5.8, prostate (DU145) is 3.6 ug/ml, skin (SK-Mel-5) is 5.1 ug/ml, mouth (KB) is 3 ug/ml, kidney (A498) is 3.5 ug/ml, breast (MCF-7) is 4.5 ug/ml, liver (HepG2) is 6 ug/ml, brain (T98G) is 8 ug/ml), leukemia (K562) is 2 ug/ml, cervix (HeLa) is 5 ug/ml.

The anti cancer activities of Tig-V compound: IC50 of bone (U2OS) is 7 ug/ml, lung (H460) is 6.8 ug/ml, bladder (HTB-9) is 4 ug/ml, ovary (ES2) is 2 ug/ml, colon (HCT116) is 8 ug/ml, pancreas (Capan) 5 ug/ml, ovary (OVCAR3) is 9, prostate (DU145) is 4 ug/ml, skin (SK-MeI-5) is 6 ug/ml, mouth (KB) is 4.5 ug/ml, kidney (A498) is 4.8 ug/ml, breast (MCF-7) is 9 ug/ml, liver (HepG2) is 12 ug/ml, brain (T98G) is 14 ug/ml), leukemia (K562) is 4 ug/ml, cervix (HeLa) is 7 ug/ml.

The anti cancer activities of Tig-N compound: IC50 of bone (U2OS) is 15 ug/ml, lung (H460) is 13 ug/ml, bladder (HTB-9) is 7.5 ug/ml, ovary (ES2) is 9 ug/ml, colon (HCT116) is 15 ug/ml, pancreas (Capan) 8 ug/ml, ovary (OVCAR3) is 18, prostate (DU145) is 4.8 ug/ml, skin (SK-MeI-5) is 15 ug/ml, mouth (KB) is 9 ug/ml, kidney (A498) is 11 ug/ml, breast (MCF-7) is 13 ug/ml, liver (HepG2) is 18 ug/ml, brain (T98G) is 19 ug/ml), leukemia (K562) is 6 ug/ml, cervix (HeLa) is 15 ug/ml.

The anti cancer activities of Tig-Q compound: IC50 of bone (U2OS) is 20 ug/ml, lung (H460) is 18 ug/ml, bladder (HTB-9) is 10 ug/ml, ovary (ES2) is 12 ug/ml, colon (HCT116) is 22 ug/ml, pancreas (Capan) 9 ug/ml, ovary (OVCAR3) is 23, prostate (DU145) is 15 ug/ml, skin (SK-MeI-5) is 20 ug/ml, mouth (KB) is 12 ug/ml, kidney (A498) is 13 ug/ml, breast (MCF-7) is 18 ug/ml, liver (HepG2) is 24 ug/ml, brain (T98G) is 29 ug/ml), leukemia (K562) is 6 ug/ml, cervix (HeLa) is 20 ug/ml.

The anti cancer activities of Tig-T compound: IC50 of bone (U2OS) is 20 ug/ml, lung (H460) is 21 ug/ml, bladder (HTB-9) is 12 ug/ml, ovary (ES2) is 14 ug/ml, colon (HCT116) is 23 ug/ml, pancreas (Capan) 10 ug/ml, ovary (OVCAR3) is 25, prostate (DU145) is 16 ug/ml, skin (SK-MeI-5) is 22 ug/ml, mouth (KB) is 13 ug/ml, kidney (A498) is 15 ug/ml, breast (MCF-7) is 20 ug/ml, liver (HepG2) is 26 ug/ml, brain (T98G) is 26 ug/ml), leukemia (K562) is 9 ug/ml, cervix (HeLa) is 18 ug/ml.

The anti cancer activities of Tig-S compound: IC50 of bone (U2OS) is 5.2 ug/ml, lung (H460) is 5.6 ug/ml, bladder (HTB-9) is 3.5 ug/ml, ovary (ES2) is 4.2 ug/ml, colon (HCT116) is 6.6 ug/ml, pancreas (Capan) 2.9 ug/ml, ovary (OVCAR3) is 6.5, prostate (DU145) is 4.3 ug/ml, skin (SK-MeI-5) is 5.8 ug/ml, mouth (KB) is 4 ug/ml, kidney (A498) is 4.8 ug/ml, breast (MCF-7) is 6.3 ug/ml, liver (HepG2) is 8.5 ug/ml, brain (T98G) is 9 ug/ml), leukemia (K562) is 4.3 ug/ml, cervix (HeLa) is 7 ug/ml.

The anti cancer activities of Tig-U compound: IC50 of bone (U2OS) is 23 ug/ml, lung (H460) is 19 ug/ml, bladder (HTB-9) is 15 ug/ml, ovary (ES2) is 17 ug/ml, colon (HCT116) is 26 ug/ml, pancreas (Capan) 9 ug/ml, ovary (OVCAR3) is 27, prostate (DU145) is 15 ug/ml, skin (SK-MeI-5) is 24 ug/ml, mouth (KB) is 16 ug/ml, kidney (A498) is 18 ug/ml, breast (MCF-7) is 25 ug/ml, liver (HepG2) is 23 ug/ml, brain (T98G) is 22 ug/ml), leukemia (K562) is 10 ug/ml, cervix (HeLa) is 17 ug/ml.

This invention provides compounds, methods, or uses of a compound for the manufacture of a medicament, or uses of a compound for medicament selected from formula (2A), for treating cancer, inhibiting cancer growth, inhibiting cancer invasion, inhibiting cancer metastasis, modulating cell adhesion, modulating cell attachment, using compounds selected from the following:

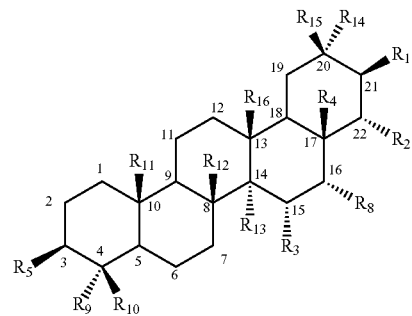

(2A)

$R_1, R_2, R_3, R_4, R_5, R_8, R_9, R_{10}, R_{11}, R_{12}, R_{13}, R_{14}, R_{15}$ are independently selected from the group of hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, alkane, alkene and sugar moiety or derivatives thereof; wherein the structure (2A) comprises at least 2 groups selected from O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl; or wherein R1 and R2 are selected from O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl; In an embodiment, wherein the R1 and R2 are attached OH. In an embodiment, wherein R4, R10 are attached a CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, or CH2O-Ethylbutyryl. In an embodiment, wherein the R3 and R8 is hydrogen or hydroxyl, In an embodiment, wherein the R9, R11, R12, R13, R14, R15 are independently attached with a methyl. In an embodiment, wherein R4 represents CH3, CHO, CH2R6 or CORE, wherein R6 is selected from hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; In an embodiment, wherein R3 is H or OH; In an embodiment, wherein R8 is H or OH; In an embodiment, wherein R16 is H, CH3, OH, or R4 and R16 may together form —CH2-X—, CH(OH)—X— or C(=O)—X—, wherein the —X— may be O or NH or S; wherein when the C12-13 of ring 3 of the triterpene has a double bond then R16 is absent. In an embodiment, wherein R10 represents CH3, CHO, or CH$_2$R6, wherein R6 is selected from hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof;

In an embodiment, wherein R5 is a hydrogen, hydroxyl, heterocyclic or O-sugar moiety(ies), wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combinations thereof; wherein R9, R10, R11, R12, R13, R14, R15 are independently attached a group selecting from CH$_3$, CH$_2$OH, CHO, COOH, COO-alkyl, COO-aryl, COO-heterocyclic, COO-heteroaryl, CH$_2$Oaryl, CH$_2$O-heterocyclic, CH$_2$O-heteroaryl, alkyls group, hydroxyl, acetyl group; wherein R4 and R16 form a divalent radical of formula CH2O, CH(OR7)O, or COOR7, wherein R7 is hydrogen, alkyl, angeloyl, tigloyl, senecioyl, dibenzoyl, benzoyl, alkanoyl, alkenoyl, benzoyl alkyl substituted alkanoyl, aryl, acyl, heterocyclic, heteroraryl, and derivatives thereof; wherein at least two of R1, R2 and R6 are attached a group selected from O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-dibenzoyl, O-benzoyl, O-alkanoyl, O-alkenoyl, O-benzoyl alkyl substituted O-alkanoyl, O-aryl, O-acyl, O-heterocylic, O-heteroraryl, and derivatives thereof; or at least one of R1, R2, and R4 is a sugar moiety having at least two groups selected from a group consisting of angeloyl, acetyl, tigloyl, senecioyl, Crotonoyl, 3,3-Dimethylartyloyl, Cinnamoyl, Pentenoyl, Hexanoyl, benzoyl, Ethylbutyryl, benzoyl, dibenzoyl, alkanoyl, alkenoyl, benzoyl alkyl substituted alkanoyl, aryl, acyl, heterocyclic, heteroraryl, and their derivatives thereof; or wherein R4 represents CH$_2$R6, wherein R6 is selected from hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof; wherein R5 is/are the sugar moiety(ies) selected from the following sugars and alduronic acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, In an embodiment, wherein R5 is a hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof. In an embodiment, R1, R2, R3, R4, R5, R8, R9, R10, R11, R12, R13, R14 or R15 comprise of one or more sugar moieties. In an embodiment, R1, R2, R3, R4, R5, R8, R9, R10, R11, R12, R13, R14 or R15 comprise of one or more acids. In an embodiment, at least 1, or 2, or 3, or 4 of R1, R2, R3, R4, R5, R8, R9, R10, R11, R12, R13, R14 and R15 is hydroxyl. In an embodiment, at least 2, or 3, or 4, or 5, or 6, or 7 of R1, R2, R3, R4, R5, R8, R9, R10, R11, R12, R13, R14 and R15 are independently attached a group selected from the group of O-acetyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, alkane, alkene and derivatives thereof, wherein the group is attached to the triterpene directly or by connecting moiety(ies); In an embodiment, at least 1 or 2, or 3, or 4, or 5, or 6, or 7 of R1, R2, R3, R4, R5, R8 and R10 are independently attached a group selected from the group of O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, and derivatives thereof, wherein the group is attached to the triterpene directly or by connecting moiety(ies). In an embodiment, the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer; wherein the cells comprise breast cell, leukocytic cell, liver cell, ovarian cell, bladder cell, prostatic cell, skin cell, bone cell, brain cell, leukemia cell, lung cell, colon cell, CNS cell, melanoma cell, renal cell, cervical cell, esophageal cell, testicular cell, spleenic cell, kidney cell, lymphatic cell, pancreatic cell, stomach cell and thyroid cell. In an embodiment, the compound is selected from the structure:

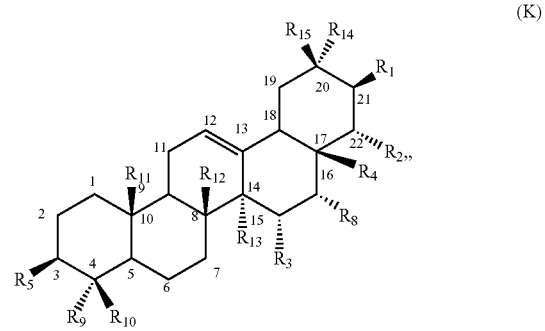

(K)

R1, R2, R3, R4, R5, R8, R9, R10, R11, R12, R13, R14, R15 are independently selected from the group of CH3, CH2OH, hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, alkane, alkene and sugar moiety or derivatives thereof; or wherein any 1 or 2 or 3 or 4 of R1, R2, R3, R4, R5, R8 and R10 are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl; R9, R11, R12, R13, R14, R15 are independently attached a CH3; or wherein R10 is attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl; or wherein R4 and R10 are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl; wherein R3 is OH or H or absent; wherein R1, R2, R3, R5, R8 are OH or H or absent; wherein R9, R11, R12, R13, R14, and R15 are CH3; or wherein R1, R2, R5, R8 represent OH; R3 represents OH, H or absent; R4, R10 represent CH2O angeloyl; R9, R11, R12, R13, R14, R15 represent CH3; or wherein R1, R2, R5, R8 represent OH or O-tigloyl; R3 represents OH, H, or absent; R4, R10 represent CH2O tigloyl; R9, R11, R12, R13, R14, R15 represent CH3; wherein the group attaching to the core compound selected from acetyl, angeloyl, tigloyl, senecioyl, Crotonoyl, O-3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl and alkenylcarbonyl are interchangeable. They can be the same group or in combination thereof. Substitution, deletion and/or addition of any group in the above-described compounds by other group(s) will be apparent to one of ordinary skill in the art based on the teachings of this application. In a further embodiment, the substitution, deletion and/or addition of the group(s) in the compound of the invention does not substantially affect the biological function of the compound.

In an embodiment, the compound is selected from the structures:

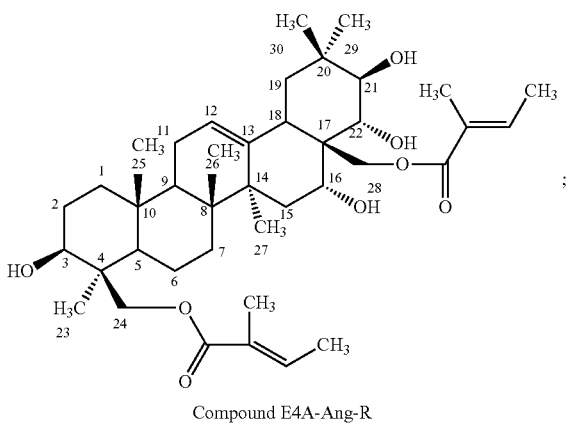

Compound E4A-Ang-R

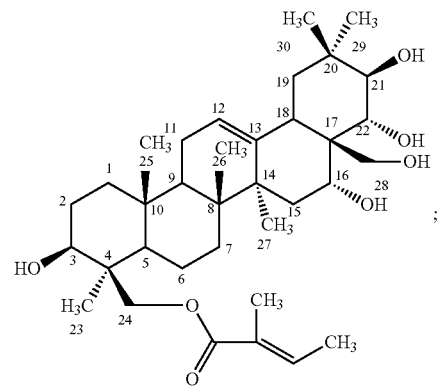

Compound E4A-Ang-N

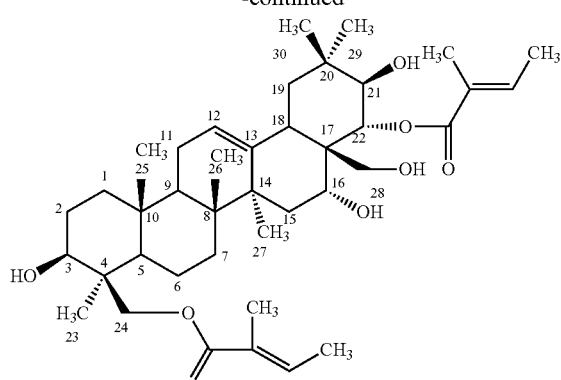
Compound E4A-Ang-Q
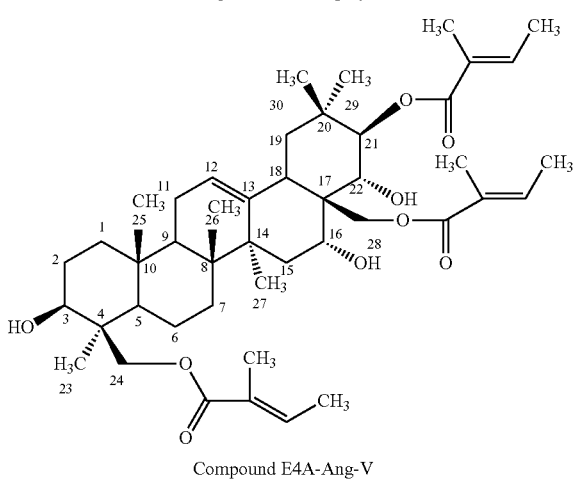
Compound E4A-Ang-V
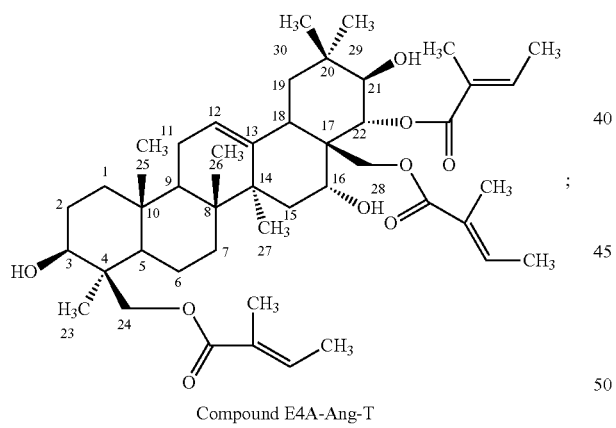
Compound E4A-Ang-T
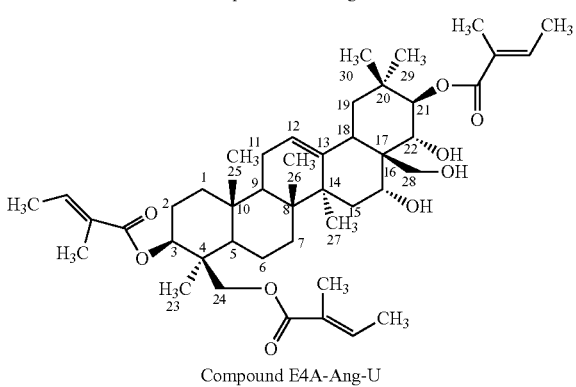
Compound E4A-Ang-U
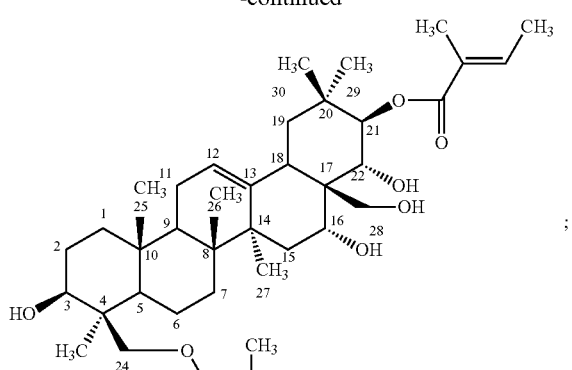
Compound E4A-Ang-S
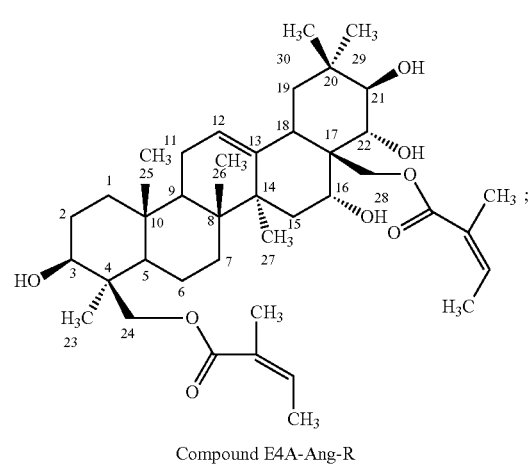
Compound E4A-Ang-R
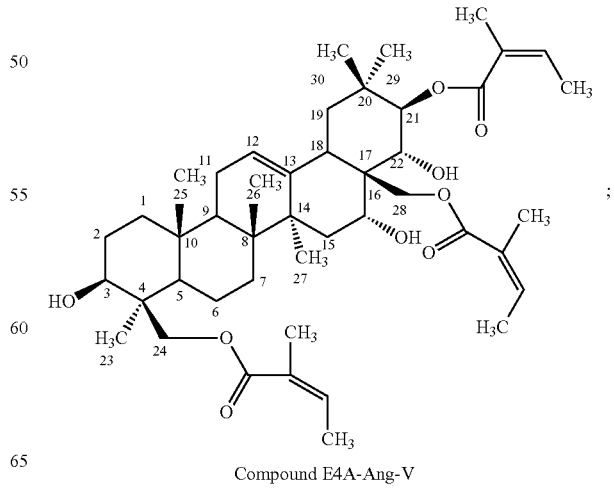
Compound E4A-Ang-V -continued
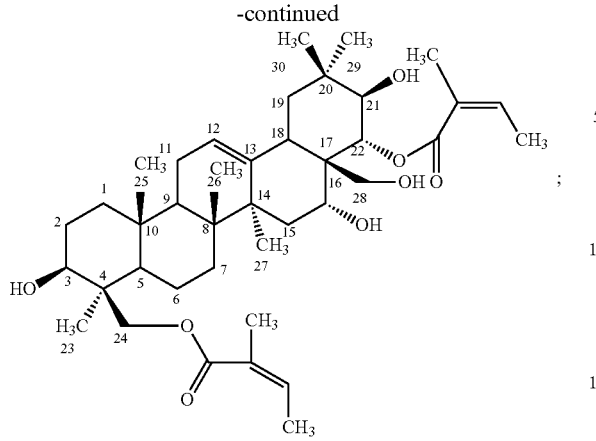
Compound E4A-Ang-Q:
Compound E4A-Ang-N:
Compound E4A-Ang-T:
Compound E4A-Ang-U
Compound E4A-Ang-S:
Compound E4A-Sen-R -continued
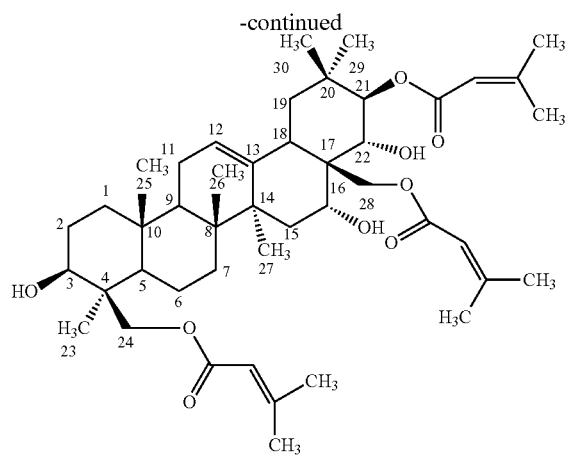
Compound E4A-Sen-V:
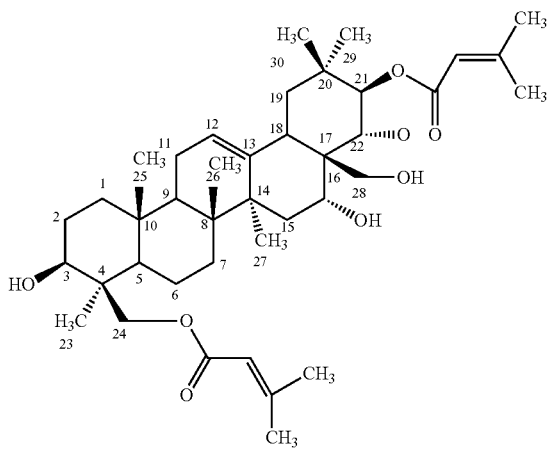
Compound E4A-Sen-S
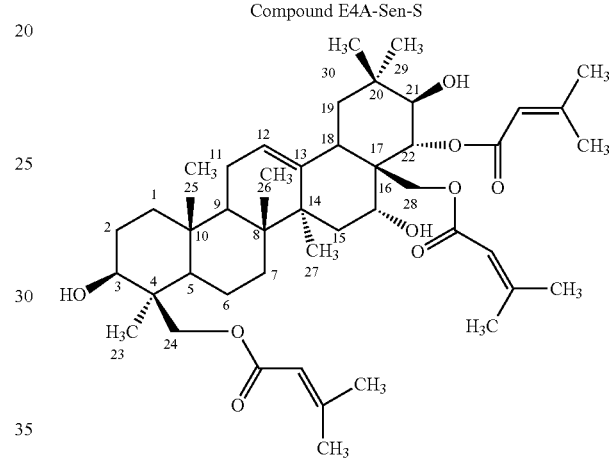
Compound E4A-Sen-T:
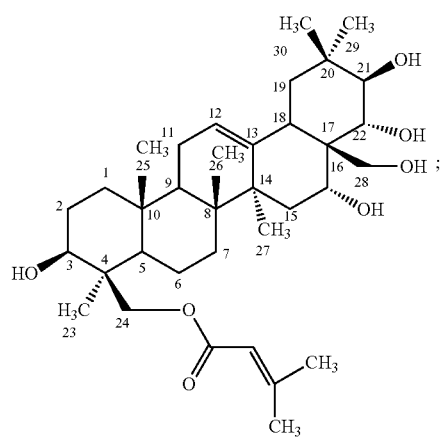
Compound E4A-Sen-N:
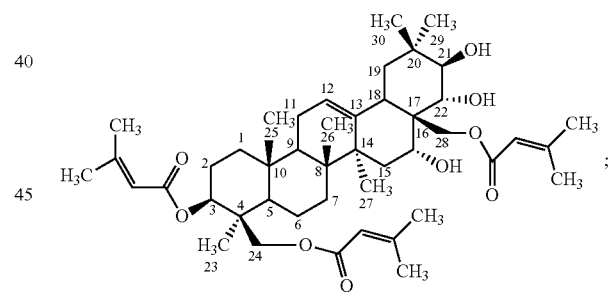
Compound E4A-Sen-U:
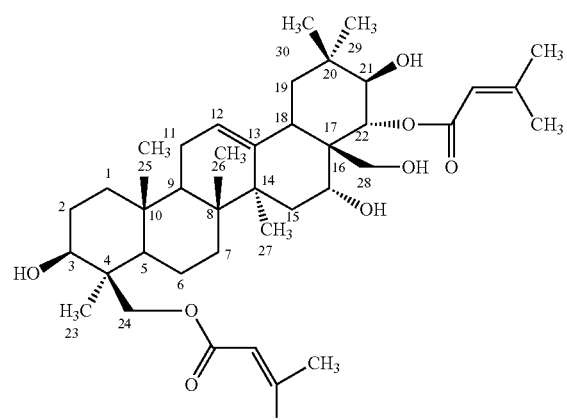
Compound E4A-Sen-Q:
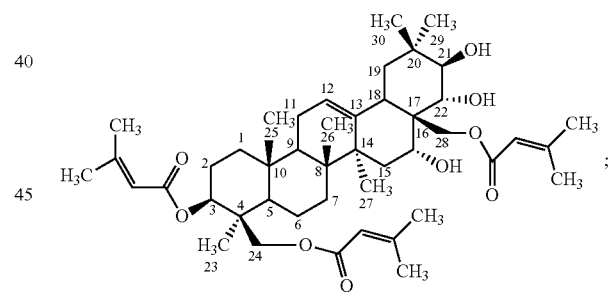
Compound E4A-Cro-R:

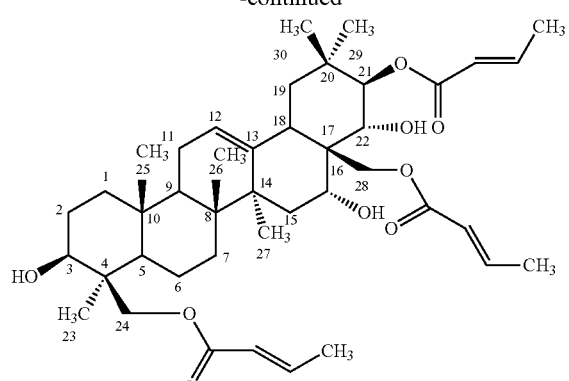
Compound E4A-Cro-V
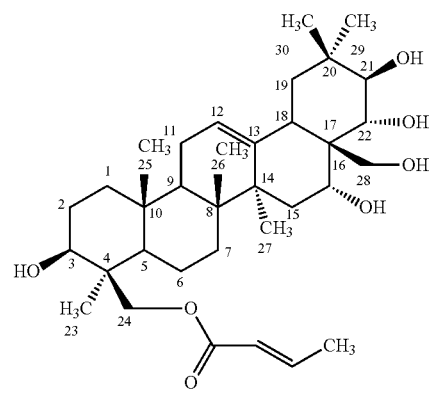
Compound E4A-Cro-N:
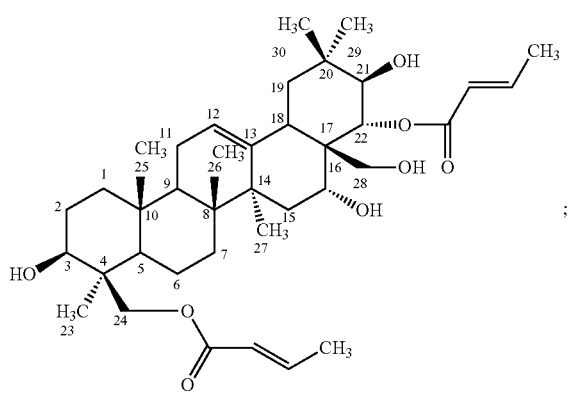
Compound E4A-Cro-Q:
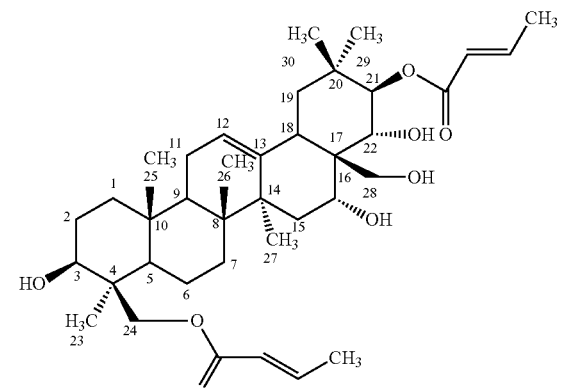
Compound E4A-Cro-S:
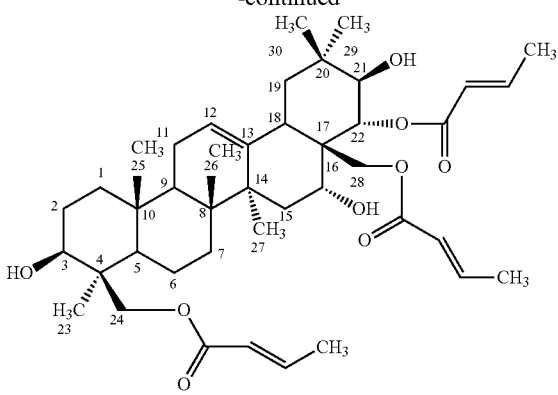
Compound E4A-Cro-T:
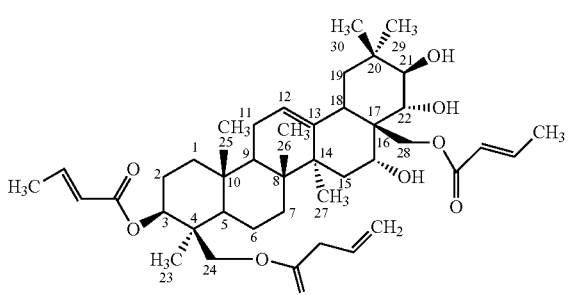
Compound E4A-Cro-U:
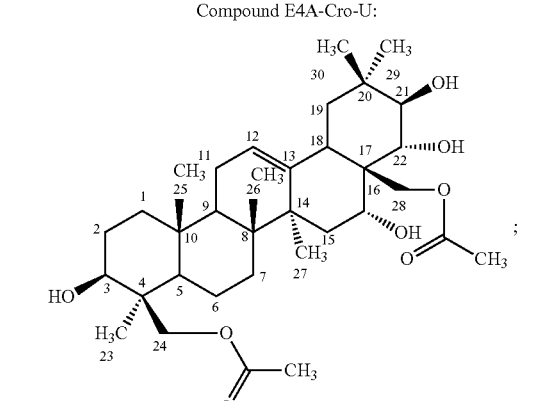
Compound E4A-Acy-R:
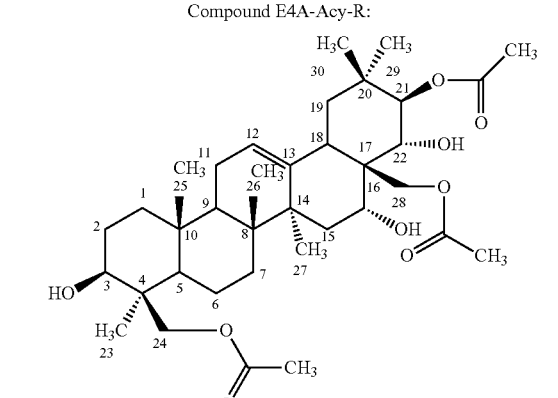
Compound E4A-Acy-V:

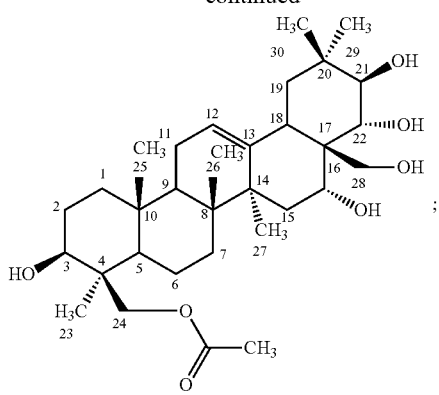
Compound E4A-Acy-N:
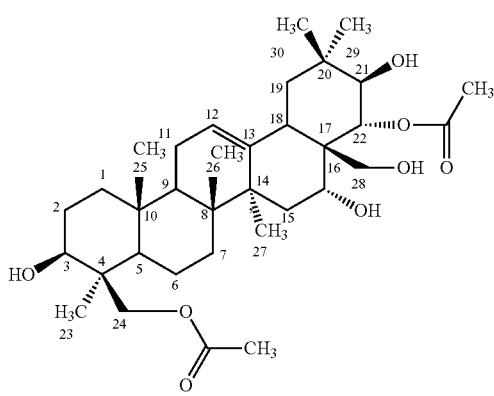
Compound E4A-Acy-Q:
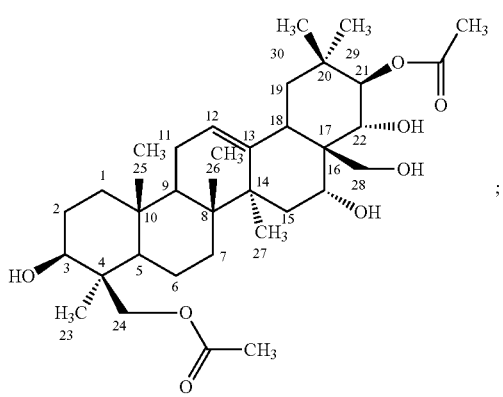
Compound E4A-Acy-S:
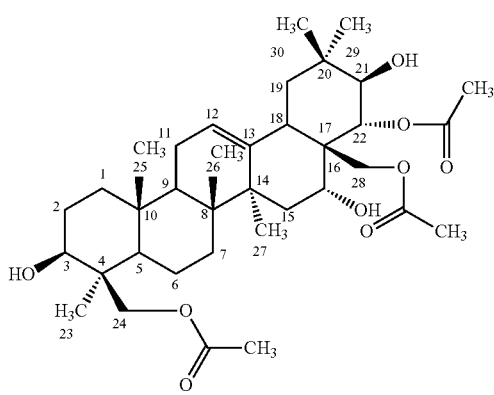
Compound E4A-Acy-T:
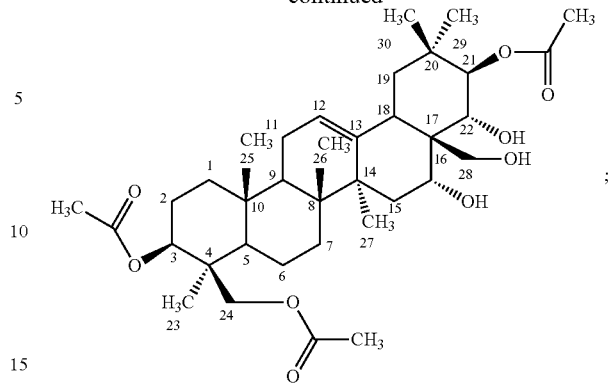
Compound E4A-Acy-U:
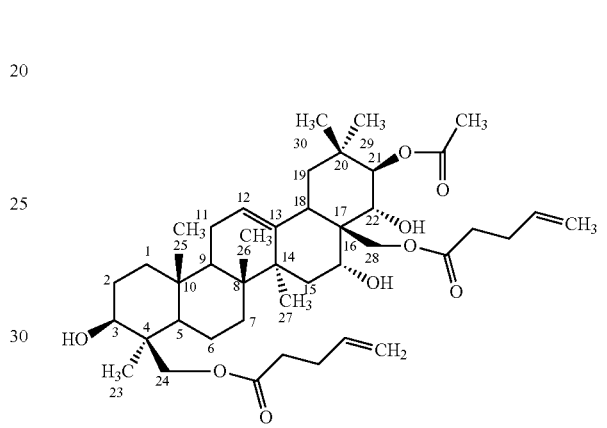
Compound E4A-Pen-R:
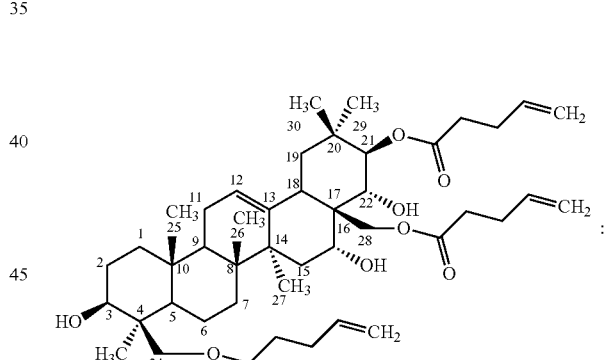
Compound E4A-Pen-V:
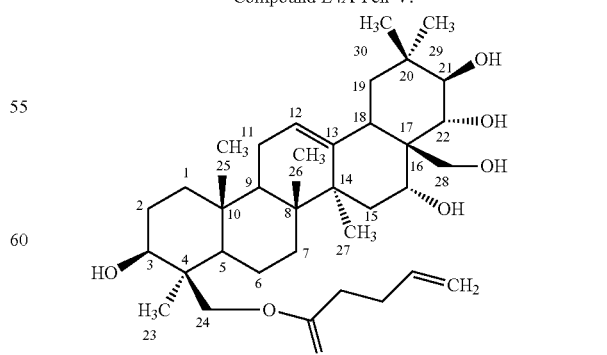
Compound E4A-Pen-N:

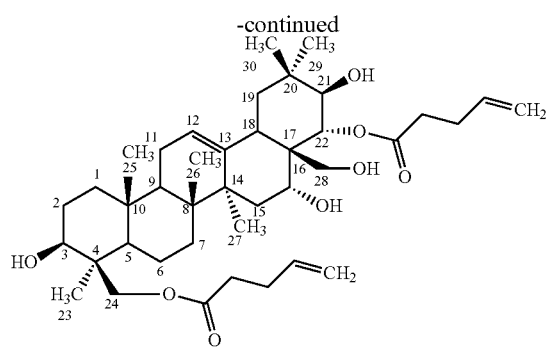
Compound E4A-Pen-Q:
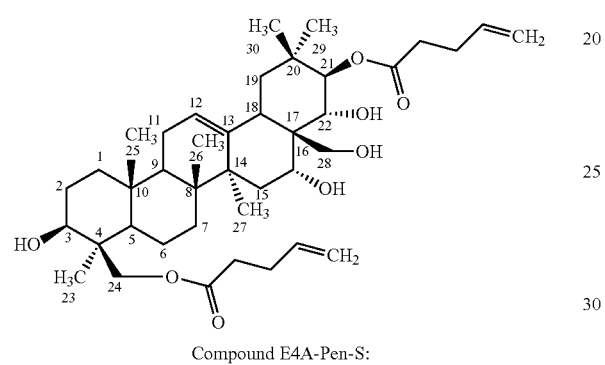
Compound E4A-Pen-S:
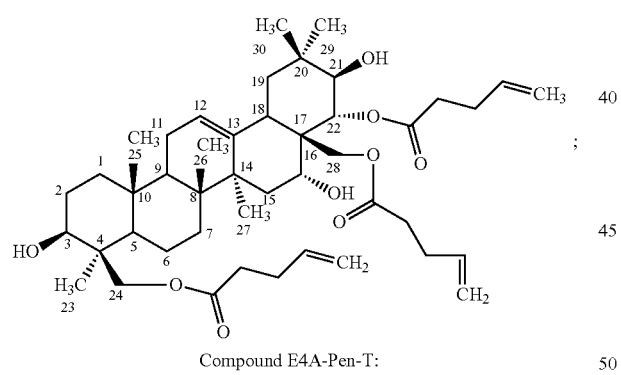
Compound E4A-Pen-T:
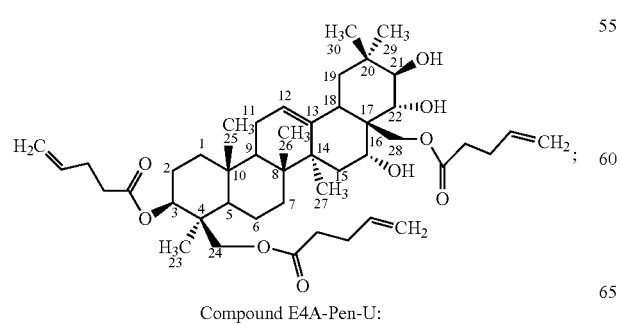
Compound E4A-Pen-U:
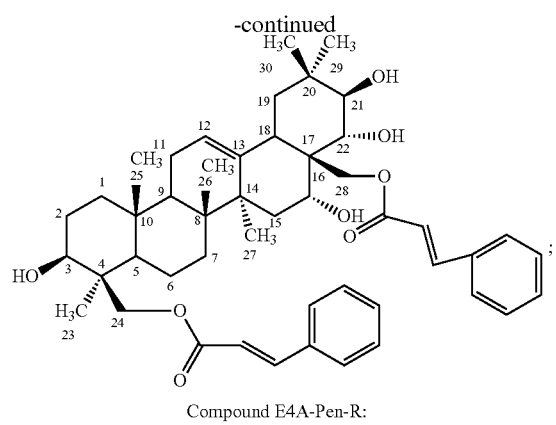
Compound E4A-Pen-R:
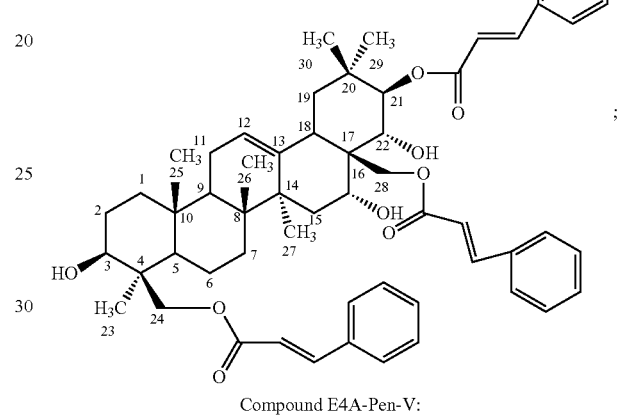
Compound E4A-Pen-V:
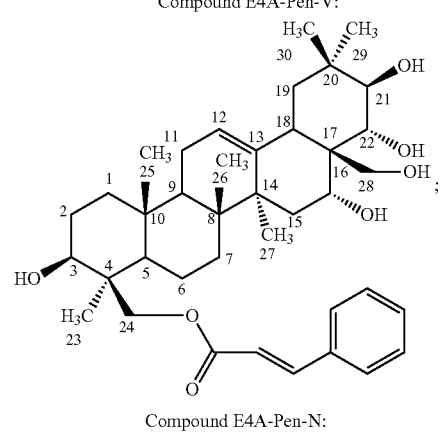
Compound E4A-Pen-N:
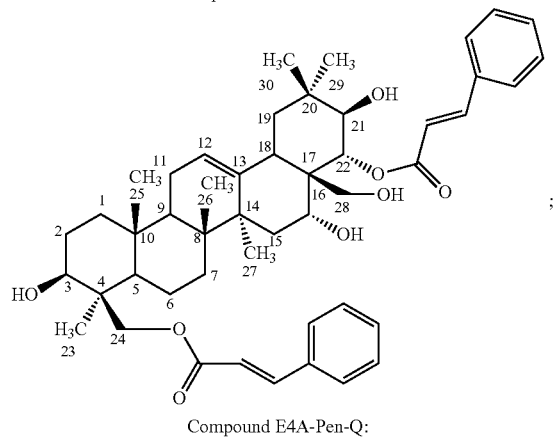
Compound E4A-Pen-Q:

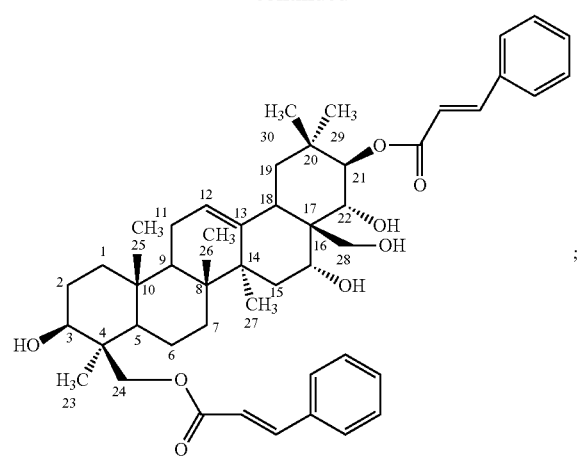
Compound E4A-Pen-S;
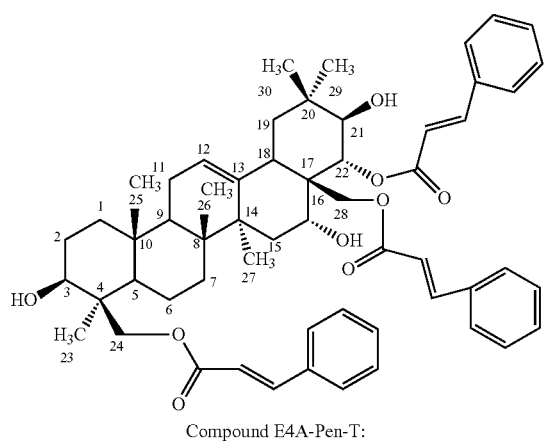
Compound E4A-Pen-T;
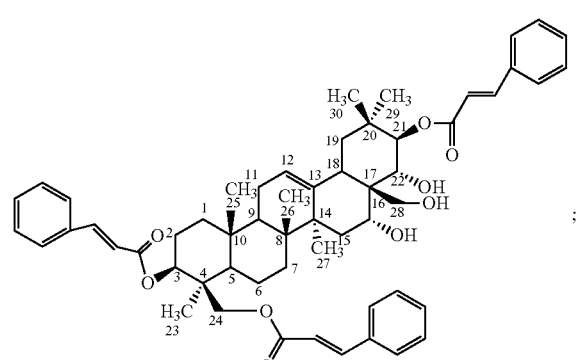
Compound E4A-Cin-U;
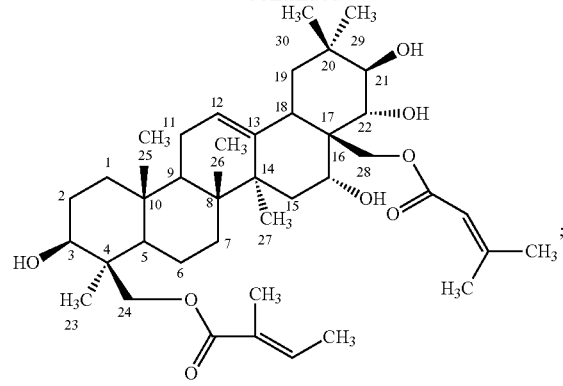
Tig-Sen-1
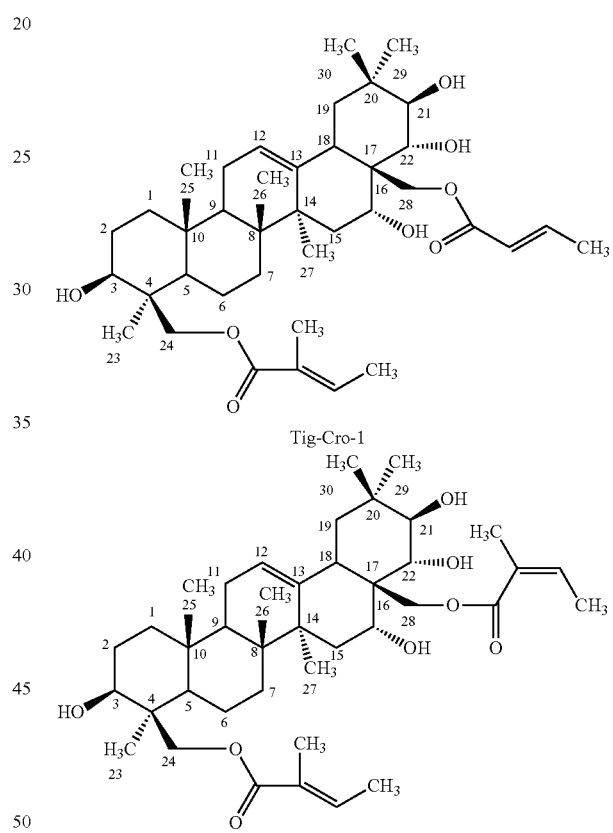
Tig-Cro-1
Tig-Ang-1
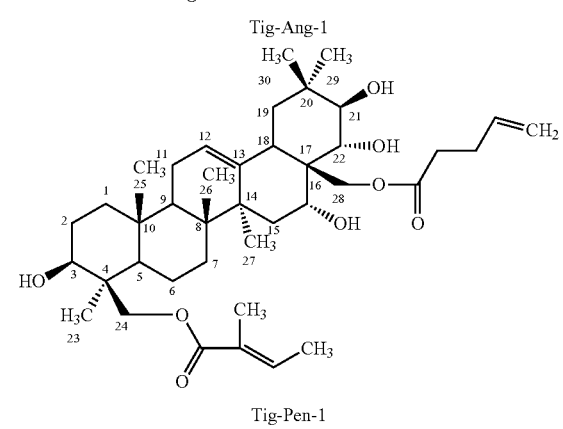
Tig-Pen-1

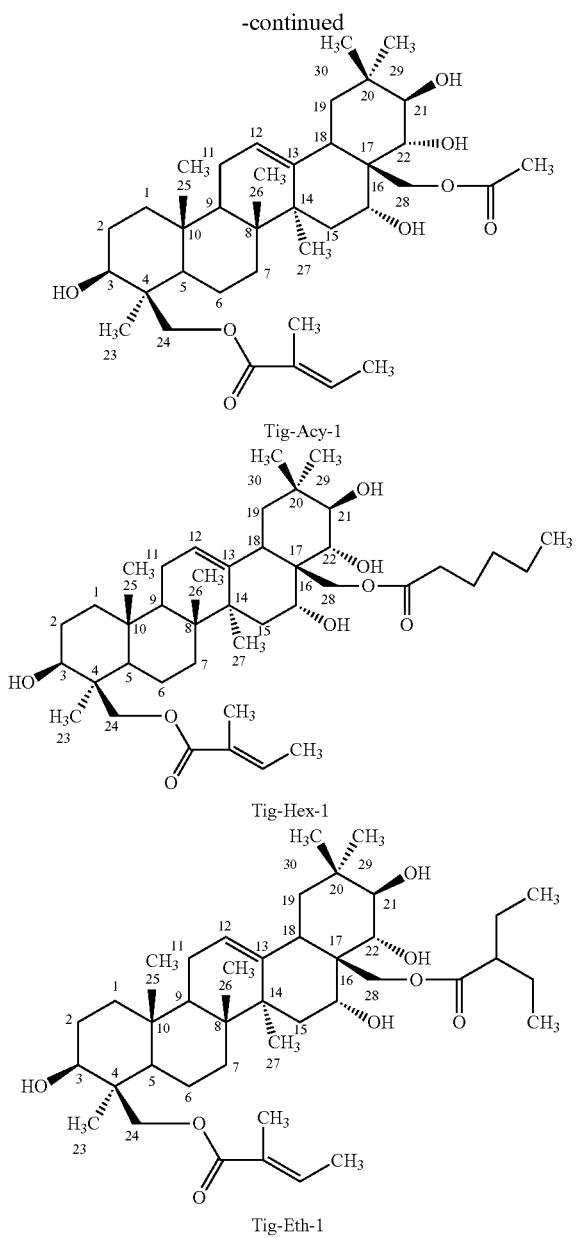

Tig-Acy-1

Tig-Hex-1

Tig-Eth-1

A composition comprising an effective amount of compound selected from the above formula or a salt, ester, metabolite or derivative thereof can be used as a medicament for blocking the invasion, migration, metastasis of cancer cells, inhibiting tumor or cancer cell growth and for treating cancer, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer.

This invention provides a composition comprising the compounds provided in the invention for treating cancers; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-Kappa B activation; for treating brain edema, severe acute respiratory syndrome, respiratory viral diseases, chronic venous insufficiency, hypertension, chronic venous disease, oedema, inflammation, hemonhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for AntiMS, antianeurysm, antiasthmatic, anti-oedematous, anti-inflammatory, antibradykinic, anticapillarihemorrhagic, anticephalagic, anticervicobrachialgic, antieclamptic, antiedemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cancer cells, antiparasitic; increase the expression of the genes: ANGPT2, DDIT3, LIF and NFKB1Z, and manufacturing an adjuvant composition and venotonic treatment.

Alkenyl means unsaturated linear or branched structures and combinations thereof, having formula R2C=CR2, one or more double bonds therein. Examples of alkenyl groups include vinyl, propenyl, isopropenyl, butenyl, s- and t-butenyl, pentenyl, hexenyl, butadienyl, pentadienyl, and hexadienyl.

An aryl is a functional group of organic molecule derived from an aromatic compound such as benzene, a 6-14 membered carbocyclic aromatic ring system comprising 1-3 benzene rings. If two or more aromatic rings are present, then the rings are fused together, so that adjacent rings share a common bond. Examples include phenyl and naphthyl. The aryl group may be substituted with one or more substitutes independently selected from halogen, alkyl or alkoxy.

Acyl is a functional group which can be obtained from an organic acid by the removal of the carboxyl. Acyl groups can be written using the general formula —COR, where there is a double bond between the carbon and oxygen. The names of acyl groups typically end in -yl, such as formyl, acetyl, propionyl, butyryl and benzoyl.

Benzoyl is one of the acyls, $C_6H_5COR$, obtained from benzoic acid by the removal of the carboxyl.

A heterocyclic compound is a compound containing a heterocyclic ring which refers to a non-aromatic ring having 1-4 heteroatoms, said ring being isolated or fused to a second ring selected from 3- to 7-membered alicyclic ring containing 0-4 heteroatoms, aryl and heteroaryl, wherein heterocyclic compounds include pyrrolidinyl, pipyrazinyl, morpholinyl, trahydrofuranyl, imidazolinyl, thiomorpholinyl, and the like.

Heterocyclyl groups are derived from heteroarenes by removal of a hydrogen atom from any ring atom.

Alkanoyl is the general name for an organic functional group RCO—, where R represents hydrogen or an alkyl group. Examples of alkanoyls are acetyl, propionoyl, butyryl, isobutyryl, pentanoyl and hexanoyl.

Alkenoyl is an alkenylcarbonyl in which the alkenyl is defined above. Examples are pentenoyl(tigloyl) and hexenoyl (angeloyl).

Alkyl is a radical containing only carbon and hydrogen atoms arranged in a chain, branched, cyclic or bicyclic structure or their combinations, having 1-18 carbon atoms. Examples include but are not limited to methyl, ethyl, propyl isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl and cyclohexyl.

Benzoyl alkyl substituted alkanoyl refers to straight or branched alkanoyl substituted with at least one benzoyl and at least one alkyl, wherein the benzoyl is attached to a straight or branched alkyl. An example of a benzoyl alkyl substituted alkanoyl is benzoyl methyl isobutanoyl.

A sugar moiety is a segment of molecule comprising one or more sugars or derivatives thereof or alduronic acid thereof.

Isobutyryl is a synonym of 2-Methylpropanoyl (Y)Y3, Y and Y3 represent the same compound.

YM and (ACH-Y) represent the same compound.

Connecting moiety is a substructure or a group of atoms which connect the functional group to a core compound. Example: angeloyl group is connected by a sugar moiety to a triterpene core.

The building blocks used in the invention including triterpenes, hydroxylated triterpenes, acetyl, angeloyl, tigloyl, senecioyl, Crotonoyl, O-3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, acetyl chloride, angeloyl chloride, tigloyl chloride, senecioyl chloride, Crotonoyl chloride, O-3,3-Dimethylartyloyl chloride, Cinnamoyl chloride, Pentenoyl chloride, Hexanoyl chloride, benzoyl chloride, Ethylbutyryl chloride.

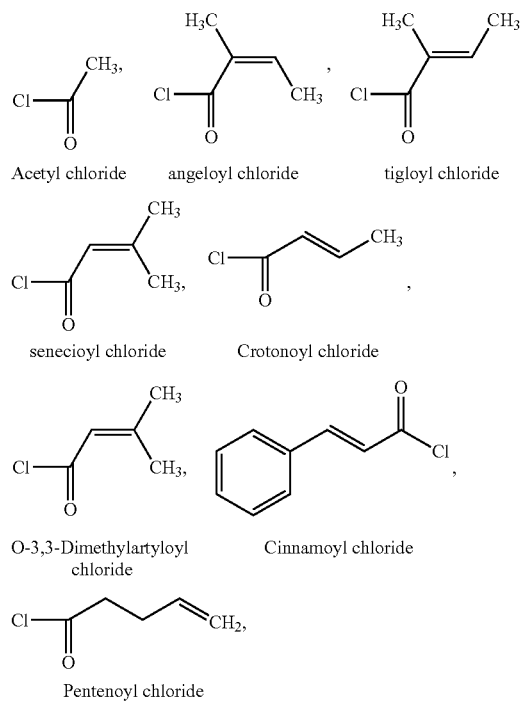

Acetyl chloride   angeloyl chloride   tigloyl chloride senecioyl chloride   Crotonoyl chloride O-3,3-Dimethylartyloyl chloride   Cinnamoyl chloride Pentenoyl chloride

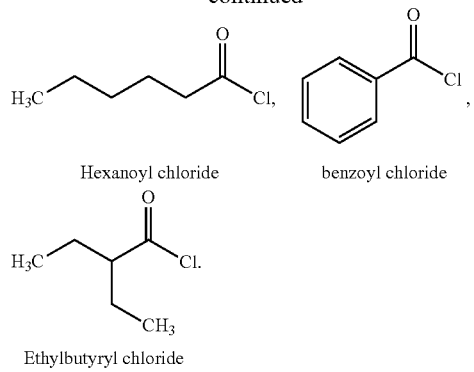

Hexanoyl chloride   benzoyl chloride

Ethylbutyryl chloride

In the presented experiments, concentrations of drug that inhibit 15% cell-growth or less (i.e. 85% of control or above) as compared to the no-drug control (DMSO) are considered non-cytotoxic concentrations. In an embodiment, the concentrations of drug that inhibit 10% cell-growth or less (i.e. 90% of control or above) as compared to the no-drug control (DMSO) are considered non-cytotoxic concentrations. In an embodiment, the concentrations of drug that inhibit 5% cell-growth or less (i.e. 95% of control or above) as compared to the no-drug control (DMSO) are considered non-cytotoxic concentrations. In an embodiment, the concentrations of drug that inhibit 20% cell-growth or less (i.e. 80% of control or above) as compared to the no-drug control (DMSO) are considered non-cytotoxic concentrations. In an embodiment, the concentrations of drug that inhibit 25% cell-growth or less (i.e. 75% of control or above) as compared to the no-drug control (DMSO) are considered non-cytotoxic concentrations. In an embodiment, the concentrations of drug that inhibit 30% cell-growth or less as compared to the no-drug control (DMSO) are considered non-cytotoxic concentrations. In an embodiment, the concentrations of drug that inhibit 45% cell-growth or less as compared to the no-drug control (DMSO) are considered non-cytotoxic concentrations.

The triterpene compound or compounds selected from this invention can be administered to a subject in need thereof, treating the subject, wherein including preventing cancer, or providing an adjuvant effect to the subject, or inhibiting the initiation or promotion of cancer, or killing the cancer/tumor cells, or inhibiting cancer cell invasion. In an embodiment the compounds inhibit the activation of nuclear factor-kB, wherein inhibiting the localization or wherein binding the DNA. In an embodiment the compounds induce apoptosis in cancer cells.

Table 1 to 12, Effect of Y and YM on gene expression (Table of 1 to 12 PCT/US2008/002086, 1188-ALA-PCT, filed Feb. 15, 2008 are incorporated herein by reference) Table 13 to 19, Effect of Y and YM on gene expression (Table of 13 to 19 PCT/US2009/034115, 1188-D-PCT, filed Feb. 15, 2008 are incorporated herein by reference)

Determination of Gene Expression by Real-Time PCR Method (Brilliant QPCR, Agilent Technologies):

The real-time polymerase chain reactions further confirm the results obtained from microarray analysis. The Real-time PCR results (shown below) confirmed that Compound Y3 and YM increase the expression of the genes: ANGPT2, DDIT3, LIF and NFKB1Z, wherein the results in Table 19-21 disclosed in PCT/US09/34115, filed Feb. 13, 2009 are incorporated herein by reference.

The saponins are partially hydrolyzed into a mixture of products which can be separated by HPLC. Specific partial hydrolysis of saponins can also be achieved with enzymes. The glycosidases catalyze the hydrolysis of the glycosidic linkage. Galactosidase is an enzyme which catalyzes the hydrolysis of galactosides. Glucosidase is an enzyme which breaks glucose from saponin. Other enzyme examples are xylanases, lactase, amylase, chitinase, sucrase, maltase, and neuraminidase.

The sugar moiety of the triterpenoid saponin (example Xanifolia Y) can be removed by acid hydrolysis. The synthetic compound of ACH-Y is obtained. ACH-Y is a triterpene with acyl groups but no sugar moiety. The acyl group of the saponin (example Xanifolia Y) can be removed by alkaline hydrolysis. The synthetic compound AKOH-Y can be obtained. AKOH-Y is a pentacyclic triterpene with sugar moieties. A pentacyclic triterpene can be obtained by acid and alkaline hydroysis of saponins from natural sources. A pentacyclic triterpene can be obtained by synthetic methods (Reference: Surendra et al., Rapid and Enantioselective Synthetic Approaches to Germanicol and Other Pentacyclic Triterpenes, Journal of the American Chemical Society, 2008, 130(27), 8865-8869). Pentacyclic triterpenes with sugar moieties can also be obtained by synthesis (Reference: Ple et al., Synthesis of L-arabinopyranose containing hederagenin saponins, Tetrahedron 61 (2005) 4347-4362). Acylation is the process of adding an acyl group to a compound. The Friedel-Crafts reaction is an example of this process. An active compound can be obtained by acylating a pentacyclic triterpenes, or hydroxylated triterpenes. In an embodiment, acylating C24, C28, C21 and C22 of a pentacyclic triterpenes, or hydroxylated triterpenes produce compounds for inhibiting cancer growth, cancer invasion, cell invasion, cancer cell invasion, cell attachment adhesion, or cell circulation. In an embodiment, the acyl group(s) may be at C3. In an embodiment, a sugar moiety is at C21, 22, or 28, wherein the sugar moiety is attached with 2 acyl groups. In an embodiment, acylating the compounds of (A), (B), (C), (D), (F), (G), (H), produce the compounds for inhibiting cancer invasion, cells invasion or cancer cell invasion; cancer metastasis; or cancer growth The building blocks in the present application are used to synthesise active saponins.

Acylating the compound (G) with angeloyl or tigloyl group gives the following compounds

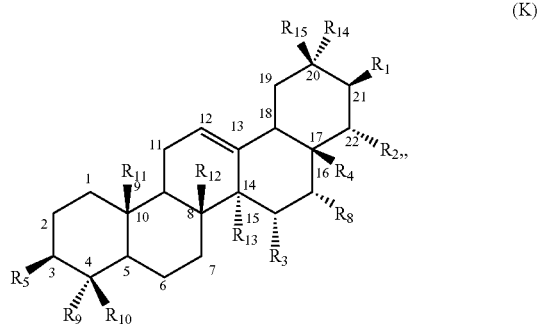
(K)

wherein R1, R2, R5, R8 represent OH or O-angeloyl; R3 represents OH, H or O-angeloyl; R4, R10 represent CH3, CH2OH or CH2O angeloyl; R3 represents OH, H or O-angeloyl; R9, R11, R12, R13, R14, R15 represent CH3; or wherein R1, R2, R5, R8 represent OH or O-tigloyl; R3 represents OH, H or O-tigloyl; R4, R10 represent CH3, CH2OH or CH2O tigloyl; R9, R11, R12, R13, R14, R15 represent CH3; wherein the compounds inhibit cancer growth, cancer invasion, cells invasion or cancer cell invasion.

Acylating the compound (G) with angeloyl, tigloyl, senecioyl, acetyl, Crotonoyl, 3,3-Dimethylartyloyl, Cinnamoyl, Pentenoyl, Hexanoyl, benzoyl, Ethylbutyryl, alkyl, dibenzoyl, benzoyl, alkanoyl, alkenoyl, benzoyl alkyl substituted O-alkanoyl, alkanoyl substituted phenyl, alkenoyl substituted phenyl, aryl, acyl, heterocylic, heteroraryl, CH2O-alkenylcarbonyl, alkane, alkene give the compound (K) wherein R1, R2, R5, R8 represent OH, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl; R4, R10 represent CH3, CH2OH, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, alkane, alkene; R3 is absent of represents OH, H, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl; wherein R9, R11, R12, R13, R14, R15 represent CH3; wherein the compounds inhibit cancer growth, cancer invasion, cells invasion or cancer cell invasion; wherein the compound for use as mediator or inhibitor of adhesion protein or angiopoietin; wherein the compounds use as mediator modulating the secretion, expression, or synthesis of adhesion protein comprises reducing the fibronectin for inhibiting cell attachment, cell adhesion or cell circulation; wherein the adhesion proteins comprise fibronectin, integrins family, myosin, vitronectin, collagen, laminin, polyglycans, cadherin, heparin, tenascin, $CD_{54}$, and CAM; the compounds use for anti adhesion therapy and targeting adhesion molecules for therapy.

Applicant further states that anti adhesion therapy and targeting adhesion molecules for therapy is a new direction for development of drugs. Some examples of anti-adhesion drugs in clinical trials are Efalizumab, Odulimomab, Alicaforsen, Aselizumab etc, which target varies adhesion proteins. Please see TEXT BOOK, Adhesion Molecules: Function and Inhibition, (Reference 2), edited by Klaus Ley page 289-291, 297.

Adhesion molecules in inflammatory disease, (Reference 4), Abstract, line 7-8 "Blockade of the function of expression of CAM has emerged as a new therapeutic target in inflammatory diseases". Applicants' invention is an anti adhesion therapy which is a new use of the compound as a mediator or inhibitor of adhesion proteins and angiopoietins. It inhibits excess adhesion and inhibits cell attachment.

In the present application, Applicants have used compounds selected from structure (2A) for anti adhesion therapy, as a mediator or inhibitor of adhesion proteins and angiopoietins, and modulation of the cell attachment, and cell adhesion.

EXPERIMENTAL DETAILS

Experiment details of herb extraction, analysis of extract components by HPLC, determination of the cell-growth activity effected by Xanifolia Y with cells derived from different human organs using MTT Assay, purification of the bioactive components from plant extract, fractionation of plant extracts with FPLC, isolation of component Ys with preparative HPLC, determination of the chemical structure, cell experiments and animal studying are disclosed in PCT/US05/31900, U.S. Ser. No. 11/289,142, U.S. Ser. No. 10/906,303, U.S. Ser. No. 11/131,551 and U.S. Ser. No. 11/683,198, filed on Mar. 7, 2007, PCT/US2007/077273, filed Aug. 30, 2007, U.S. Ser. No. 60/890,380, filed on Feb. 16, 2007, U.S. No. 60/947,705, filed on Jul. 3, 2007, PCT/US2008/002086, 1188-ALA-PCT, filed Feb. 15, 2008, App'l No. PCT/US09/34115, filed Feb. 13, 2009, the contents of which are incorporated herein by reference. Experiments 1-23 of PCT/US2008/002086, 1188-ALA-PCT, filed Feb. 15, 2008 are incorporated herein by reference.

Experiment 1

Removal of the Sugar Moiety from Saponin by Acid Hydrolysis 15 mg saponin was dissolved in 1 ml of Methanol. 1 ml of 2N HCl was then added. The mixture was refluxed in 80 C water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (sugar-removed saponin) was achieved by HPLC with isocratic elution of 80-100% acetonitrile.

Experiment 2

Removal of the Acyl Group by Alkaline Hydrolysis

Methods:
20 mg of saponin was dissolved in 0.5 ml of 1N NaOH. The solution was incubated in 80 C water bath for 4 hours. It was cooled to room temperature before neutralized with 0.5 ml 1N HCl (adjust pH to about 3). The mixture was extracted with 2 ml 1-butanol 3 times. The butanol fractions were collected and lyophilized. The hydrolyzed saponin with further purified with HPLC in a C-18 column eluted with 25% acetonitrile.

Experiment 3

Adding the Acyl Group to Triterpene by Esterification

Method: 40 mg of triterpene core (fraction IV) was dissolved in 1 ml pyridine in a 50 ml tube. Reaction is started by adding 0.2 ml of acyl chloride (Tigloyl chloride, angeloyl chloride, Acetyl chloride, Crotonoyl chloride, 3,3-Dimethylartyloyl chloride (senecioyl chloride), Cinnamoyl chloride, Pentenoyl chloride, Hexanoyl chloride, benzoyl chloride or Ethylbutyryl chloride). The mixture is stirred for 5 sec, 1 min, 2 min, 5 min, 10 min, 30 min, 1 hr, 2 hr, 18 hr, 2 days or 3 days at 0 C, 25 C or 75 C temperature. At the end of reaction, 5 ml of 2N HCl or 1M NaHCO3 is added to the reaction mixture. The solution is then extracted 3 times with 10 ml of ethyl acetate which is then evaporated under vacuum and at 45 C and lyophilization. The reaction product is dissolved in 80% acetonitrile-0.005% Trifluoroacetic acid or DMSO; and was separated with HPLC. Selecting the HPLC fractions for isolation is according to the cytotoxic activity of the reaction product obtained at a specific reaction time. The active esterification products are purified with HPLC. The reaction product of mixtures and individual compounds are tested with MTT cytotoxic assay. See examples FIGS. 1-12

Experiment 4

Preparation of E4A

1. Beta-Escin dissolved in 1M NaOH (20 mg/ml) was incubated at 70 C for 5 hours.
2. The hydrolyzed solution was neutralized with HCl and the water was evaporated by lyophilization.
3. The product was dissolved in 50% methanol and 1N HCl. The mixture was incubated at 70 C for 5 hours.
4. The solution was neutralized with NaOH.
5. The hydrolyzed product was extracted with ethylacetate, which was subsequently removed by evaporation.
6. Further purification of the hydrolyzed product (E4A) was archived with FPLC chromatography in a C18 column equilibrated with 70% acetonitrile/TFA at the flow rate of 1 ml/min.

Experiment 5

Esterification of E4A with Tigloyl Chloride 1. 50 mg of E4A in 1 ml pyridine, stir gently in a 50 ml tube. Esterification was carried out at 25 C by adding 200 ul Tigloyl chloride.
2. Stir for 1 minute; then immediately add 5 ml of 2N HCl.
3. Stir for 1 hour and sit at room-Temp over night.
4. Extract the esterification products with 10 ml ethylacetate.
5. Evaporate the ethylacetate.
6. Dissolve the sample with 1 ml DMSO.
7. Fractionate the reaction products with HPLC.
8. Collect samples.

Experiment 6

Isolation of E4A-Tig Active Compounds with HPLC

1. Column: ZORBAX ODS 9.4×250 mm, 5 um
2. Solvents: A: 45% AN/TFA; B: 100% AN/TFA
3. Chromatography conditions: a) Elution: Solvent A to B in 80 min; then with solvent B for 40 min; b) flow rate: 1 ml/mim. c) Monitor OD: at 207 nm;

Experiment 7

MTT Experiment

Cells.
HTB-9 (bladder), HeLa-S3 (cervix), DU145 (prostate), H460 (lung), MCF-7 (breast), K562 (leukemia), HCT116 (colon), HepG2 (liver), U2OS (bone), T98G (brain), SK-MEL-5 (Skin) and OVCAR 3, ES2 (ovary), Pancreas (Capan), Mouth (KB), Kidney (A498).

MTT Assay.
The procedure for MTT assay followed the method described by Carmichael et al. (1987) with modifications. The cells were seeded into a 96-well plate at for 24 hours before drug-treatment. The cells were then exposed to the drugs for 48, 72, or 96 hours. After the drug-treatment, MTT (0.5 mg/mL) was added to cultures and incubated for an hour.

The formazan (product of the reduction of tetrazolium by viable cells) formed and was dissolved with DMSO and the O.D. at 490 nm, and was measured by an ELISA reader. The MTT level of the cells before drug-treatment was also measured (T0). The % cell-growth (% G) is calculated as: % G=(TD−T0/TC−T0)×100(1), where TC or TD represents O.D. readings of control or drug-treated cells. When T0>TD, then the cytotoxicity (LC) expressed as % of the control is calculated as: % LC=(TD−T0/T0)×100(2).

Experiment 8

Chemical Synthesis, Isolation and Characterization of E4A-Tig-R

Chemical synthesis of E4A-Tig-R: 1. Preparation of E4A; 2. Esterification of E4A with Tigloyl Chloride; 3. Isolation of E4A-Tig-R with HPLC Cytotoxic activity determination: 1. MTT assay Chemical structure determination: 1. NMR analysis; 2. Mass Spectrum analysis See FIG. 23-30

See Table 1

Compound E4A-Tig-R 24,28-O-Tigloyl-3β,16α,21β,22α,24α,28-hexahydroxyolean-12-ene

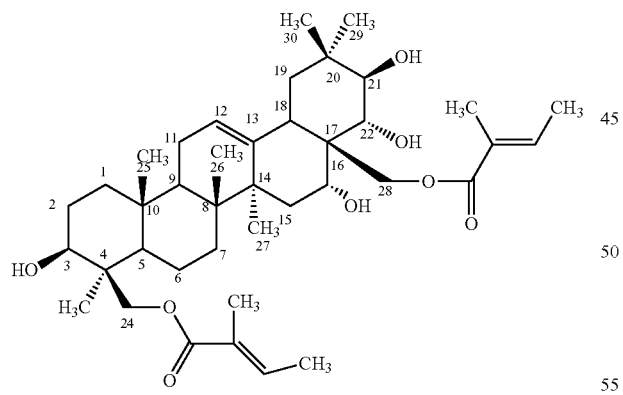

Experiment 9

Chemical Synthesis, Isolation and Characterization of E4A-Tig-N

Chemical synthesis of E4A-Tig-R: 1. Preparation of E4A; 2. Esterification of E4A with Tigloyl Chloride; 3. Isolation of E4A-Tig-N with HPLC Cytotoxic activity determination: 1. MTT assay Chemical structure determination: 1. NMR analysis; 2. Mass Spectrum analysis

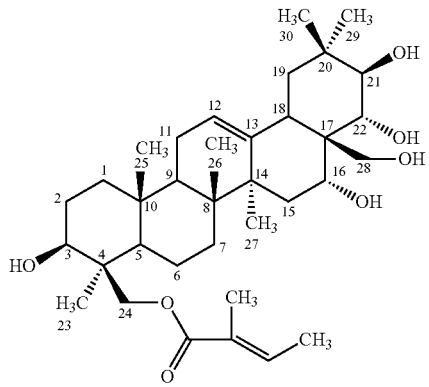

Experiment 10

Chemical Synthesis, Isolation and Characterization of E4A-Tig-Q

Chemical synthesis of E4A-Tig-R: 1. Preparation of E4A; 2. Esterification of E4A with Tigloyl Chloride; 3. Isolation of E4A-Tig-Q with HPLC Cytotoxic activity determination: 1. MTT assay Chemical structure determination: 1. NMR analysis; 2. Mass Spectrum analysis

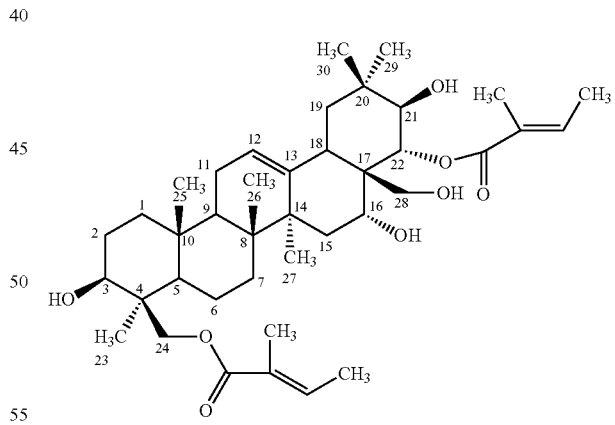

Experiment 11

Chemical Synthesis, Isolation and Characterization of E4A-Tig-V

Chemical synthesis of E4A-Tig-V: 1. Preparation of E4A; 2. Esterification of E4A with Tigloyl Chloride; 3. Isolation of E4A-Tig-V with HPLC Cytotoxic activity determination: 1. MTT assay Chemical structure determination: 1. NMR analysis; 2. Mass Spectrum analysis

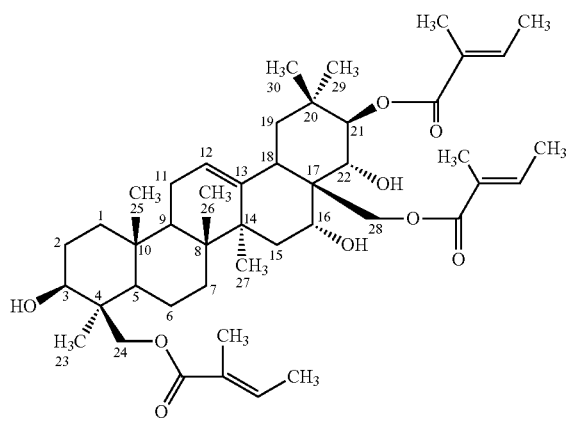

Experiment 12

Chemical Synthesis, Isolation and Characterization of E4A-Tig-T

Chemical synthesis of E4A-Tig-T: 1. Preparation of E4A; 2. Esterification of E4A with Tigloyl Chloride; 3. Isolation of E4A-Tig-T with HPLC Cytotoxic activity determination: 1. MTT assay Chemical structure determination: 1. NMR analysis; 2. Mass Spectrum analysis

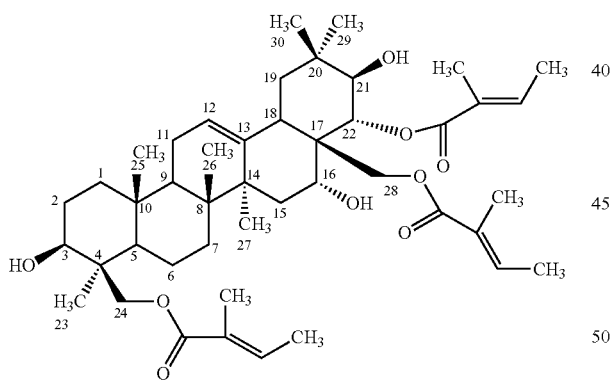

Experiment 13

Chemical Synthesis, Isolation and Characterization of E4A-Tig-U

Chemical synthesis of E4A-Tig-S: 1. Preparation of E4A; 2. Esterification of E4A with Tigloyl Chloride; 3. Isolation of E4A-Tig-S with HPLC Cytotoxic activity determination: 1. MTT assay Chemical structure determination: 1. NMR analysis; 2. Mass Spectrum analysis

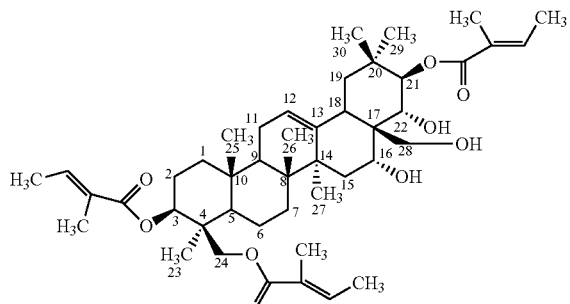

Experiment 14

Chemical Synthesis, Isolation and Characterization of E4A-Tig-S

Chemical synthesis of E4A-Tig-S: 1. Preparation of E4A; 2. Esterification of E4A with Tigloyl Chloride; 3. Isolation of E4A-Tig-S with HPLC Cytotoxic activity determination: 1. MTT assay Chemical structure determination: 1. NMR analysis; 2. Mass Spectrum analysis

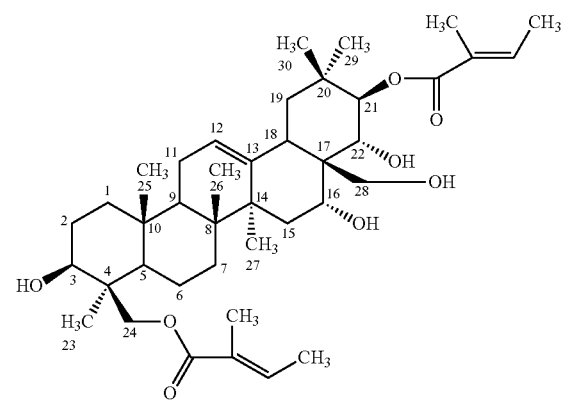

Experiment 15

Using method in Experiment 8, esterification of E4A with acetyl, angeloyl, tigloyl, senecioyl, Crotonoyl, Cinnamoyl, Pentenoyl, Hexanoyl, Ethylbutyryl, gave the following compounds

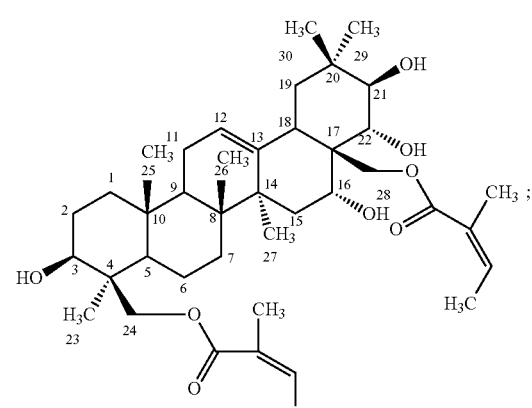

Compound E4A-Ang-R

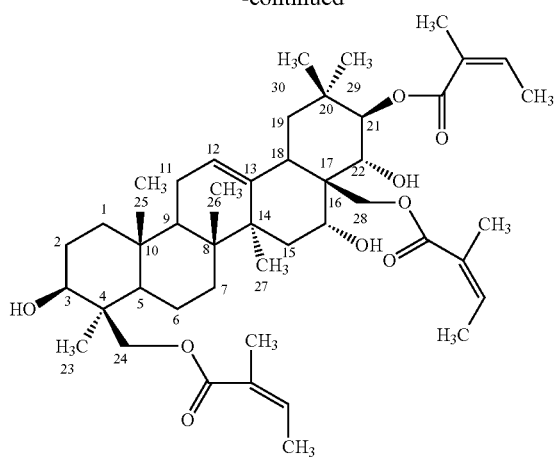
Compound E4A-Ang-V
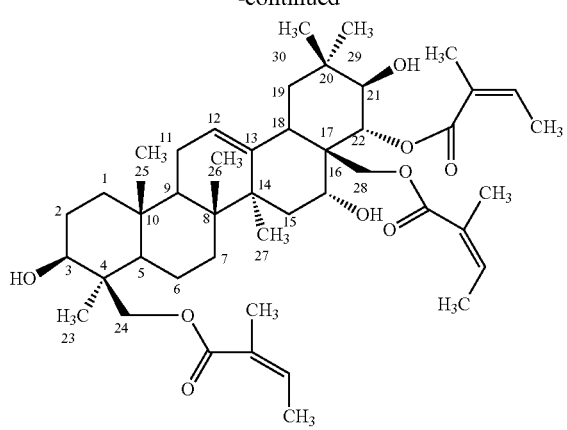
Compound E4A-Ang-T:
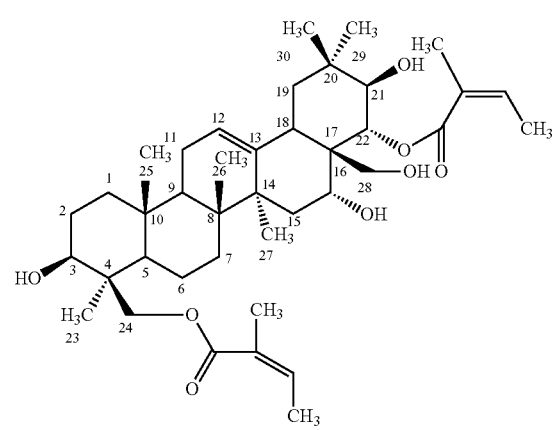
Compound E4A-Ang-Q:
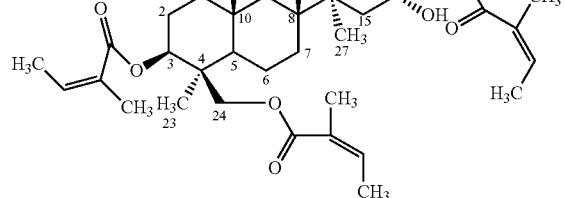
Compound E4A-Ang-U
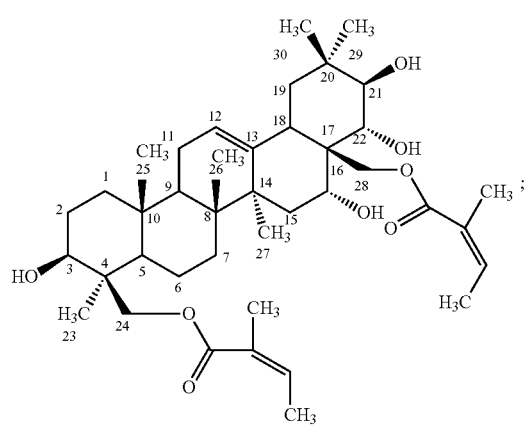
Compound E4A-Ang-N:
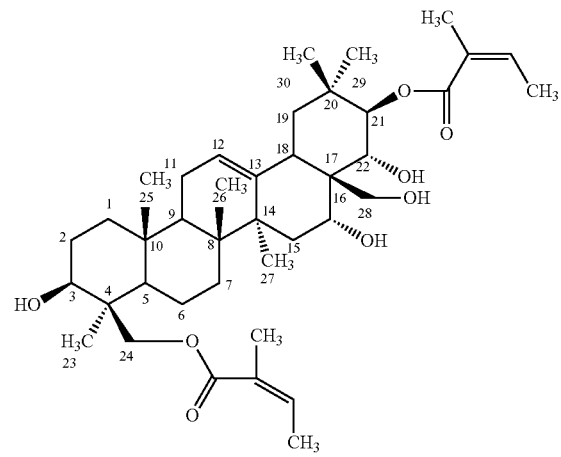
Compound E4A-Ang-S:

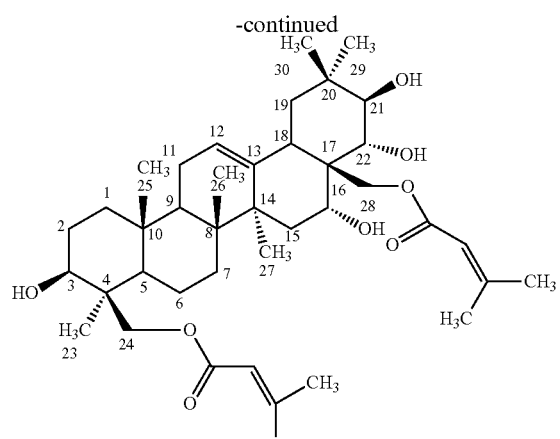
Compound E4A-Sen-R
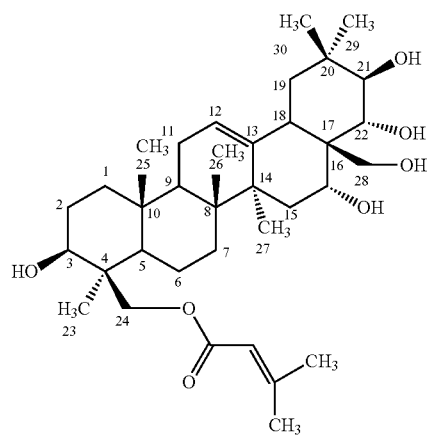
Compound E4A-Sen-V:
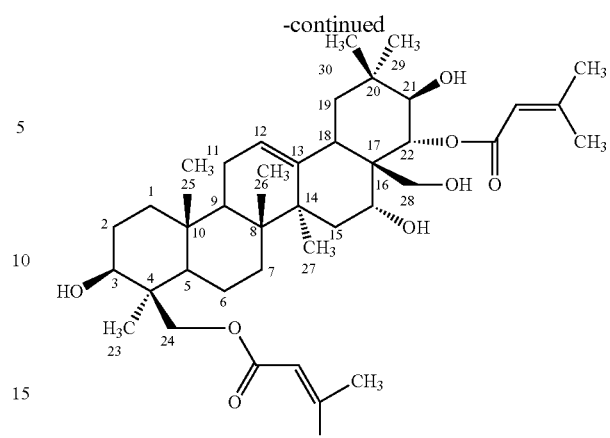
Compound E4A-Sen-N:
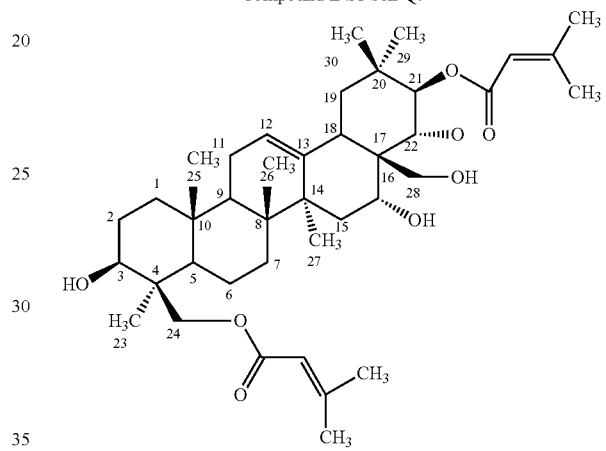
Compound E4A-Sen-Q:
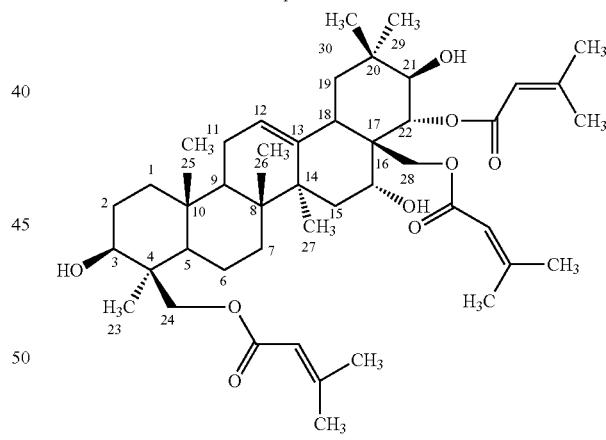
Compound E4A-Sen-S
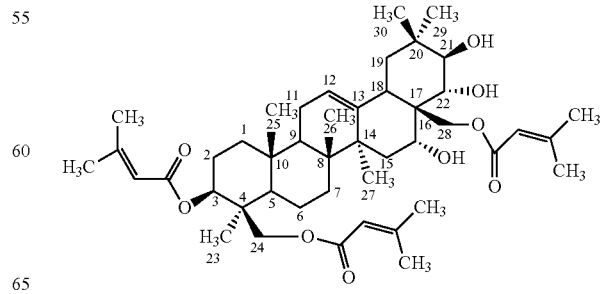
Compound E4A-Sen-T:
Compound E4A-Sen-U:

-continued
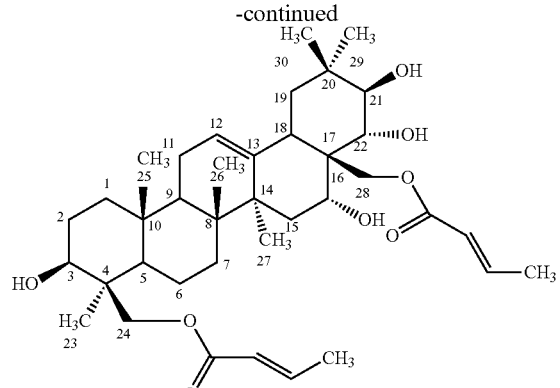
Compound E4A-Cro-R:
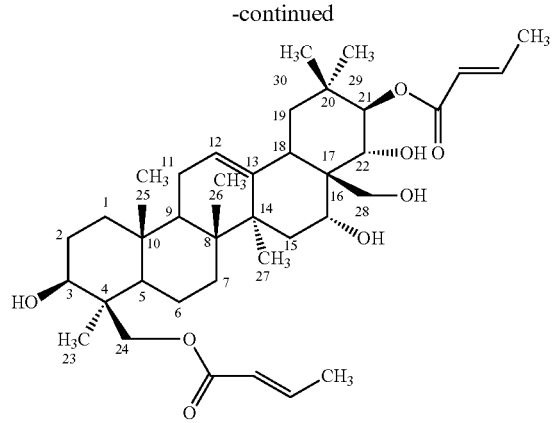
Compound E4A-Cro-S:
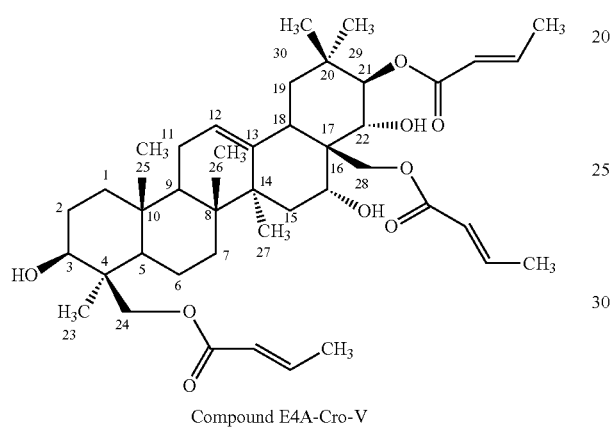
Compound E4A-Cro-V
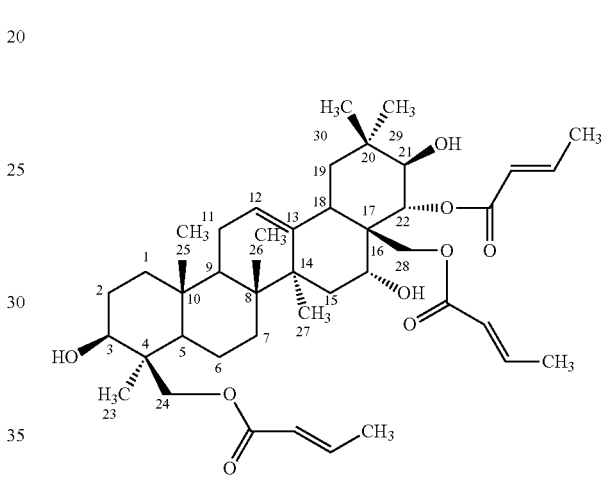
Compound E4A-Cro-T:
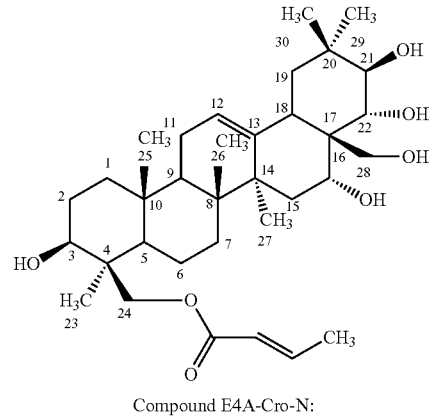
Compound E4A-Cro-N:
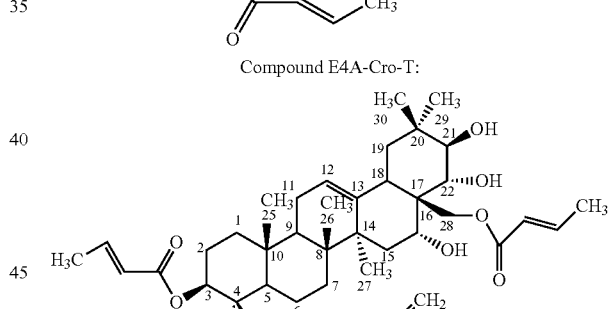
Compound E4A-Cro-U:
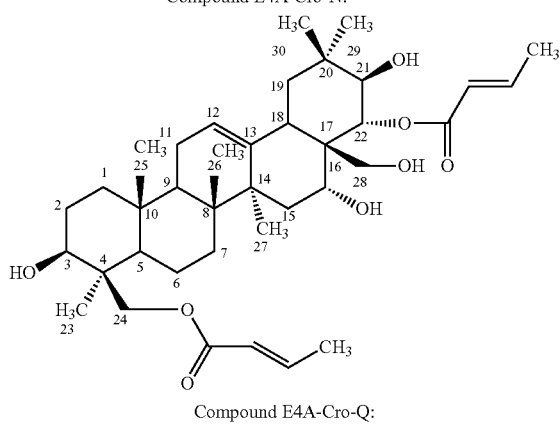
Compound E4A-Cro-Q:
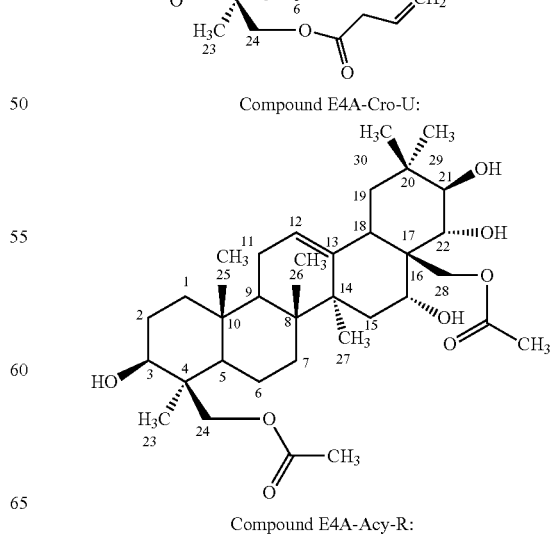
Compound E4A-Acy-R:

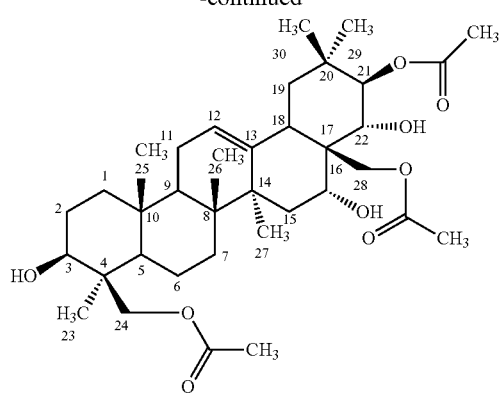
Compound E4A-Acy-V:
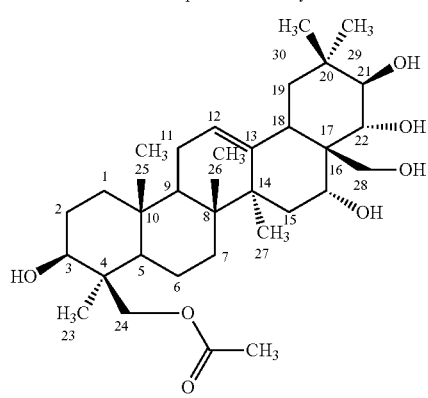
Compound E4A-Acy-N:
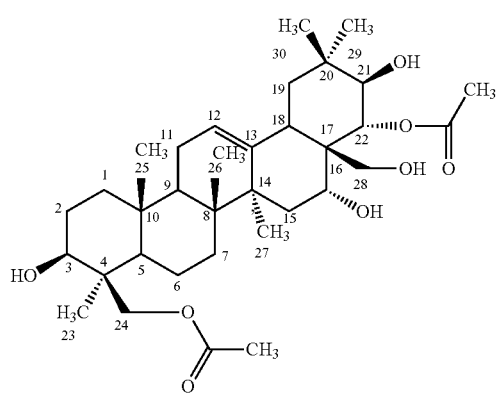
Compound E4A-Acy-Q:
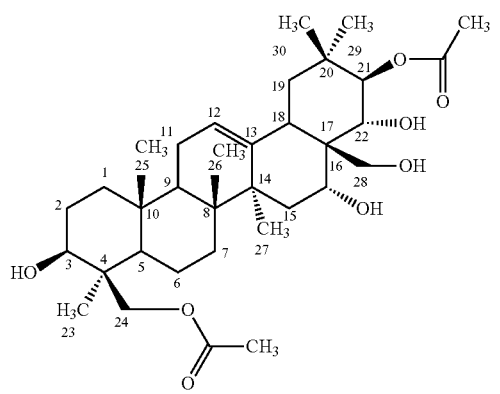
Compound E4A-Acy-S:
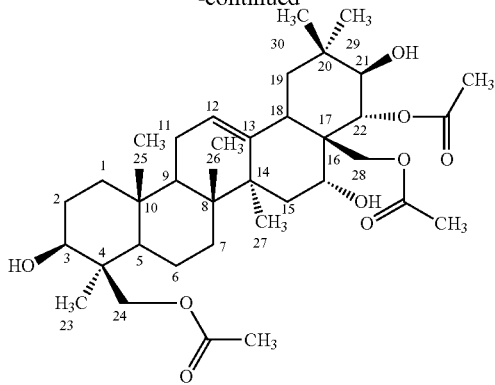
Compound E4A-Acy-T:
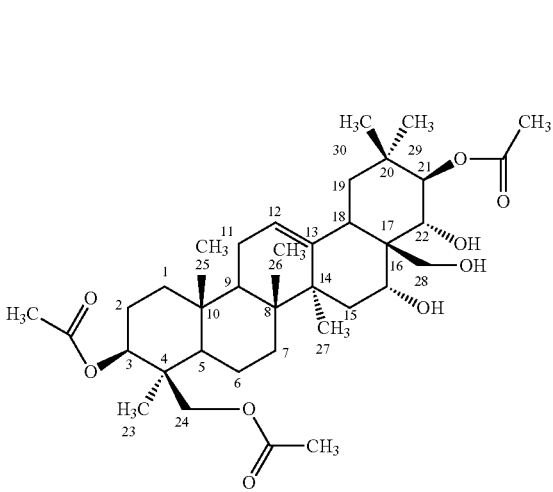
Compound E4A-Acy-U:
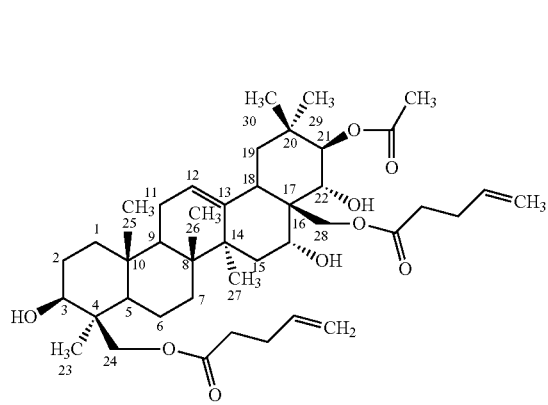
Compound E4A-Pen-R:
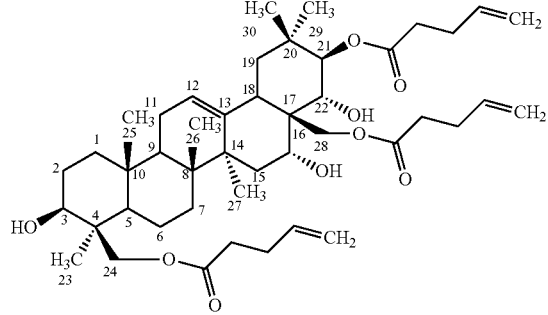
Compound E4A-Pen-V:

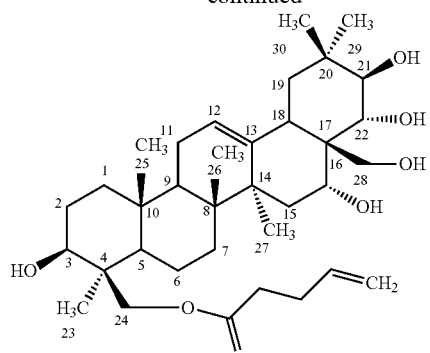
Compound E4A-Pen-N:
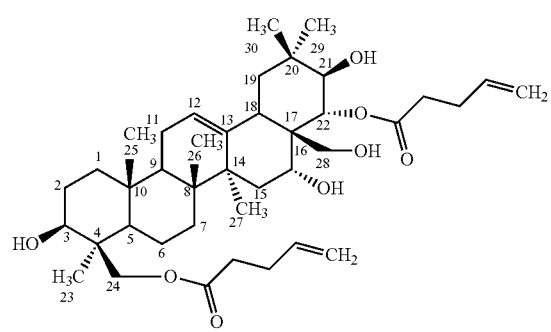
Compound E4A-Pen-Q:
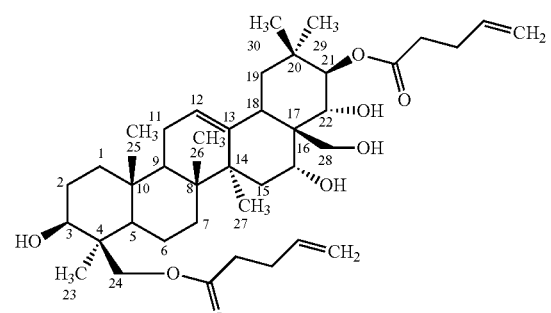
Compound E4A-Pen-S:
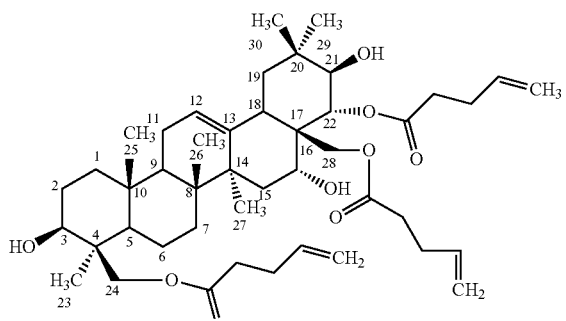
Compound E4A-Pen-T:
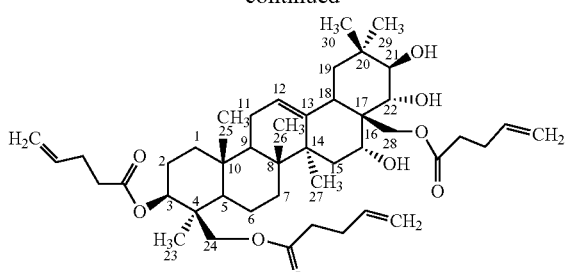
Compound E4A-Pen-U:
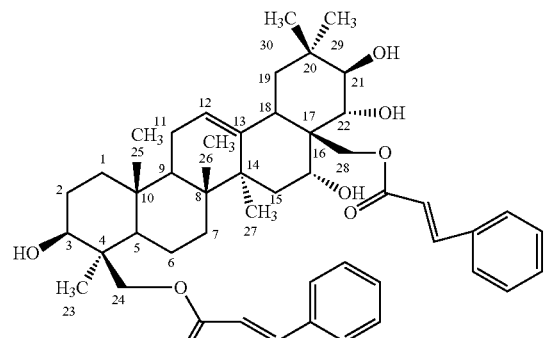
Compound E4A-Pen-R:
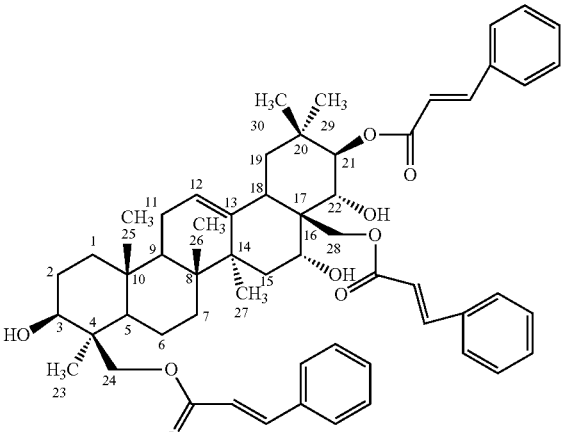
Compound E4A-Pen-V:
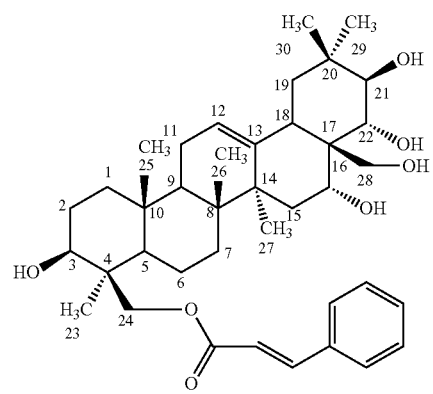
Compound E4A-Pen-N:

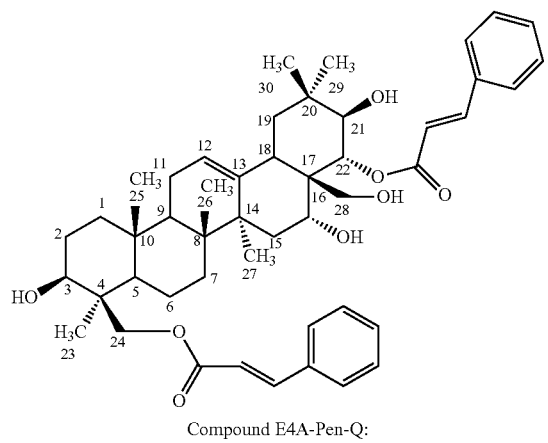

Compound E4A-Pen-Q:

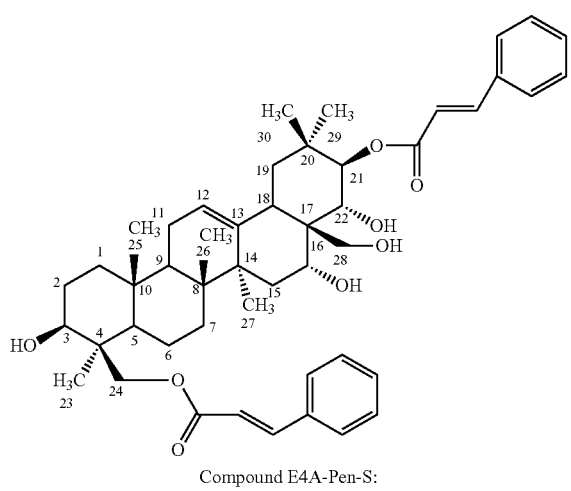

Compound E4A-Pen-S:

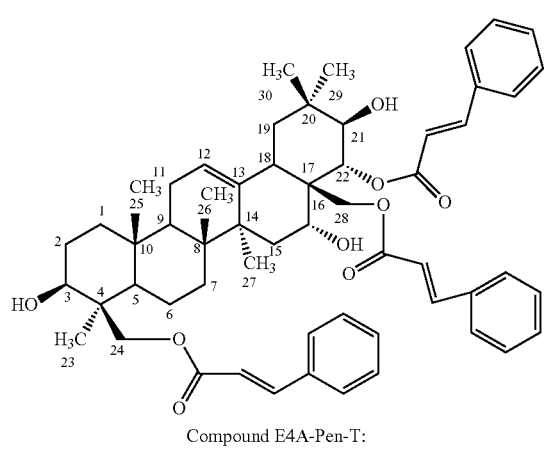

Compound E4A-Pen-T:

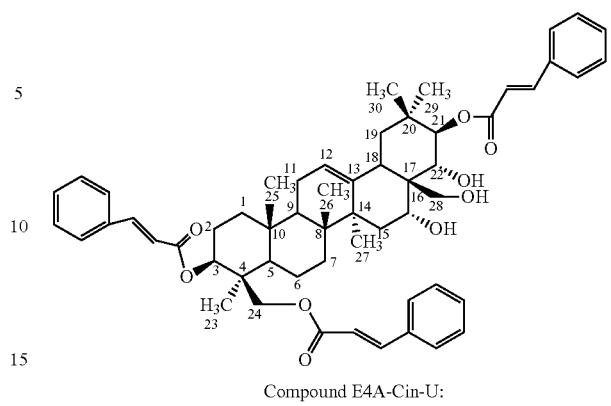

Compound E4A-Cin-U:

Experiment 16

Esterification of E4A-Tig-N with Senecioyl Chloride

Chemical synthesis of E4A-Tig-Sen-1:1. Esterification of E4A-Tig-N with Senecioyl Chloride; 3. Isolation of E4A-Tig-Sen-1 with HPLC Cytotoxic activity determination: 1. MTT assay Chemical structure determination: 1. NMR analysis; 2. Mass Spectrum analysis

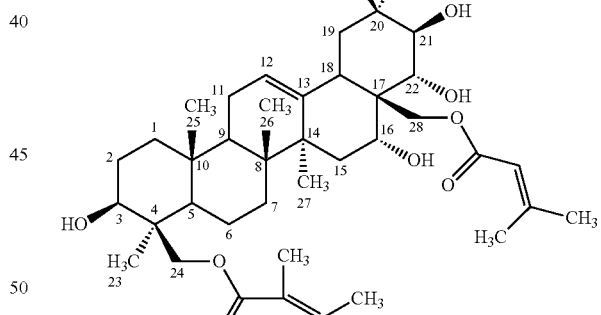

Experiment 17

Esterification of E4A-Tig-N with angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride or Ethylbutyryl chloride; Isolation with HPLC; Cytotoxic activity determination; Chemical structure determination with the method of Experiment 8, gave the following compounds:

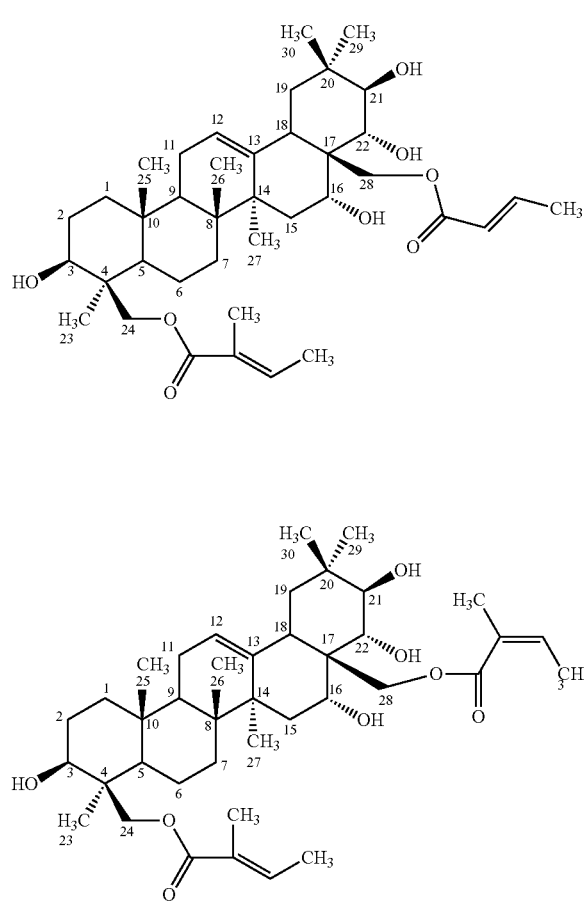

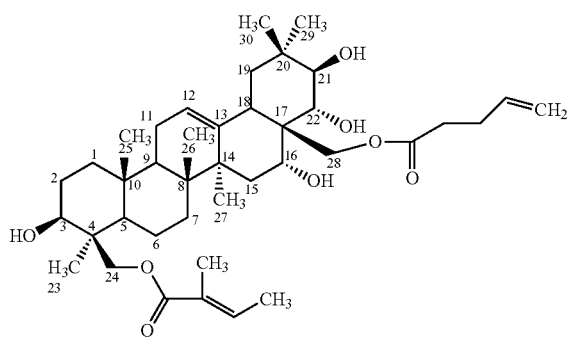

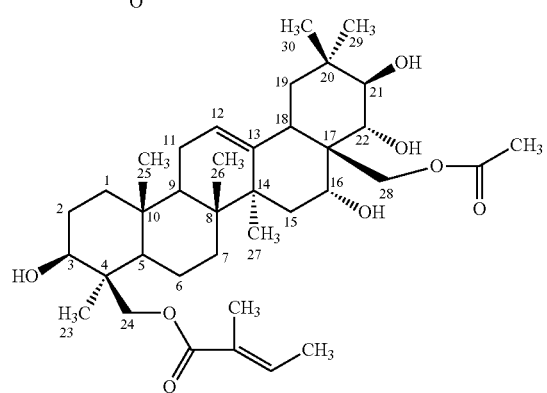

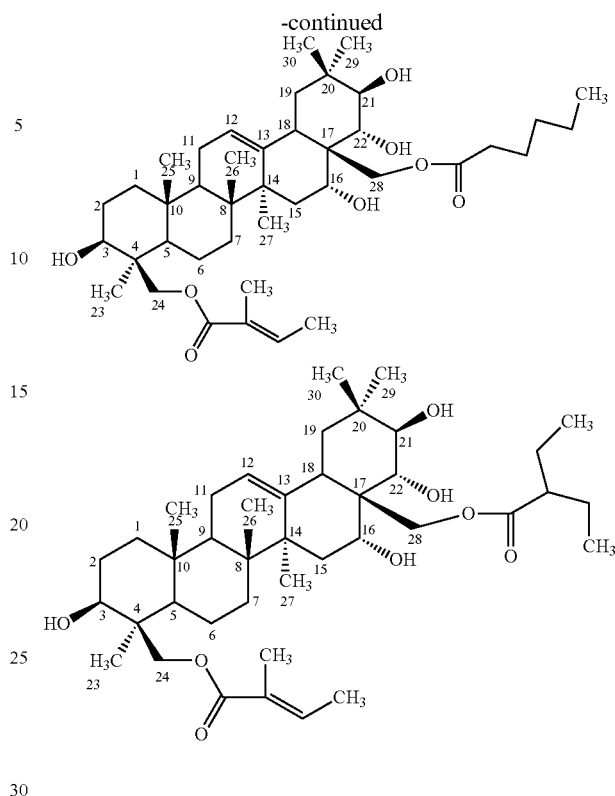

-continued

Experiment 18

Inhibition of Cell Adhesion

Methods and Results. ES2 or Hey8A cells were plated in T25 flasks with medium containing 5 ug/ml of compounds selected from structure (2A) including E4A-Tig-R, E4A-Tig-V, E4A-Tig-S, E4A-Tig-N, E4A-Tig-Q, E4A-Tig-T. Cultures were incubated for 5 hours. Attached cells were removed from flasks by trypsinization and the amounts were counted. Compare to no drug controls, 80±4% of ES2 cells and 60±4% of Hey8A cells were found attached to flasks under this condition. At 5 ug/ml of above compounds, over 90% of unattached cells are alive as determined by the trypan Blue exclusion assay and by their ability to re-attach to flasks when plating in medium without tested compounds. However, with 10 ug/ml tested compounds, less than 40% of cells attached to flasks and many of them are dead cells. This experiment shows that tested compounds inhibit cells adhesion process.

Experiment 19

Fibronectin Secretion Experiment

Western blot is applied in this invention as a method to detect the specific proteins in treated and untreated cells with compounds in this invention, wherein the cells are bladder, cervix, prostate, lung, breast, leukemia, colon, liver, bone, brain, Skin, ovary, Pancreas (Capan), Mouth (KB), Kidney Cells: targeted cells were grown in RPMI 1640 medium. 1.5 million cells were seeded in a T25 flask and grown for 24 hours before drug-treatment.

Drug-treatment: Cells cultures were replaced with fresh RPMI medium containing either 2.5 ul of DMSO (as control) [D]; or 10, 20, 30, 40, 80 ug/ml of tested compounds. After 24 hours, aliquot of culture medium was taken out for Fibronectin determination (Western blot method).

Cell viability at 24 hours was determined by MTT assay. Cultures were replaced with RPMI medium (5 ml) with MTT and incubated for an hour. The formation of formazan was dissolved in 10 ml of DMSO and OD at 570 nm was measured (MTT units). Western Blot Spent culture medium was mixed with SDS sample buffer, boiled for 3 minutes before loading to SDS gel. Samples were applied to a 6-10% SDS gel and electrophoresis was conducted with 100 volts for 2 hours. Protein was transferred to a nitrocellulose membrane electrophoretically. The nitrocellulose blot was incubated with the first antibody and second antibody (AP conjugated, Promega S3721). The immuno-bands were developed with BCIP/NBT color development system.

Determination of Western band intensity: The band-images of Western blot were captured with a digital camera and the intensity of bands was determined using "Image J" software.

Results show that compounds of E4A-Tig-R, E4A-Tig-V, E4A-Tig-S, E4A-Tig-N, E4A-Tig-Q, E4A-Tig-T inhibit fibronectin secretion from 20-40%. in bladder, cervix, prostate, lung, breast, leukemia, colon, liver, bone, brain, Skin, ovary, Pancreas (Capan), Mouth (KB), Kidney.

TABLE 1

Table. $^{13}C$ and $^{1}H$ NMR data for E4A-Tig-R (in DMSO-$d_6$)$^a$

| Position | C | H | Key HMBC correlations |
|---|---|---|---|
| 1 | 38.24 | 0.96, t, 1.56, t | C-25 |
| 2 | 26.77 | 1.52, br, m | — |
| 3 | 76.69 | 3.15, 1H, dd | C23, C24 |
| 4 | 41.5 | — | — |
| 5 | 54.88 | 0.82, 1H | C23, C24, C25 |
| 6 | 19.51 | 1.47, 1.65, | C5 |
| 7 | 32.81 | 1.28, 1.43 | C26 |
| 8 | 39 | — | C27, C26 |
| 9 | 46.1 | 1.55 m | C25, C26 |
| 10 | 36.33 | — | C9, C25, C26 |
| 11 | 22.97 | 1.79 m | C9 |
| 12 | 122.25 | 5.18, 1H, t | C9, C11, C14, C18 |
| 13 | 142.32 | — | C18, C27 |
| 14 | 40.7 | — | C26, C27 |
| 15 | 33.56 | 1.28, 1.64 | C27 |
| 16 | 66.47 | 4.01, 1H, s | C22, C28 |
| 17 | 45.3 | — | C22, C28 |
| 18 | 39.9 | 2.41, br, m, | C12, C28 |
| 19 | 46.59 | 0.98, 2.42 m | C29, C30 |
| 20 | 35.23 | — | C29, C30 |
| 21 | 76.50 | 3.84, 1H, d, 9.6 Hz | C22, C29, C30 |
| 22 | 71.89 | 3.55, 1H, d, 9.6 Hz | C21, C28, |
| 23 | 22.62 | 1.06, 3H, s | C3, C5, C24, |
| 24 | 66.17 | 4.14, 1H, d, 12 Hz | C3, C5, C-23 |
|    |       | 4.17, 1H, d, 12 Hz | 24-O-Tig-C1' |
| 25 | 14.89 | 0.88, 3H, s | C-1, C-5, C-9, C-10 |
| 26 | 16.13 | 0.81, 3H, s | C-7, C-8, C-9, C-14 |
| 27 | 26.65 | 1.36, 3H, s | C-8, C-18, C14, C-15 |
| 28 | 65.34 | 3.68, 1H, d, 10.4 Hz, | C17, C-18, C-22 |
|    |       | 3.73, 1H, d, 10.4 Hz, | 28-O-Tig C1' |
| 29 | 29.87 | 0.86, 3H, s | C-19, C20, C-21, C-30 |
| 30 | 18.49 | 0.85, 3H, s | C-19, C20, C-21, C-29 |
| 24-O-Tig | | | |
| 1' | 167.24 | — | C24, Tig C-3', |
| 2' | 128.29 | — | Tig-C3', Tig C-4', Tig C-5' |
| 3' | 136.8 | 6.77, 1H, | Tig C-4', Tig C-5' |
| 4' | 11.9 | 1.78, 3H, | Tig C-1', C-2', C-3' |
| 5' | 13.99 | 1.77, 3H, | Tig C-1', C-2', C-3' |
| 28-O-Tig | | | |
| 1' | 166.68 | — | C28, Tig C-3' |
| 2' | 128.1 | — | Tig C-3', Tig C-4', Tig C-5' |
| 3' | 136.5 | 6.77, 1H, | Tig C-4', Tig C-5' |
| 4' | 11.9 | 1.78, 3H, | Tig C-1', C-2', C-3' |
| 5' | 14.08 | 1.77, 3H, | Tig C-1', C-2', C-3' |

TABLE 2

Table. $^{13}C$ and $^{1}H$ NMR data for E4A-Tig-V (in DMSO-$d_6$)$^a$

| Position | C | H | Key HMBC correlations |
|---|---|---|---|
| 1 | 38.20 | 0.98, 1.57 | C-25 |
| 2 | 26.75 | 1.54, br, m | — |
| 3 | 76.65 | 3.15, 1H, dd | C23, C24 |
| 4 | 41.48 | — | — |
| 5 | 54.82 | 0.82, 1H | C23, C24, C25 |
| 6 | 19.49 | 1.47, 1.65, | C5 |
| 7 | 32.71 | 1.29, 1.46 | C26 |
| 8 | 39 | — | C27, C26 |
| 9 | 46.09 | 1.57 m | C25, C26 |
| 10 | 36.31 | — | C5, C9, C25, |
| 11 | 22.97 | 1.81 m | |
| 12 | 122.65 | 5.22, 1H, t | C9, C11, C14, C18 |
| 13 | 141.83 | — | C18, C19, C27 |
| 14 | 40.68 | — | C12, C18, C26, C27 |
| 15 | 33.59 | 1.29, 1.66 | C27 |
| 16 | 66.14 | 4.03, 1H, s | C18, C22, C28 |
| 17 | 45.69 | — | C18, C22, C28 |
| 18 | 39.5 | 2.5, br, m, | C12, C19, C28 |
| 19 | 46.17 | 1.07, 2.56 m | C18, C29, C30 |
| 20 | 35.33 | — | C29, C30 |
| 21 | 79.74 | 5.57 1H, d, 9.6 Hz | C20, C22, C29, C30 |
|    |       |                    | 21-O-Tig-C1, |
| 22 | 69.39 | 3.79, 1H, d, 9.6 Hz | C21, C28, |
| 23 | 22.60 | 1.06, 3H, s | C3, C4, C5, C24, |
| 24 | 66.14 | 4.15 (dd 16.8, 12 Hz) | C3, C4, C5, C-23 |
|    |       |                        | 24-O-Tig-C1' |
| 25 | 14.87 | 0.88, 3H, s | C-1, C-5, C-9, C-10 |
| 26 | 16.09 | 0.81, 3H, s | C-7, C-8, C-9, C-14 |
| 27 | 26.7 | 1.38, 3H, s | C-8, C13, C14, C-15 |
| 28 | 65.09 | 3.72 (dd 28.4, 10.4) | C16, C17, C-18, C-22 |
|    |       |                       | 28-O-Tig C1' |
| 29 | 29.24 | 0.74, 3H, s | C-19, C20, C-21, C-30 |
| 30 | 19.35 | 0.98, 3H, s | C-19, C20, C-21, C-29 |
| 21-O-Tig | | | |
| 1' | 167.05 | — | C21, Tig C-3', |
| 2' | 128.04 | — | Tig-C3', Tig C-4', Tig C-5' |
| 3' | 135.61 | 6.77, 1H, | Tig C-4', Tig C-5' |
| 4' | 11.94 | 1.79, br, m, 3H, | Tig C-1', C-2', C-3' |
| 5' | 13.84 | 1.78, br, m, 3H, | Tig C-1', C-2', C-3' |
| 24-O-Tig | | | |
| 1' | 167.26 | — | C24, Tig C-3' |
| 2' | 128.26 | — | Tig C-3', Tig C-4', Tig C-5' |
| 3' | 136.60 | 6.77, 1H, | Tig C-4', Tig C-5' |
| 4' | 11.94 | 1.79, br, m, 3H, | Tig C-1', C-2', C-3' |
| 5' | 13.96 | 1.78, br, m, 3H, | Tig C-1', C-2', C-3' |
| 28-O-Tig | | | |
| 1' | 166.64 | — | C28, Tig C-3' |
| 2' | 128.71 | — | Tig C-3', Tig C-4', Tig C-5' |
| 3' | 136.96 | 6.77, 1H, | Tig C-4', Tig C-5' |
| 4' | 12.09 | 1.79, br, m, 3H, | Tig C-1', C-2', C-3' |
| 5' | 14.06 | 1.78, br, m, 3H, | Tig C-1', C-2', C-3' |

What is claimed is:

1. A compound having the structure:

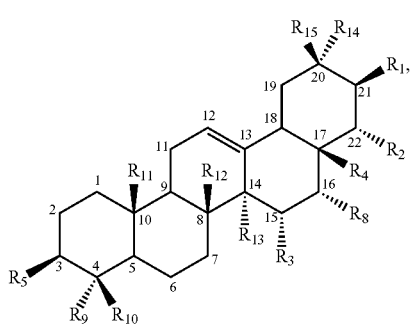
(K)

wherein R10 is selected from the group of CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, and CH2O-Ethylbutyryl; wherein R1, R2, R4, R5, and R8 are independently selected from the group of CH2OH, hydroxyl, O-angeloyl, O-tigloyl, O-senecioyl, O-acetyl, O-crotonoyl, O-3,3-dimethylartyloyl, O-cinnamoyl, O-pentenoyl, O-hexanoyl, O-benzoyl, O-ethylbutyryl, CH2O-angeloyl, CH2O-tigloyl, CH2O-senecioyl, CH2O-acetyl, CH2O-crotonoyl, CH2O-3,3-dimethylartyloyl, CH2O-cinnamoyl, CH2O-pentenoyl, CH2O-hexanoyl, CH2O-benzoyl, and CH2O-ethylbutyryl; wherein R3 is OH or H; wherein R9, R11, R12, R13, R14, and R15 are CH3.

2. The compound of claim 1, wherein R10 is CH2O-angeloyl, CH2O-tigloyl, CH2O-senecioyl, CH2O-crotonoyl, CH2O-3,3-dimethylartyloyl, CH2O-cinnamoyl, CH2O-Pentenoyl, CH2O-Hexanoyl, CH2O-benzoyl, or CH2O-Ethylbutyryl and at least 1 of R1, R2, R4, R5, R8, are O-angeloyl, O-tigloyl, O-senecioyl, O-acetyl, O-crotonoyl, O-3,3-dimethylartyloyl, O-cinnamoyl, O-pentenoyl, O-hexanoyl, O-benzoyl, O-ethylbutyryl, —CH2O-angeloyl, CH2O-tigloyl, CH2O-senecioyl, CH2O-crotonoyl, CH2O-3,3-dimethylartyloyl, CH2O-cinnamoyl, CH2O-Pentenoyl, CH2O-Hexanoyl, CH2O-benzoyl, or CH2O-Ethylbutyryl.

3. The compound of claim 1, wherein R1 is O-angeloyl, O-tigloyl, O-senecioyl, O-acetyl, O-crotonoyl, O-3,3-dimethylartyloyl, O-cinnamoyl, O-pentenoyl, O-hexanoyl, O-benzoyl, or O-ethylbutyryl, and R10 is CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, CH2O-ethylbutyryl.

4. The compound of claim 1, wherein R10 is CH2O-angeloyl, CH2O-tigloyl, CH2O-senecioyl, CH2O-crotonoyl, CH2O-3,3-dimethylartyloyl, CH2O-cinnamoyl, CH2O-Pentenoyl, CH2O-Hexanoyl, CH2O-benzoyl, CH2O-Ethylbutyryl.

5. The compound of claim 1, wherein R4 and R10 are independently—CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl.

6. The compound of claim 1, wherein the compound is selected from the following:

a) An isolated, purified or synthesized compound having structure:

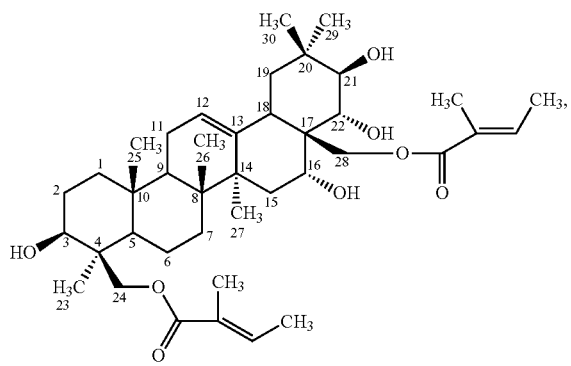

or chemical name: 24,28-O-Tigloyl-3β,16α,21β,22α,24β,28-hexahydroxyolean-12-ene b) An isolated, purified or synthesized compound having structure:

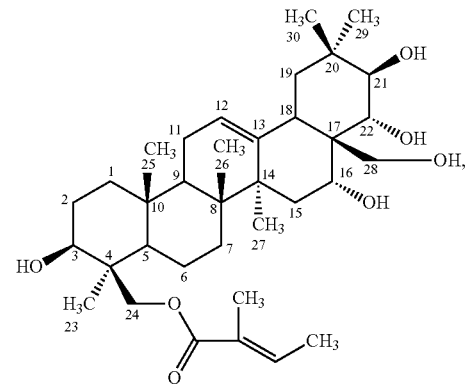

or chemical name: 24-O-Tigloyl-3β,16α, 21β,22α, 24β, 28-hexahydroxyolean-12-ene c) An isolated, purified or synthesized compound having structure:

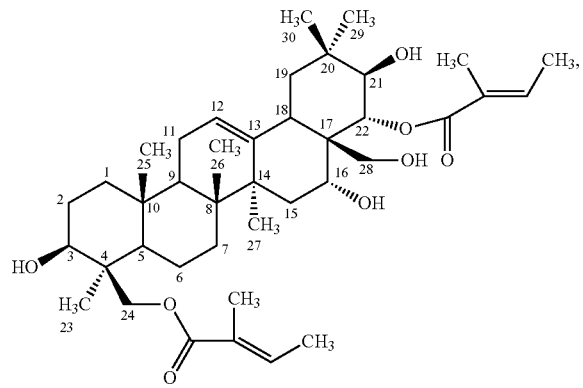

or chemical name: 22,28-O-Tigloyl-3β,16α,21β,22α, 24β,28-hexahydroxyolean-12-ene d) An isolated, purified or synthesized compound having structure:

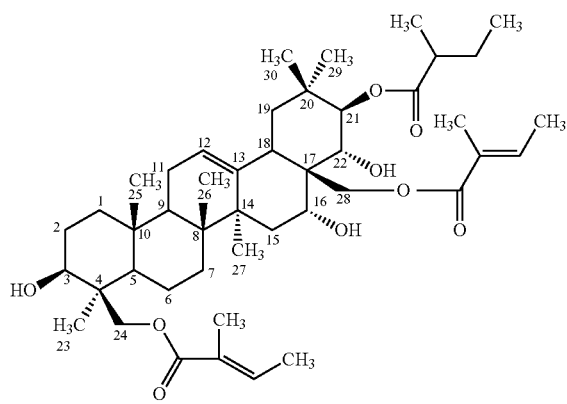

or chemical name: 21,24,28-O-Tigloyl-3β,16α,21β, 22α,24β,28-hexahydroxyolean-12-ene e) An isolated, purified or synthesized compound having structure:

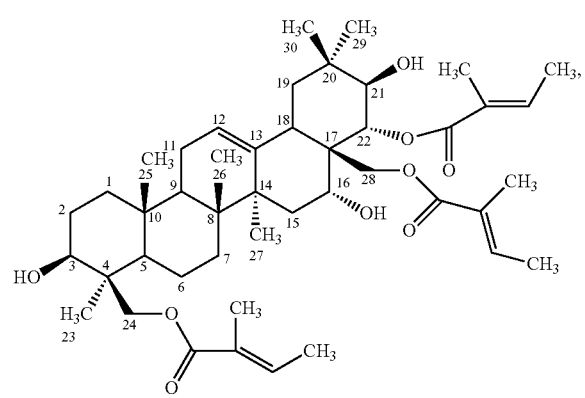

or chemical name: 22,24,28-O-Tigloyl-3β,16α,21β, 22α,24β,28-hexahydroxyolean-12-ene f) An isolated, purified or synthesized compound having structure:

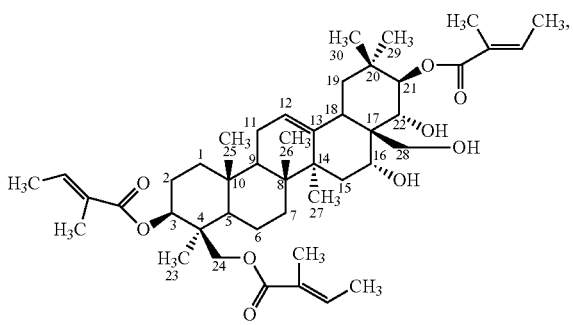

or chemical name: 3,21,28-O-Tigloyl-3β,16α,21β,22α, 24β,28-hexahydroxyolean-12-ene g) An isolated, purified or synthesized compound having structure:

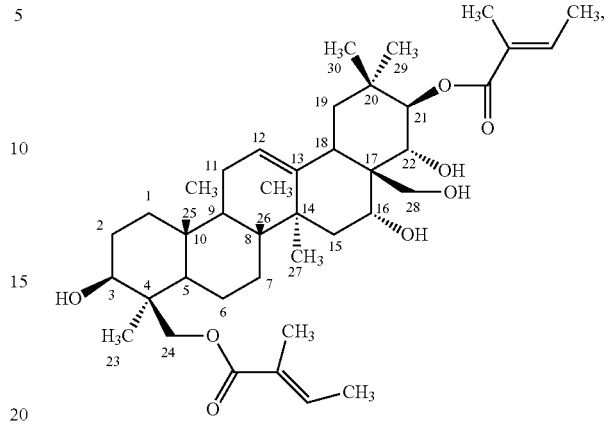

or chemical name: 21,24-O-Tigloyl-3β,16α,21β,22α, 24β,28-hexahydroxyolean-12-ene.

7. The compound of claim 1, wherein the compound is attached one or more of the functional groups selected from the group consisting of angeloyl, tigloyl, senecioyl, acetyl, crotonoyl, dimethylartyloyl, cinnamoyl, pentenoyl, hexanoyl, benzoyl, ethylbutyryl, alkyl and phenyl; wherein the compound can be obtained by a method comprising the following steps:

1. Dissolving core compound, triterpenes, hydroxylated triterpenes core in pyridine;
2. Adding the functional group or acyl chloride;
3. Stirring the mixture for a length of time including 5 sec, 1 min, 2 min, 5 min, 10 min, 30 min, 1 hr, 2 hr, 18 hr, 2 days or 3 days at different temperature;
4. At the end of reaction, adding an aqueous solution of acid or base, or water to the reaction mixture;
5. Extracting the solution with ethyl acetate followed by lyophilization;
6. Dissolving the reaction product in acetonitrile with Trifluoroacetic acid or DMSO;
7. Testing the reaction product of mixtures and individual fractions with MTT cytotoxic assay;
8. Selecting the HPLC fractions for isolation according to the cytotoxic activity of the reaction product obtained at a specific reaction time;
9. Purifying the active esterification products with HPLC;
10. Collecting the products; and
11. Testing the products.

8. A method for inhibiting cancer cell growth, inhibiting cancer cell invasion, inhibiting cancer cell metastasis, modulating cancer cell adhesion, or modulating cancer cell attachment, wherein the cancer is selected from the group of breast cancer, liver cancer, ovarian cancer, bladder cancer, prostatic cancer, skin cancer, bone cancer, brain cancer, leukemia cancer, lung cancer, colon cancer, melanoma cancer, cervical cancer, kidney cancer, pancreatic cancer, and mouth cancer, comprising contacting said cancer cell in a cell culture with an effective amount of compound, wherein the compound is selected from the structure:

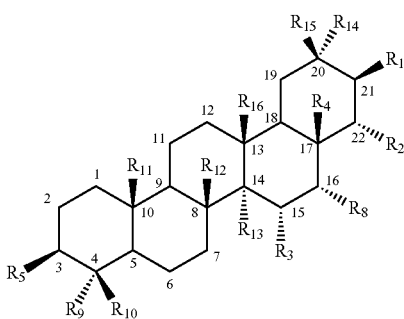

(2A)

wherein R10 is selected from the group of CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, CH2O-ethylbutyryl;

wherein R1, R2, R4, R5, R8, are independently selected from the group of CH2OH, hydroxyl, O-angeloyl, O-tigloyl, O-senecioyl, O-acetyl, O-crotonoyl, O-3,3-dimethylartyloyl, O-cinnamoyl, O-pentenoyl, O-hexanoyl, O-benzoyl, O-ethylbutyryl, O-benzoyl, CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, and CH2O-ethylbutyryl;

R3 is H or OH; R9, R11, R12, R13, R14 and R15 are CH3; and

R16 is H or R4 and R16 may together form —CH2-X—, CH(OH)—X— or C(=O)—X—, wherein the —X— may be O or NH or S.

9. A method for inhibiting cancer cell growth, inhibiting cancer cell invasion, inhibiting cancer cell metastasis, modulating cancer cell adhesion, or modulating cancer cell attachment, wherein the cancer is selected from the group of breast cancer, liver cancer, ovarian cancer, bladder cancer, prostatic cancer, skin cancer, bone cancer, brain cancer, leukemia cancer, lung cancer, colon cancer, melanoma cancer, cervical cancer, kidney cancer, pancreatic cancer, and mouth cancer, comprising contacting said cancer cell in vitro with an effective amount of compound selected from the structure:

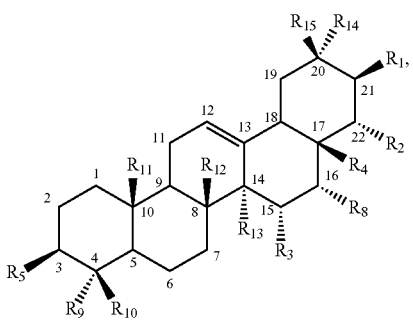

(K)

wherein R10 is selected from the group of CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, CH2O-ethylbutyryl;

wherein R1, R2, R4, R5, R8, are independently selected from the group of CH2OH, hydroxyl, O-angeloyl, O-tigloyl, O-senecioyl, O-acetyl, O-crotonoyl, O-3,3-dimethylartyloyl, O-cinnamoyl, O-pentenoyl, O-hexanoyl, O-benzoyl, O-ethylbutyryl, O-benzoyl, CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, and CH2O-ethylbutyryl;

R3 is H or OH; and R9, R11, R12, R13, R14 and R15 are CH3.

10. The method of claim 9, wherein R10 is CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl; R1, R2, R5 and R8 are OH; and R4 is CH2OH.

11. The method of claim 9, wherein R10 and R4 are independently CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl; and R1, R2, R5 and R8 are OH.

12. The method of claim 9, wherein R10 and R4 are independently CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, CH2O-ethylbutyryl; wherein R2, R5, R8, are OH; wherein R1 is O-angeloyl, O-tigloyl, O-senecioyl, O-acetyl, O-crotonoyl, O-3,3-dimethylartyloyl, O-cinnamoyl, O-pentenoyl, O-hexanoyl, O-benzoyl, or O-ethylbutyryl.

13. The method of claim 9, wherein R10 is CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl; R1 is O-angeloyl, O-tigloyl, O-senecioyl, O-acetyl, O-crotonoyl, O-3,3-dimethylartyloyl, O-cinnamoyl, O-pentenoyl, O-hexanoyl, O-benzoyl, O-ethylbutyryl, or O-benzoyl; R2, R5 and R8 are OH; and R4 is CH2OH.

14. The method of claim 9, wherein R10 is CH2O-tigloyl; and R1, R2, R4, R5 and R8 are OH or $CH_2OH$.

15. The method of claim 9, wherein R10 and R4 are CH2O-tigloyl; and R1, R2, R5 and R8 are OH.

16. The method of claim 8, wherein R10 is CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl; and R1, R2, R4, R5 and R8 are OH or CH2OH.

17. The method of claim 8, wherein R10 is CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl; R4 is CH2O-acetyl, CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl; and R1, R2, R5 and R8 are OH.

18. The method of claim 8, wherein R10 is CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl; R4 is CH2O-acetyl, CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl; R2, R5 and R8 are OH; and R1 is O-angeloyl, O-tigloyl, O-senecioyl, O-acetyl, O-crotonoyl, O-3,3-dimethylartyloyl, O-cinnamoyl, O-pentenoyl, O-hexanoyl, O-benzoyl, or O-ethylbutyryl.

19. The method of claim 8, wherein R10 is CH2O-angeloyl, CH2O-tigloyl, CH2O-senecioyl, CH2O-crotonoyl, CH2O-3,3-dimethylartyloyl, CH2O-cinnamoyl, CH2O-pentenoyl, CH2O-hexanoyl, CH2O-benzoyl, or CH2O-ethylbutyryl; R1 is O-angeloyl, O-tigloyl, O-senecioyl, O-acetyl, O-crotonoyl, O-3,3-dimethylartyloyl, O-cinnamoyl, O-pentenoyl, O-hexanoyl, O-ethylbutyryl, or O-benzoyl; R2, R5 and R8 are OH; and R4 is CH2OH.

20. The method of claim 9, wherein the compound is selected from the following:

a) A compound having structure:

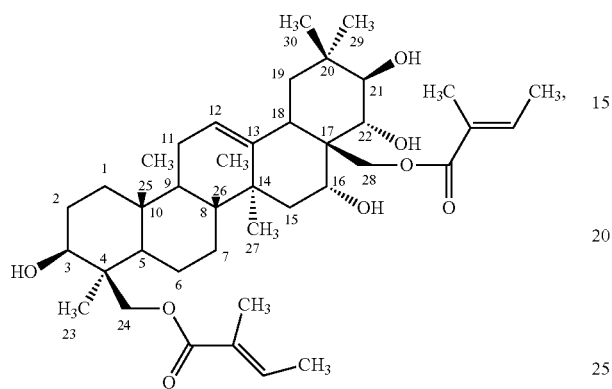

or chemical name: 24,28-O-Tigloyl-3β,16α,21β,22α,24β,28-hexahydroxyolean-12-ene, b) A compound having structure:

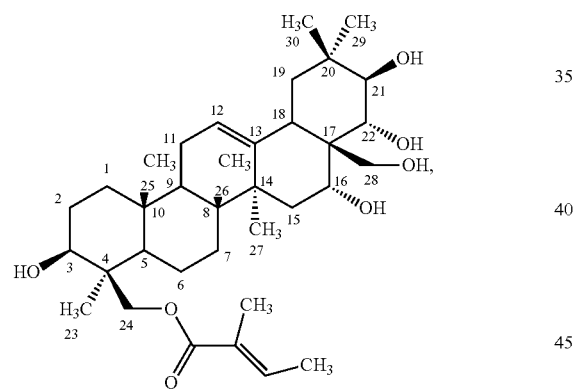

or chemical name: 24-O-Tigloyl-3β,16α,21β,22α,24β,28-hexahydroxyolean-12-ene, c) A compound having structure:

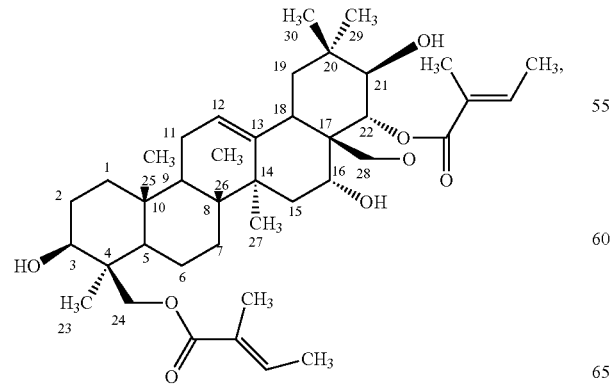

or chemical name: 22,28-O-Tigloyl-3β,16α,21β,22α,24β,28-hexahydroxyolean-12-ene, d) A compound having structure:

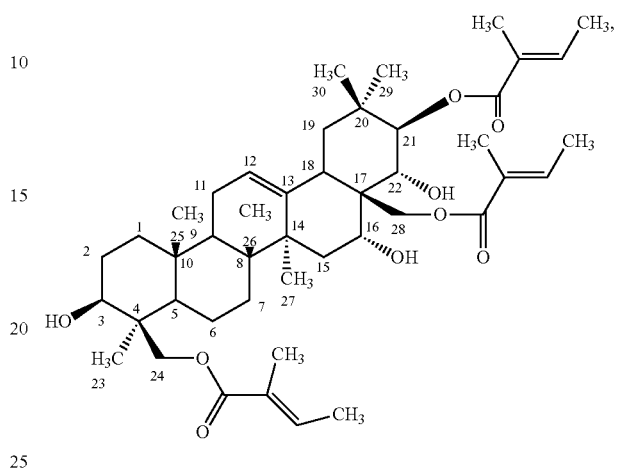

or chemical name: 21,24,28-O-Tigloyl-3β,16α,21β,22α,24β,28-hexahydroxyolean-12-ene, e) A compound having structure:

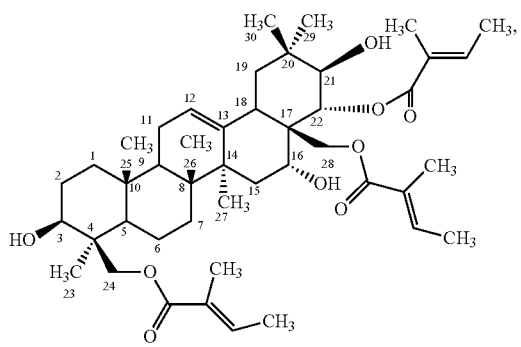

or chemical name: 22,24,28-O-Tigloyl-3β,16α,21β,22α,24β,28-hexahydroxyolean-12-ene, f) A compound having structure:

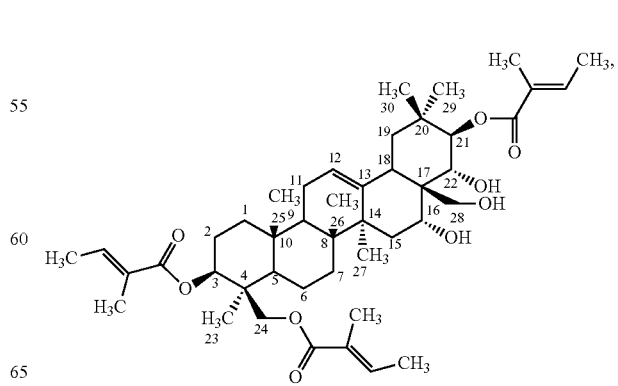

or chemical name: 3,21,28-O-Tigloyl-3β,16α,21β,22α,24β,28-hexahydroxyolean-12-ene,
g) A compound having structure:
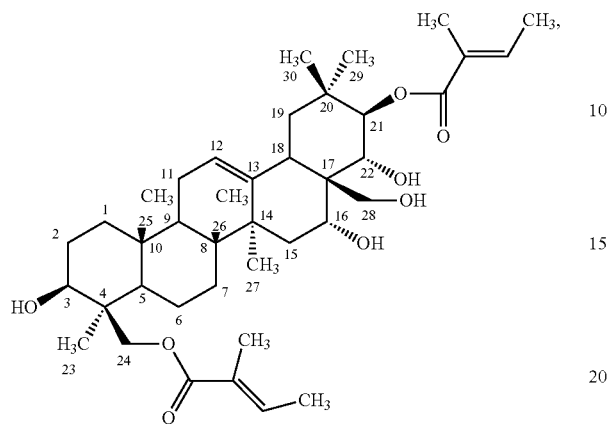
or chemical name: 21,24-O-Tigloyl-3β,16α,21β,22α,24β,28-hexahydroxyolean-12-ene.
* * * * *